US007935805B1

(12) United States Patent
Barnett et al.

(10) Patent No.: US 7,935,805 B1
(45) Date of Patent: *May 3, 2011

(54) POLYNUCLEOTIDES ENCODING ANTIGENIC HIV TYPE C POLYPEPTIDES, POLYPEPTIDES AND USES THEREOF

(75) Inventors: Susan Barnett, San Francisco, CA (US); Jan Zur Megede, San Francisco, CA (US)

(73) Assignee: Novartis Vaccines & Diagnostics, Inc, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/610,313

(22) Filed: Jul. 5, 2000

Related U.S. Application Data

(63) Continuation-in-part of application No. 09/475,704, filed on Dec. 30, 1999, now abandoned.

(60) Provisional application No. 60/114,495, filed on Dec. 31, 1998, provisional application No. 60/152,195, filed on Sep. 1, 1999.

(51) Int. Cl.
*C07H 21/04* (2006.01)
*A61K 49/00* (2006.01)

(52) U.S. Cl. ................... 536/23.72; 424/9.2

(58) Field of Classification Search ............. 435/320.1, 435/728, 252.3, 325, 410, 455, 254.11, 352, 435/358, 353, 763, 766, 772, 365, 372.3, 435/372, 456; 514/44; 424/325, 188.1, 139.1, 424/93.2, 9.2; 536/23.72
See application file for complete search history.

(56) References Cited

U.S. PATENT DOCUMENTS

| | | | |
|---|---|---|---|
| 4,652,639 A | 3/1987 | Stabinsky | |
| 4,861,707 A | 8/1989 | Ivanoff et al. | |
| RE33,653 E | 7/1991 | Mark et al. | |
| 5,032,510 A | 7/1991 | Kovacevic et al. | |
| 5,082,767 A | 1/1992 | Hatfield et al. | |
| 5,128,319 A | 7/1992 | Arlinghaus | |
| 5,130,247 A | 7/1992 | Kniskern et al. | |
| 5,156,949 A | 10/1992 | Luciw et al. | |
| 5,256,767 A | 10/1993 | Salk et al. | |
| 5,304,472 A | 4/1994 | Bass et al. | |
| 5,364,773 A | 11/1994 | Paoletti et al. | |
| 5,419,900 A | 5/1995 | Lane et al. | |
| 5,470,720 A * | 11/1995 | Helting et al. ................ 435/5 |
| 5,503,833 A | 4/1996 | Redmond et al. | |
| 5,550,280 A | 8/1996 | Dao-Cong et al. | |
| 5,622,705 A * | 4/1997 | Morrow ................ 424/199.1 |
| 5,637,677 A | 6/1997 | Greene et al. | |
| 5,665,569 A | 9/1997 | Ohno | |
| 5,665,720 A | 9/1997 | Young et al. | |
| 5,670,152 A | 9/1997 | Weiner et al. | |
| 5,683,864 A | 11/1997 | Houghton et al. | |
| 5,686,078 A | 11/1997 | Becker et al. | |
| 5,688,688 A | 11/1997 | Luciw et al. | |
| 5,693,755 A | 12/1997 | Buonagurio et al. | |
| 5,712,088 A | 1/1998 | Houghton et al. | |
| 5,714,596 A | 2/1998 | Houghton et al. | |
| 5,728,520 A | 3/1998 | Weiner et al. | |
| 5,738,852 A * | 4/1998 | Robinson et al. ........ 424/199.1 |
| 5,741,492 A | 4/1998 | Hurwitz et al. | |
| 5,750,373 A | 5/1998 | Garrard et al. | |
| 5,766,845 A | 6/1998 | Weiner et al. | |
| 5,786,464 A | 7/1998 | Seed | |
| 5,792,459 A | 8/1998 | Haigwood | |
| 5,795,737 A | 8/1998 | Seed et al. | |
| 5,797,870 A | 8/1998 | March et al. | |
| 5,817,637 A | 10/1998 | Weiner et al. | |
| 5,830,697 A * | 11/1998 | Sikic et al. ................ 435/69.1 |
| 5,837,242 A | 11/1998 | Holliger et al. | |
| 5,837,818 A | 11/1998 | Buonagurio et al. | |
| 5,840,313 A | 11/1998 | Vahine et al. | |
| 5,846,546 A | 12/1998 | Hurwitz et al. | |
| 5,853,736 A | 12/1998 | Becker et al. | |
| 5,858,646 A * | 1/1999 | Kang ................ 435/5 |
| 5,858,675 A | 1/1999 | Hillman et al. | |
| 5,859,193 A | 1/1999 | Devare et al. | |
| 5,866,320 A | 2/1999 | Rovinski et al. | |
| 5,871,747 A | 2/1999 | Gengoux-Sedlik et al. | |
| 5,876,724 A | 3/1999 | Girard et al. | |
| 5,876,731 A | 3/1999 | Sia et al. | |
| 5,879,907 A | 3/1999 | Aberg et al. | |
| 5,879,925 A | 3/1999 | Rovinski et al. | |
| 5,889,176 A | 3/1999 | Rovinski et al. | |
| 5,932,445 A | 8/1999 | Lal et al. | |
| 5,951,975 A | 9/1999 | Falo, Jr. et al. | |
| 5,955,342 A | 9/1999 | Rovinski et al. | |
| 5,965,726 A | 10/1999 | Pavlakis et al. | |
| 5,972,596 A | 10/1999 | Pavlakis et al. | |

(Continued)

FOREIGN PATENT DOCUMENTS

EP 0187041 7/1986

(Continued)

OTHER PUBLICATIONS

Ngo et al., Computational complexity, protein structure prediction, and the levinthal paradox, 1994, The Protein Folding Problem and Tertiary Structure Prediction, 491-494.*
Burton et al., Why do we not have an HIV vaccine and how can we make one?, 1998, Nature Medicine Vaccine Supplement, vol. 4, pp. 495-497.*
McCluskie et al., Route method of delivery of DNA vaccine influence immune responses in mice and non-human primates, 1999, Molecular Medicine, vol. 5, pp. 287-300.*
Azevedo et al., Main features of DNA-based immunization vectors, 1999, Brazilian Journal of Medical and Biological Research, vol. 32, pp. 147-153.*

(Continued)

*Primary Examiner* — J. E Angell
(74) *Attorney, Agent, or Firm* — Helen Lee; Regina Bautista

(57) ABSTRACT

The present invention relates to polynucleotides encoding immunogenic HIV type C Pol, Gag- and/or Env-containing polypeptides. Uses of the polynucleotides in applications including DNA immunization, generation of packaging cell lines, and production of Pol, Gag- and/or Env-containing proteins are also described.

51 Claims, 23 Drawing Sheets

U.S. PATENT DOCUMENTS

| | | | |
|---|---|---|---|
| 5,990,091 A | 11/1999 | Tartaglia et al. | |
| 6,001,977 A | 12/1999 | Chang et al. | |
| 6,004,763 A | 12/1999 | Gengoux et al. | |
| 6,025,125 A | 2/2000 | Rovinski et al. | |
| 6,060,273 A | 5/2000 | Dirks et al. | |
| 6,060,587 A | 5/2000 | Weiner et al. | |
| 6,063,384 A | 5/2000 | Morrow et al. | |
| 6,074,636 A | 6/2000 | Nichols | |
| 6,080,408 A | 6/2000 | Rovinski et al. | |
| 6,087,486 A | 7/2000 | Weiner et al. | |
| 6,090,388 A | 7/2000 | Wang | |
| 6,093,800 A | 7/2000 | Reiter et al. | |
| 6,096,505 A | 8/2000 | Selby et al. | |
| 6,099,847 A | 8/2000 | Tobin et al. | |
| 6,114,148 A | 9/2000 | Seed et al. | |
| 6,132,973 A | 10/2000 | Lal et al. | |
| 6,139,833 A | 10/2000 | Burgess et al. | |
| 6,139,843 A | 10/2000 | Rubinstein et al. | |
| 6,140,059 A | 10/2000 | Schawaller | |
| 6,146,635 A | 11/2000 | Cano et al. | |
| 6,172,201 B1 | 1/2001 | Weiner et al. | |
| 6,174,666 B1 | 1/2001 | Pavlakis et al. | |
| 6,214,804 B1 | 4/2001 | Felgner et al. | |
| 6,280,989 B1 | 8/2001 | Kapitonov et al. | |
| 6,291,157 B1 | 9/2001 | Rovinski et al. | |
| 6,291,664 B1 | 9/2001 | Pavlakis et al. | |
| 6,316,253 B1 | 11/2001 | Innis et al. | |
| 6,331,404 B1 | 12/2001 | Berman et al. | |
| 6,391,632 B1 * | 5/2002 | Dubensky et al. | 435/325 |
| 6,489,542 B1 * | 12/2002 | Corbin et al. | 800/302 |
| 6,541,248 B1 * | 4/2003 | Kingsman et al. | 435/325 |
| 6,602,705 B1 | 8/2003 | Barnett et al. | |
| 6,610,476 B1 * | 8/2003 | Chang et al. | 435/6 |
| 2003/0138453 A1 | 7/2003 | O'Hagan et al. | |

FOREIGN PATENT DOCUMENTS

| | | |
|---|---|---|
| EP | 0199301 A1 | 10/1986 |
| EP | 0242216 | 10/1987 |
| EP | 0314317 A1 | 5/1989 |
| EP | 0 449 116 A1 | 10/1991 |
| EP | 0449116 A1 | 10/1991 |
| EP | 0617132 A2 | 9/1994 |
| WO | WO 86/03224 | 6/1986 |
| WO | WO 87/02775 | 5/1987 |
| WO | WO 88/00471 | 1/1988 |
| WO | WO 88/10300 | 12/1988 |
| WO | WO 89/01940 | 3/1989 |
| WO | WO 89/02277 | 3/1989 |
| WO | WO 89/02922 | 4/1989 |
| WO | WO 89/03222 | 4/1989 |
| WO | WO-90/00556 | 1/1990 |
| WO | WO 90/02568 | 3/1990 |
| WO | WO 90/03984 | 4/1990 |
| WO | WO 90/10230 * | 9/1990 |
| WO | WO 90/10438 | 9/1990 |
| WO | WO 90/11092 | 10/1990 |
| WO | WO 90/11359 | 10/1990 |
| WO | WO 90/12094 | 10/1990 |
| WO | WO 90/15141 | 12/1990 |
| WO | WO 91/04273 | 4/1991 |
| WO | WO 91/06319 | 5/1991 |
| WO | WO 91/07425 | 5/1991 |
| WO | WO 91/07510 | 5/1991 |
| WO | WO 91/13360 | 9/1991 |
| WO | WO 91/13906 | 9/1991 |
| WO | WO 91/15238 | 10/1991 |
| WO | WO 91/15512 | 10/1991 |
| WO | WO 91/16926 | 11/1991 |
| WO | WO 91/18928 | 12/1991 |
| WO | WO 91/19803 | 12/1991 |
| WO | WO 92/03475 | 3/1992 |
| WO | WO 92/04046 | 3/1992 |
| WO | WO 92/05799 | 4/1992 |
| WO | WO 93/02102 | 2/1993 |
| WO | WO 93/04090 | 3/1993 |
| WO | WO 93/08836 | 5/1993 |
| WO | WO 93/14789 | 8/1993 |
| WO | WO 93/20212 | 10/1993 |
| WO | WO 93/21346 | 10/1993 |
| WO | WO 93/23569 | 11/1993 |
| WO | WO 94/04574 | 3/1994 |
| WO | WO 94/07922 | 4/1994 |
| WO | WO 94/11523 | 5/1994 |
| WO | WO 94/13804 | 6/1994 |
| WO | WO 94/15621 | 7/1994 |
| WO | WO 94/16060 | 7/1994 |
| WO | WO 94/16737 | 8/1994 |
| WO | WO 94/18221 | 8/1994 |
| WO | WO 94/20141 | 9/1994 |
| WO | WO 94/20640 | 9/1994 |
| WO | WO 94/22477 | 10/1994 |
| WO | WO 94/26293 | 11/1994 |
| WO | WO 94/29339 | 12/1994 |
| WO | WO 95/03407 | 2/1995 |
| WO | WO 95/04818 | 2/1995 |
| WO | WO 95/11317 | 4/1995 |
| WO | WO 95/11701 | 5/1995 |
| WO | WO 95/24485 | 9/1995 |
| WO | WO 95/25124 | 9/1995 |
| WO | WO 95/27505 | 10/1995 |
| WO | WO 95/29700 | 11/1995 |
| WO | WO 95/33206 | 12/1995 |
| WO | WO 95/33835 | 12/1995 |
| WO | WO 96/02273 | 2/1996 |
| WO | WO 96/02557 | 2/1996 |
| WO | WO 96/04382 | 2/1996 |
| WO | WO 96/09066 | 3/1996 |
| WO | WO 96/09378 | 3/1996 |
| WO | WO 96/09378 A1 | 3/1996 |
| WO | WO 96/16178 | 5/1996 |
| WO | WO 96/20732 | 7/1996 |
| WO | WO 96/23509 | 8/1996 |
| WO | WO 96/25177 | 8/1996 |
| WO | WO 96/30523 | 10/1996 |
| WO | WO 96/40290 | 12/1996 |
| WO | WO 97/03198 | 1/1997 |
| WO | WO 97/11605 | 4/1997 |
| WO | WO 97/26009 | 7/1997 |
| WO | WO 97/31115 A2 | 8/1997 |
| WO | WO-97/48370 | 12/1997 |
| WO | WO 98/08539 | 3/1998 |
| WO | WO-98/12207 | 3/1998 |
| WO | WO 9826075 * | 6/1998 |
| WO | WO 98/34640 | 8/1998 |
| WO | WO 98/41536 | 9/1998 |
| WO | WO 98/41645 | 9/1998 |
| WO | WO 98/43182 | 10/1998 |
| WO | WO 98/48843 | 11/1998 |
| WO | WO 98/59074 | 12/1998 |
| WO | WO 99/02694 | 1/1999 |
| WO | WO 99/06599 | 2/1999 |
| WO | WO 99/09412 | 2/1999 |
| WO | WO 99/12416 | 3/1999 |
| WO | WO 99/13864 | 3/1999 |
| WO | WO 99/16883 | 4/1999 |
| WO | WO 99/33346 | 7/1999 |
| WO | WO 99/41397 A1 | 8/1999 |
| WO | WO 99/41398 | 8/1999 |
| WO | WO 99/52463 | 10/1999 |
| WO | WO 99/53960 | 10/1999 |
| WO | WO 99/67395 | 12/1999 |
| WO | WO 00/08043 | 2/2000 |
| WO | WO 00/15819 | 3/2000 |
| WO | WO 00/18929 | 4/2000 |
| WO | WO 00/21556 | 4/2000 |
| WO | WO-00/29561 | 5/2000 |
| WO | WO 00/39302 | 7/2000 |
| WO | WO 00/39303 | 7/2000 |
| WO | WO 00/39304 | 7/2000 |
| WO | WO 00/44926 | 8/2000 |
| WO | WO 00/65076 | 11/2000 |
| WO | WO 00/66179 | 11/2000 |
| WO | WO 00/67761 | 11/2000 |
| WO | WO 00/67787 | 11/2000 |
| WO | WO 00/71561 | 11/2000 |
| WO | WO 01/02607 | 1/2001 |

| | | |
|---|---|---|
| WO | WO 01/12223 | 2/2001 |
| WO | WO 01/16342 | 3/2001 |
| WO | WO 01/19958 | 3/2001 |
| WO | WO 01/21270 | 3/2001 |
| WO | WO 01/26681 | 4/2001 |
| WO | WO 01/29225 | 4/2001 |
| WO | WO 01/36614 | 5/2001 |
| WO | WO 01/42308 | 6/2001 |
| WO | WO 01/43693 | 6/2001 |
| WO | WO 01/45748 | 6/2001 |
| WO | WO 01/46408 | 6/2001 |
| WO | WO 01/47955 | 7/2001 |
| WO | WO 01/54701 | 8/2001 |
| WO | WO 01/54719 | 8/2001 |
| WO | WO 01/60393 | 8/2001 |
| WO | WO 01/60838 | 8/2001 |
| WO | WO 03/004620 A2 | 1/2003 |
| WO | WO-03/020876 | 3/2003 |

OTHER PUBLICATIONS

Gurunathan et al., CD40 ligand/trimer DNA enhances both humoral and cellular immune responses and induces protective immunity to infectious and tumor challenge, 1998, Journal of Immunology, vol. 9, p. 4563.*

Nathanson et al., Biological considerations in the development of a human immunodeficiency virus vaccine, 2000, The Journal of Infectious Diseases, vol. 182, pp. 579-589.*

Anderson, Human gene therapy, 1998, Nature, vol. 392, pp. 25-30.*

Verma et al., gene therapy-promises, problems and prospects, 1997, Nature, vol. 389, pp. 239-242.*

Verschoor, Abstract #37, Comparison of immunity generated by nucleic acid, MF59 and iscom-formulated HIV-1 Gp120 vaccines in rhesus macaques, 1999, Medical Primatology, vol. 28, Issues 4/5.*

Heeney et al., HIV-1 vaccine-induced immune responses which correlate with protection from SHIV infection: compiled preclinical efficacy data from trials with ten different HIV-1 vaccine candidates, 1999, Immunology Letters 66, pp. 189-195.*

Barnett et al., DNA vaccines coming of age, 1999, Annual Rep. Med. Chem., pp. 149-158.*

Prince, gene transfer: A review of methods and applications, 1998, Pathology, vol. 30, pp. 335-347.*

I Kuby, Immunology,"Vaccines," $2^{nd}$ Ed., WH Freeman and Company 1994, pp. 469-471.*

Stedman's Medical Dictionary, Williams & Wilkins, $26^{th}$ Ed., 1995, pp. 852-853.*

J Richter et al., International Journal of Hematology, "Clinical Gene Therapy in Hematology: Past and Future," 2000, pp. 162-169.*

S Halene et al., Human Gene Therapy, "Gene Therapy Using Hematopoietic Stem Cells: Sisyphus Approaches the Crest," Jun. 2000, 11:1259-1267.*

P Chu et al., J Mol. Med., "Retrovirus-mediated gene transfer into human hematopoietic stem cells," 1998, 76: pp. 184-192.*

G Romano et al., Stem Cells, "Latest Developments in Gene Transfer Technology:Achievements, Perspectives, and Controversies over Therapeutic Applications," 2000, 18: 19-39.*

VFI Van Tendeloo et al., Leukemia, "Gene therapy: principles and applications to hematopoietic cells," 2001, 15, pp. 523-544.*

Baker et al., Science, 294:pp. 93-96, 2001.*

Attwood, T, Science, vol. 290, No. 5491, pp. 471-473, 2000.*

Gerhold et al., (BioEssays, vol. 18, No. 12, pp. 973-981, 1996.*

Russell et al., Journal of Molecular Biology, vol. 244, pp. 332-350, 1994.*

Wells et al., Journal of Leukocyte Biology, vol. 61, No. 5, pp. 545-550, 1997.*

ATCC catalog of cell lines and hybridomas (7th edition, Maryland, 1992, pp. 70, 79, 148, 150, 158, 164, 194, 299, 308, and 456).*

Kafri et al. Nat. Genet. 1997, 17:abstract.*

Lai et al. DNA and Cell Biology, 14, 1995, 643-651.*

Andre et al., "Increased Immune Response Elicited by DNA Vaccination with a Synthetic gp 120 Sequence with Optimized Condon Usage," Journal of Virology 72(2):1497-1503 (1998).

Barre-Sinoussi et al., "Isolation of a T-Lymphotropic Retrovirus from a Patient at Risk for Acquired Immune Deficiency Syndrome (AIDS)," Science 220:868-871 (1983).

Clavel et al., "Isolation of a New Human Retrovirus from West African Patients with AIDS," Science233:343-346 (1986).

Clavel et al., "Molecular Cloning and Polymorphism of the Human Immune Deficiency Virus Type 2," Nature 324:691-695 (1986).

Freed, E.O., "HIV-1 Gag Proteins: Diverse Functions in the Virus Life Cycle," Virology 251:1-15 (1998).

Haas et al., "Codon Usage Limitation in the Expression of HIV-1 Envelope Glycoprotein," Current Biology 6(3):315-324 (1996).

Levy et al., "Isolation of Lymphocytopathic Retroviruses from San Francisco Patients with AIDS," Science 225:840-842 (1984).

Montagnier et al., "Human T-Cell Leukemia Viruses: The Family of Human T-Lymphotropic Retroviruses: Their Role in Malignancies and Association with AIDS," Gallo, Essex & Gross, eds., pp. 363-379 (1984).

Popovic et al., "Detection, Isolation, and Continuous Production of Cytopathic Retroviruses (HTLV-III) from Patients with AIDS and Pre-AIDS," Science 224:497-500 (1984).

Schneider et al., "Inactivation of the Human Immunodeficiency Virus Type 1 Inhibitory Elements Allows Rev-Independent Expression of Gag and Gag/Protease and Particle Formation," Journal of Virology 71(7):4892-4903 (1997).

Vilmer et al., "Isolation of New Lymphotropic Retrovirus from Two Siblings with Haemophilia B, One with AIDS," The Lancet 1:753 (1984).

Wang et al., "Assembly of HIV GAG-B-Galactosidase Fusion Proteins into Virus Particles," Virology 200:524-534 (1994).

Guyader et al., "Genome Organization and Transactivation of the Human Immunodeficiency Virus Type 2," Nature 326:662-669 (1987).

GenBank accession No. AF110965.

GenBank accession No. AF110967.

GenBank accession No. AF110968.

GenBank accession No. AF110975.

GenBank accession No. M65024.

Adams et al., "The Expression of Hybrid Hiv:ty Virus-like Particles in Yeast," Nature 329:68-70 (1987).

Arthur, et al., "Serological Responses in Chimpanzees Inoculated with Human Immunodeficiency Virus Glycoprotein (Gp120) Subunit Vaccine," Proc Natl Acad Sci USA 84(23):8583-8587 (1987).

Baker et al., "Structures of Bovine and Human Papillomaviruses. Analysis by Cryoelectron Microscopy and Three-dimensional Image Reconstruction," Biophys. J. 60:1445-1456 (1991).

Barr, et al., "Antigenicity and Immunogenicity of Domains of the Human Immunodeficiency Virus (HIV) Envelope Polypeptide Expressed in the Yeast Saccharomyces cerevisiae," Vaccine 5(2):90-101 (1987).

Barrett, et al., "Large-scale production and purification of a vaccinia recombinant-derived HIV-1 gp160 and analysis of its immunogenicity," AIDS Res Hum Retroviruses 5(2):159-71 (1989).

Beard, W. A., et al.,"Role of the "Helix Clamp" in HIV-1 Reverse Transcriptase Catalytic Cycling as Revealed by Alanine-Scanning Mutagenesis," Journal of Biological Chemistry 271(21):12213-12220 (1996).

Berger, P.B., "New Directions in Research: Report from the 10th International Conference on AIDS," Canadian Medical Association Journal 152(12):1991-1995 (1995).

Berman, et al., "Human Immunodeficiency Virus Type 1 Challenge of Chimpanzees Immunized with Recombinant Envelope Glycoprotein gp120," Proc Natl Acad Sci USA 85(14):5200-5204 (1988).

Berman, et al., "Expression and Immunogenicity of the Extracellular Domain of the Human Immunodeficiency Virus Type 1 Envelope Glycoprotein, gp160," J Virol. 63(8):3489-3498 (1989).

Birx and Redfield, "HIV Vaccine Therapy," Int J Immunopharmacol. 13(1):129-132 (1991).

Bolognesi, D.P., "Progress in Vaccines Against AIDS," Science 246:1233-1234 (1989).

Borrow, et al., "Virus-Specific CD8+ Cytotoxic T-Lymphocyte Activity Associated with Control of Viremia in Primary Human Immunodeficiency Virus Type 1 Infection," J Virol. 68(9):6103-6110 (1994).

Bourgault, et al., "Cytotoxic T-Cell Response and AIDS-Free Survival in Simian Immunodeficiency Virus-Infected Macaques," *AIDS.* 7 (Suppl 2):S73-S79 (1993).

Brown et al., "Chimeric Parvovirus B19 Capsids for the Presentation of Foreign Epitopes," *Virology* 198:477-488 (1994).

Bujacz, G., et al., "The Catalytic Domain of Human Immunodeficiency Virus Integrase: Ordered Active Site in the F185H Mutant," *Febs Letters* 398(2-3):175-178 (1996).

Carmichael et al., "Quantitative Analysis of the Human Immunodeficiency Virus Type 1 (Hiv-1)-specific Cytotoxic T Lymphocyte (Ctl) Response at Different Stages of Hiv-1 Infection: Differential Ctl Responses to Hiv-1 and Epstein-barr Virus in Late Disease," *J Exp Med.* 177(2):249-256 (1993).

Chazal N. et al., "Phenotypic Characterization of Insertion Mutants of the Human Immunodeficiency Virus Type 1 Gag Precursor Expressed in Recombinant Baculovirus-infected Cells," *Virology* 68(1):111-122 (1994).

Ciernik et al., "Induction of Cytotoxic T Lymphocytes and Antitumor Immunity with Dna Vaccines Expressing Single T Cell Epitopes," *J. Immunol.* 156(7):2369-2375 (1996).

Daar et al., "Transient High Levels of Viremia in Patients with Primary Human Immunodeficiency Virus Type 1 Infection," *N Engl J Med.* 324(14):961-964 (1991).

Davey et al., "Subcutaneous administration of interleukin-2 in human immunodeficiency virus type 1-infected persons," *J Infect Dis.* 175(4):781-789 (1997).

Davies J. F., et al., "Crystal structure of the ribonuclease H domain of HIV-1 reverse transcriptase," *Science* 252(5002):88-95 (1991).

Deminie et al., "Evaluation of Reverse Transcriptase and Protease Inhibitors in Two-drug Combinations Against Human Immunodeficiency Virus Replication," *Antimicrob Agents Chemother.* 40(6):1346-1351 (1996).

Desai et al., "Molecular Cloning and Primary Nucleotide Sequence Analysis of a Distinct Human Immunodeficiency Virus Isolate Reveal Significant Divergence in its Genomic Sequence," *Proc. Natl. Acad. Sci. USA* 83:8380-8384 (1986).

Doe et al., "Induction of HIV-1 Envelope (gp120)-Specific Cytotoxic T Lymphocyte Responses in Mice by Recombinant CHO Cell-Derived gp120 is Enhanced by Enzymatic Removal of N-Linked Glycans," *Eur. J. Immunol.* 24:2369-2376 (1994).

Doe, B. and Walker, C.M. "HIV-1 p24 Gag-Specific Cytotoxic T-Lymphocyte Responses in Mice," *AIDS* 10(7);793-794 (1996).

Dyda F., et al., "Crystal Structure of the Catalytic Domain of HIV-1 Integrase: Similarity to Other Polynucleotidyl Transferases," *Science* 266(5193):1981-1986 (1994).

Earl et al., "Isolate-and Group-specific Immune Responses to the Envelope Protein of Human Immunodeficiency Virus Induced by a Live Recombinant Vaccinia Virus in Macaques," *AIDS Res Hum Retroviruses* 5(1):23-32 (1989).

Edelman, R., "Vaccine Adjuvants," *Rev Infect Dis.* 2(3):370-383 (1980).

Engelman, A. et al., "Structure-based Mutagenesis of the Catalytic Domain of Human Immunodeficiency Virus Type 1 Integrase," *Journal of Virology* 71(5):3507-3514 (1997).

Esnouf et al., "Mechanism of Inhibition of HIV-1 Reverse Transcriptase by Nonnucleoside Inhibitors," *Structural Biology* 2(4) 303-308 (1995).

Evans et al., "An Engineered Poliovirus Chimaera Elicits Broadly Reactive Hiv-1 Neutralizing Antibodies," *Nature* 339(6223):385-388 (1989).

Faust et al., "Outpatient Biopsies of the Palatine Tonsil: Access to Lymphoid Tissue for Assessment of Human Immunodeficiency Virus RNA Titers," *Otolaryngol Head Neck Surg.* 114(4):593-598 (1996).

Fennie et al., "Model for Intracellular Folding of the Human Immunodeficiency Virus Type 1 gp120," *J Virol.* 63(2):639-646 (1989).

Ferre et al., "Combination Therapies Against HIV-1 Infection:Exploring the Concept of Combining Antiretroviral Drug Treatments with HIV-1 Immune-Based Therapies in Asymptomatic Individuals," *AIDS Patient Care STDS* 10(6):357-361 (1996).

Fisher, et al., "Biologically diverse molecular variants within a single HIV-1 isolate," *Nature* 334:444-447 (1988).

Fox et al., "No Winners Against AIDS," *Bio/Technology* 12(2):128 (1994).

Garnier, L. et al., "Particle Size Determinants in the Human Immunodeficiency Virus Type 1 Gag Protein," *J Virol* 72(6):4667-4677 (1998).

Goldgur, Y. et al., "Three New Structures of the Core Domain of HIV-1 Integrase: an Active Site That Binds Magnesium," *Proceedings of the National Academy of Sciences of the United States of America* 95(16):9150-9154 (1998).

Goudsmit et al., "Human Immunodeficiency Virus Type 1 Neutralization Epitope with Conserved Architecture Elicits Early Type-specific Antibodies in Experimentally Infected Chimpanzees," *Proc. Natl. Acad. Sci. USA* 85:4478-4482 (1988).

Greene, "AIDS and the Immune System," *Scientific American* Sep. :99-105 (1993).

Griffiths J.C. et al., "Hybrid Human Immunodeficiency Virus Gag Particles as an Antigen Carrier System: Induction of Cytotoxic T-cell and Humoral Responses by a Gag:V3 Fusion," *J. Virol.* 67(6):3191-3198 (1993).

Grimison B. and Laurence, J., "Immunodominant Epitope Regions of HIV-1 Reverse Transcriptase: Correlations with HIV-1+ Serum IgG Inhibitory to Polymerase Activity and With Disease Progression," *Journal of Acquired Immune Deficiency Syndromes and Human Retrovirology* 9(1):58-68 (1995).

Gurgo et al., "Envelope Sequences of Two New United States HIV-1 Isolates," *Virology* 164:531-536 (1988).

Hagensee et al., "Three-dimensional Structure of Vaccinia Virus-produced Human Papillomavirus Type 1 Capsids," *J. Virol.* 68:4503-4505 (1994).

Hahn et al., "Genetic Variation in HTLV-III/LAV Over Time in Patients with AIDS or at Risk for AIDS," *Science* 232:1548-1553 (1986).

Hammer et al., "Issues in Combination Antiretroviral Therapy: a Review," *J Acquir Immune Defic Syndr.* 7(Suppl 2):S24-S37 (1994).

Haynes et al., "Update on the Issues of Hiv Vaccine Development," *Ann Med.* 28(1):39-41 (1996).

Haynes et al., "Toward an Understanding of the Correlates of Protective Immunity to Hiv Infection" *Science* 271:324-328 (1996).

Heeney et al., "Beta-chemokines and Neutralizing Antibody Titers Correlate with Sterilizing Immunity Generated in HIV-1 Vaccinated Macaques," *Proc Natl Acad Sci USA* 95(18):10803-10808 (1998).

Hickman, A. B., et al., "Biophysical and enzymatic properties of the catalytic domain of HIV-1 integrase," *Journal of Biological Chemistry* 269(46):29279-29287 (1994).

Ho et al., "Human Immunodeficiency Virus Neutralizing Antibodies Recognize Several Conserved Domains on the Envelope Glycoproteins," *J Virol.* 61(6):2024-2028 (1987).

Jacobo-Molina, A. et al., "Crystal Structure of Human Immunodeficiency Virus Type 1 Reverse Transcriptase Complexed with Double-stranded DNA at 3.0 A Resolution Shows Bent DNA," *Proceedings of the National Academy of Sciences of the United States of America* 90(13):6320-6324 (1993).

Katz, R. A. and Skalka, A. M., "The Retroviral Enzymes," *Annual Review of Biochemistry* 63:133-73 (1994).

Keefer, et al., "Safety and Immunogenicity of Env 2-3, a Human Immunodeficiency Virus Type 1 Candidate Vaccine, in Combination with a Novel Adjuvant, MTP-PE/MF59. NIAID AIDS Vaccine Evaluation Group," *AIDS Res Hum Retroviruses.* 12(8):683-693 (1996).

Kirnbauer et al., "Efficient Self-assembly of Human Papillomavirus Type 16 L1 and L1-L2 into Virus-Like Particles," *J. Virol.* 67:6929-6936 (1993).

Klenerman, et al., "Original Antigenic Sin Impairs Cytotoxic T Lymphocyte Responses to Viruses Bearing Variant Epitopes," *Nature* 394(6692):482-485 (1998).

Koff et al., "Development and Testing of AIDS Vaccines," *Science* 241:426-432 (1988).

Koff and Schultz, "Progress and Challenges Toward and AIDS Vaccine: Brother, Can You Spare a Paradigm?" *J. Clinical Immunology* 16(3):127-133 (1996).

Kohl et al., "Active Human Immunodeficiency Virus Protease Is Required for Viral Infectivity," *PNAS USA* 85:4686-4690 (1988).

Kohlstaedt, L. A. et al., "Crystal Structure at 3.5 A Resolution of HIV-1 Reverse Transcriptase Complexed with an Inhibitor," *Science* 256(5065):1783-1790 (1992).

Koup et al., "Temporal Association of Cellular Immune Responses with the Initial Control of Viremia in Primary Human Immunodeficiency Virus Type 1 Syndrome," *J. Virol.* 68(7):4650-4655 (1994).

Kovacs et al., "Increases in CD4 T Lymphocytes with Intermittent Courses of Interleukin-2 in Patients with Human Immunodeficiency Virus Infection," *New England J. Med.* 332(9):567-575 (1995).

Kovacs et al., "Controlled Trial of Interleukin-2 Infusions in Patients Infected with the Human Immunodeficiency Virus," *N Engl J Med.* 335(18):1350-1356 (1996).

Krausslich et al., "Processing of in Vitro-synthesized Gag Precursor Proteins of Human Immunodeficiency Virus (HIV) Type 1 by HIV Proteinase Generated in *Escherichia coli*," *J. Virol.* 62:4393-4397 (1988).

Kreuter J., et al., "Mode of Action of Immunological Adjuvants: Some Physicochemical Factors Influencing the Effectivity of Polyacrylic Adjuvants," *Infect Immun.* 19(2):667-675 (1978).

Krug, M. S. and Berger, S. L., "Reverse Transcriptase from Human Immunodeficiency Virus: a Single Template-primer Binding Site Serves Two Physically Separable Catalytic Functions," *Biochemistry* 30(44):10614-10623 (1991).

Lalvani A. et al., "Rapid effector Function in CD8+ Memory T Cells," *J. Exp. Med.* 186:859-865 (1997).

Lasky et al., "Delineation of a Region of the Human Immunodeficiency Virus Type 1 gp120 Glycoprotein Critical for Interaction with the CD4 Receptor," *Cell* 50(6):975-985 (1987).

Littman et al., "Unusual Intron in the Immunoglobulin Domain of the Newly Isolated Murine CD4 (L3T4) Gene," *Nature* 325(6103):453-455 (1987).

Looney et al., "Type-restricted Neutralization of Molecular Clones of Human Immunodeficiency Virus," *Science* 241:357-359 (1988).

Maddon et al., "The Isolation and Nucleotide Sequence of a Cdna Encoding the T Cell Surface Protein T4: a New Member of the Immunoglobulin Gene Family," *Cell* 42(1):93-104 (1985).

Maignan, S., et al. "Crystal Structures of the Catalytic Domain of HIV-1 Integrase Free and Complexed with its Metal Cofactor: High Level of Similarity of the Active Site with Other Viral Integrases," *Journal of Molecular Biology* 282(2):359-368 (1998).

Manca et al., "Antigenicity of Hiv-derived T Helper Determinants in the Context of Carrier Recombinant Proteins: Effect on T Helper Cell Repertoire Selection," *Eur J Immunol.* 26(10):2461-2469 (1996).

Mazumder, A., et al., "Effects of nucleotide analogues on human immunodeficiency virus type 1 integrase," *Molecular Pharmacology* 49(4):621-628 (1996).

Mazza et al., "Recombinant Interleukin-2 (Ril-2) in Acquired Immune Deficiency Syndrome (Aids): Preliminary Report in Patients with Lymphoma Associated with Hiv Infection," *Eur J Haematol.* 49(1):1-6 (1992).

Mcheyzer-Williams, M.G. et al, "Enumeration and Characterization of Memory Cells in the Th Compartment," *Immunol. Rev.* 150:5-21 (1996).

McCluskie, et al., "Route and method of delivery of DNA vaccine influence immune responses in mice and non-human primates," *Mol Med.* 5(5):287-300 (1999).

McCornack et al., "HIV Protease Substrate Conformation: Modulation by Cyclophilin A," *FEBS Letts* 414:84-88 (1997).

McMichael, A.J. and O'Callaghan, C.A., "A New Look at T Cells," *J. Exp. Med.* 187(9)1367-1371 (1998).

Modrow et al., "Computer-assisted Analysis of Envelope Protein Sequences of Seven Human Immunodeficiency Virus Isolates: Prediction of Antigenic Epitopes in Conserved and Variable Regions," *J. Virol.* 61(2):570-578 (1987).

Myers et al., "Human Retroviruses and AIDS," published by the Los Alamos National Laboratory, Los Alamos, NM, 1991, pp. I-A-48 to I-A-56 and II-77 to II-88.

Novitsky et al., "Molecular Cloning and Phylogenetic Analysis of Human Immunodeficiency Virus Type 1 Subtype C: a Set of 23 Full-Length Clones from Botswana," *J. Virol.* 73(5):4427-4432 (1999).

Nowak and Bangham, "Population Dynamics of Immune Responses to Persistent Viruses," *Science* 272(5258):74-79 (1996).

Odile et al., "Anti-HIV Active Immunization, Evidence for Persistent Cell Mediated Immunity after a 2 Year Follow Up," Eighth International Conference on AIDS/III STD World Congress Amsterdam, The Netherlands Jul. 19-24, 1992, Abstract No. MOB 0024.

Okuda et al., "Induction of Potent Humoral and Cell-mediated Immune Responses Following Direct Injection of DNA Encoding the HIV Type 1 Env and Rev gene Products," *AIDS Res Hum Retroviruses.* 11(8):933-943 (1995).

Palaniappan, C. et al., "Mutations Within the Primer Grip Region of HIV-1 Reverse Transcriptase Result in Loss of RNase H Function," *Journal of Biological Chemistry* 272(17):11157-11164 (1997).

Park et al., "Overexpression of The Gag-pol Precursor From Human Immunodeficiency Virus Type 1 Proviral Genomes Results in Efficient Proteolytic Processing in The Absence of Virion Production," *J. Virol.* 65:5111 (1991).

Patel et al., "Insights into DNA Polymerization Mechanisms from Structure and Function Analysis of HIV-1 Reverse Transcriptase," *Biochemistry* 34:5351-5363 (1995).

Perelson, et al., "Decay Characteristics of Hiv-1-infected Compartments During Combination Therapy," *Nature* 387(6629):188-191 (1997).

Pyle et al., "Immune Response to Immunostimulatory Complexes (ISCOMs) Prepared from Human Immunodeficiency Virus Type 1 (HIV-1) or the HIV-1 External Envelope Glycoprotein (gp120)," *Vaccine* 7(5):465-473 (1989).

Redfield and Birx, "Hiv-specific Vaccine Therapy: Concepts, Status, and Future Directions," *AIDS Res Hum Retroviruses* 8(6):1051-1058 (1992).

Reicin, A.S. et al., "Linker Insertion Mutations in the Human Immunodeficiency Virus Type 1 Gag Gene: Effects on Virion Particle Assembly, Release, and Infectivity," *J. Virol.* 69(2):642-650 (1995).

Robey, et al., "Prospect for Prevention of Human Immunodeficiency Virus Infection: Purified 120-kDa Envelope Glycoprotein Induces Neutralizing Antibody," *Proc Natl Acad Sci USA* 83(18):7023-7027 (1986).

Rodgers, D. W. et al., "The Structure of Unliganded Reverse Transcriptase from the Human Immunodeficiency Virus Type 1," *Proceedings of the National Academy of Sciences of the United States of America* 92(4):1222-1226 (1995).

Saag, et al., "Extensive Variation of Human Immunodeficiency Virus Type-1 in vivo," *Nature* 334:440-444 (1988).

Saag and Kuritzkes, "Strategies for Continuing Antiretroviral Therapy," *Intl AIDS Society USA* 4(2):16-19 (1996).

Salk et al., "Prospects for the Control of Aids by Immunizing Seropositive Individuals," *Nature* 327(6122):473-476 (1987).

Schernthaner, et al., "Endosperm-specific Activity of a Zein Gene Promoter in Transgenic Tobacco Plants," *The EMBO J.* 7:1249-1259 (1988).

Schulhafer et al., "Acquired Immunodeficiency Syndrome: Molecular Biology and its Therapeutic Intervention (review)," *In Vivo* 3(2):61-78 (1989).

Sheng N. and Dennis, D., "Active Site Labeling of HIV-1 Reverse Transcriptase," *Biochemistry* 32(18):4938-4942 (1993).

Smith et al., "Blocking of HIV-1 infectivity by a soluble, secreted form of the CD4 antigen," *Science* 238(4834):1704-1707 (1987).

Spence R. A., et al., "Mechanism of Inhibition of HIV-1 Reverse Transcriptase by Nonnucleoside Inhibitors," *Science* 267(5200):988-993 (1995).

Srinivasan et al., "Molecular Characterization of Human Immunodeficiency Virus from Zaire: Nucleotide Sequence Analysis Identifies Conserved and Variable Domains in the Envelope Gene," *Gene* 52:71-82 (1987).

Starcich et al., "Identification and Characterization of Conserved and Variable Regions in the Envelope Gene of HTLV-III/LAV, the Retrovirus of AIDS," *Cell* 45:637-648 (1986).

Steimer et al., "Genetically Engineered Human Immunodeficiency Envelope Glycoprotein Gp120 Produced in Yeast is the Target of Neutralizing Antibodies," *Vaccines* 87:236-241 (1987).

Sternberg et al., "Prediction of Antigenic Determinants and Secondary Structures of the Major Aids Virus Proteins," *FEBS Letters* 218(2):231-237 (1987).

Tindle et al., "Chimeric Hepatitis B Core Antigen Particles Containing B- and Th-epitopes of Human Papillomavirus Type 16 E7 Protein Induce Specific Antibody and T-helper Responses in Immunised Mice," *Virology* 200:547-557 (1994).

Vacca et al., "L-735,524: an Orally Bioavailable Human Immunodeficiency Virus Type 1 Protease Inhibitor," *Proc Natl Acad Sci USA* 91(9):4096-4100 (1994).

Wagner R., et al., "Studies on Processing, Particle Formation, and Immunogenicity of the HIV-1 gag Gene Product: a Possible Component of a HIV Vaccine," *Arch Virol.* 127:117-137 (1992).

Wagner et al., "Assembly and Extracellular Release of Chimeric HIV-1 PR55gag Retrovirus-like Particles," *Virology* 200:162-175 (1994).

Wagner et al., "Construction, Expression, and Immunogenicity of Chimeric HIV-1 Virus-like Particles," *Virology* 220:128-140 (1996).

Wakefield, J. K. et al., "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome," *Journal of Virology* 66(11):6806-6812 (1992).

Wan et al., "Autoprocessing: an Essential Step for the Activation of HIV-1 Protease," *Biochem. J.* 316:569-573 (1996).

Wang et al., "Induction of Humoral and Cellular Immune Responses to the Human Immuno-deficiency Type 1 Virus in Nonhuman Primates by in Vivo DNA Inoculation," *Virology* 211(1):102-112 (1995).

Wang C. et al., "Analysis of Minimal Human Immunodeficiency Virus Type 1 Gag Coding Sequences Capable of Virus-like Particle Assembly and Release," *J Virol* 72(10): 7950-7959 (1998).

Wu X., et al., "Targeting foreign proteins to human immunodeficiency virus particles via fusion with Vpr and Vpx," *J. Virol.* 69(6):3389-3398 (1995).

Yeni et al., "Antiretroviral and Immune-based Therapies: Update," *AIDS* 7(Suppl 1):S173-S184 (1993).

Yenofsky et al., "A Mutant Neomycin Phosphotransferase II Gene Reduces the Resistance of Transformants to Antibiotic Selection Pressure," *Proc. Natl. Acad. Sci. USA* 87:3435-3439 (1990).

Yourno et al., "Nucleotide Sequence Analysis of the Env Gene of a New Zairian Isolate of HIV-1," *AIDS Res Hum Retroviruses* 4(3):165-73 (1988).

Zagury et al., "Progress Report IV on Aids Vaccine in Human: Phase I Clinical Trial in Hiv Infected Patients," *VII International Conference on AIDS*, Florence Jun. 16-21, 1991, Abstract No. M.A. 67.

Zagury et al., "One-year Follow-up of Vaccine Therapy in Hiv-infected Immune-deficient Individuals: a New Strategy," *J. Acquired Immune Deficiency Syndromes* 5:676-681 (1992).

Zhang Y., et al., "Analysis of the Assembly Function of the Human Immunodeficiency Virus Type 1 Gag Protein Nucleocapsid Domain," *J Virol* 72(3):1782-1789 (1998).

zur Megede et al., "Increased Expression and Immunogenicity of Sequence-modified Human Immunodeficiency Virus Type 1 Gag Gene," *J Virol.* 74(6):2628-2635 (2000).

Haas et al., "Cytotoxin T-Cell Responses to HIV-1 Reverse Transcriptase, Integrase and Protease," AIDS, 12:1427-1436 (1998).

Hamajima, et al., "The Combination of DNA and Peptide Vaccines Induces Strong Immunities Against HIV-1 in Both Humoral and CMI," 11$^{th}$ International AIDS Conference, Vancouver, Britich Columbia, Jul. 7-12; 11:6 (abstract No. Mo.A.151) (1996).

Kent, et al., "A Recombinant Avipoxvirus HIV-1 Vaccine Expressing Interferon-Gamma is Safe and Immunogenic in Macaques," Vaccine 18:2250-2256 (2000).

Williamson, et al., "Designing HIV-1 Subtype C Vaccines for South Africa," South African Journal of Science, 96:318-324 (2000).

André et al., "Increased Immune Response Elicited by DNA Vaccination with a Synthetic gp120 Sequence with Optimized Codon Usage," *Journal of Virology*, Feb. 1998, pp. 1497-1503.

Notivsky et al., "Molecular Cloning and Phylogenetic Analysis of Human Immunodeficiency Virus Type 1 Subtype C: A Set of 23 Full-Length Clones from Botswana," *Journal of Virology*, May 1999, pp. 4427-4432.

Barnett et al. (Jun. 2001). "The ability of an oligomeric human immunodeficiency virus type 1 (HIV-1) envelope antigen to elicit neutralizing antibodies against primary HIV-1 isolates is improved following partial deletion of the second hypervariable region," *J Virol.* 75(12):5526-40.

Bolognesi et al. (1994). "NIH conference. HIV vaccine development: a progress report," *Ann. Int. Med.* 8(7):603-611.

Borsetti et al., (1998). "The C-terminal half of the human immunodeficiency virus type 1 Gag precursor is sufficient for efficient particle assembly." *Virol.* 72(11):9313-9317.

Brusic et al. (1998). "Prediction of MHC class II-binding peptides using an evolutionary algorithm and artificial neural network," *Bioinformatics* 14(2):121-30.

Burton et al. (1997). "The antibody response in HIV-1 infection" *AIDS* 11(Suppl. A):S87-S98.

Cao et al. (1997) "Replication and neutralization of human immunodeficiency virus type 1 lacking the V1 and V2 variable loops of the gp120 envelope glycoprotein" *J. Virol.* 71(12):9808-9812.

Carter, (1994) "Epitope Mapping of a Protein Using the Geysen (PEPSCAN) Procedure," *Methods Mol. Biol.* 36:207-23.

Chang et al. (Aug. 2000). "Human immunodeficiency virus type 1 subtype E envelope recombinant peptides containing naturally immunogenic epitopes," *J Infect Dis.* 182(2):442-50.

Cheng-Mayer, (1989) "Isolates of human immunodeficiency virus type 1 from the brain may constitute a special group of the AIDS virus," *PNAS USA* 86:8575-8579.

Dai, L. C., et al. (1992) "Mutation of human immunodeficiency virus type 1 at amino acid 585 on gp41 results in loss of killing by CD8+ A24-restricted cytotoxic T lymphocytes," *J. Virol.* 66(5):3151-3154.

Davenport et al. (1995) "An empirical method for the prediction of T-cell epitopes," *Immunogenetics* 42:392-97.

Desrosiers, R. C., (2004). "Prospects for an AIDS vaccine," *Nat. Med.* 10(3):221-223.

D'Souza et al., (1997). "Evaluation of monoclonal antibodies to human immunodeficiency virus type 1 primary isolates by neutralization assays: performance criteria for selecting candidate antibodies for clinical trials. AIDS Clinical Trials Group Antibody Selection Working Group." *J. Infect. Dis.* 175:1056-1062.

Earl et al., (1990). "Oligomeric structure of the human immunodeficiency virus type 1 envelope glycoprotein" *PNAS USA* 87:648-652.

Earl et al., (1991). "Biological and immunological properties of human immunodeficiency virus type 1 envelope glycoprotein: analysis of proteins with truncations and deletions expressed by recombinant vaccinia viruses" *J. Virol* 65:31-41.

Feller & De La Cruz, (1991). "Identifying antigenic T-cell sites," *Nature* 349(6311):720-721.

Fenoglio, D., et al., (2000). "Natural analogue peptides of HIV-1 gp120 T-helper epitope antagonize response of gp120-specific human CD4 T-cell clones," *J AIDS* 23:1-7.

Fiore et al. (1994). "The biological phenotype of HIV-1 is usually retained during and after sexual transmission" *Virol.* 204:297-303.

Geysen et al. (1984). "Use of peptide synthesis to probe viral antigens for epitopes to a resolution of a single amino acid," *PNAS USA* 81:3998-4002.

Hopp, (1993). "Retrospective: 12 Years of Antigenic Determinant Predictions and More," *Peptide Research* 6:183-90.

Hu et al., (1992). "Protection of macaques against SIV infection by subunit vaccines of SIV envelope glycoprotein gp160," *Science* 255:456-459.

Instructions to Authors, 2008, *J. Virol.* 82(1):1-19.

Jameson et al., (1988). "The antigenic index: a novel algorithm for predicting antigenic determinants," *CABIOS* 4(1):1818-1886.

Javaherian et al., (1989). "Principal neutralizing domain of the human immunodeficiency virus type 1 envelope protein" *PNAS* 86:6786-6772.

Jeffs et al., (1996). "Antigenicity of truncated forms of the human immunodeficiency virus type 1 envelope glycoprotein" *J. of Gen. Virol.* 77:1403-1410.

Johnson et al. (1991). *The Journal of Immunology* 147:1512-13 and 1515-1521.

Johnson, P. R., et al., (1992). "Identification of overlapping HLA class I-restricted cytotoxic T cell epitopes in a conserved region of the human immunodeficiency virus type 1 envelope glycoprotein: definition of minimum epitopes and analysis of the effects of sequence variation," *J. Exp. Med.* 175:961-971.

Kang et al., (1991). "Evidence for non-V3-specific neutralizing antibodies that interfere with gp120/CD4 binding in human immunodeficiency virus 1-infected humans" *PNAS USA* 88:6171-6175.

Kolaskar et al. (1990). "A semi-empirical method for prediction of antigenic determinants on protein antigens." *FEBS Lett.* 276:172-174.

Kwong et al., (1998). "Structure of an HIV gp120 envelope glycoprotein in complex with the CD4 receptor and a neutralizing human antibody" *Nature* 393:648-659.

Lee et al., (2000). "A single point mutation in HIV-1 V3100p alters the immunogenic properties of rgp120," *Arch Virol.* 145(10):2087-2103.

Levitus et al., (1999). "Main features of DNA-based immunization vectors," *Brazilian Journal of Medical and Biological Research* 32:147-153.

Liu, Y., et al., (2006). "Selection on the human immunodeficiency virus type 1 proteome following primary infection," *J. Virol.* 80(19):9519-9529.

Lu et al., (1998). "Immunogenicity of DNA vaccines expressing human immunodeficiency virus type 1 envelope glycoprotein with and without deletions in the V1/2 and V3 regions" *AIDS Res. Hum. Retroviruses* 14(2):151-155.

Maksyutov & Zagrebelnaya, (1993). "ADEPT: a computer program for prediction of protein antigenic determinants," *Comput. Appl. Biosci.* 9(3):291-297.

Mammano et al., (1994). "Role of the major homology region of human immunodeficiency virus type 1 in virion morphogenesis" *J. Virol.* 68(8):4927-4936.

Mascola et al., (1994). "Two antigenically distinct subtypes of human immunodeficiency virus type 1: viral genotype predicts neutralization serotype" *J. Infect. Dis.* 169:48-54.

Matsushita et al., (1988). "Characterization of a human immunodeficiency virus neutralizing monoclonal antibody and mapping of the neutralizing epitope" *J. Virol.* 62:2107-2144.

Matthews (1986). "Restricted neutralization of divergent human T-lymphotropic virus type III isolates by antibodies to the major envelope glycoprotein," *PNAS USA* 83:9709-9713.

McDougal et al., (1986). "Binding of the human retrovirus HTLV-III/LAV/ARV/HIV to the CD4 (T4) molecule: conformation dependence, epitope mapping, antibody inhibition, and potential for idiotypic mimicry" *J. Immunol.* 137:2937-2944.

McLain, L., et al., (2001). "Different effects of a single amino acid substitution on three adjacent epitopes in the gp41 C-terminal tall of a neutralizing antibody escape mutant of human immunodeficiency virus type 1," *Arch. Virol.* 146:157-166.
Meister et al., (1995). "Two novel T cell epitope prediction algorithms based on MHC-binding motifs; comparison of predicted and published epitopes from Mycobacterium tubereculosis and HIV protein sequences," *Vaccine* 13(6):581-591.
Montefiori et al., (1999). "Toward an HIV type 1 vaccine that generates potent, broadly cross-reactive neutralizing antibodies" *AIDS Res. Hum. Retroviruses* 15(8):689-698.
Moore et al. (1995). *Vaccine* 13:1741-1749.
Nara et al., (1988). "Purified envelope glycoproteins from human immunodeficiency virus type 1 variants induce individual, type-specific neutralizing antibodies" *J. Virol.* 62:2622-2628.
Palker et al., (1988). "Type-specific neutralization of the human immunodeficiency virus with antibodies to env-encoded synthetic peptides" *PNAS USA* 85:1932-1936.
Pantaleo, G., and R. A. Koup, (2004). "Correlates of immune protection in HIV-1 infection: what we know, what we don't know, what we should know," *Nat. Med.* 10(8):806-810.
Peng et al., (1997). "Enhancement or inhibition of HIV-1 replication by intracellular expression of sense or antisense RNA targeted at different intermediates of reverse transcription" *AIDS* 11:587-595.
Persson, et al. (1998). "Modifications of HIV-1 Retrovirus-like Particles to Enhance Safety and Immunogenicity," *Biologicals* 26:255-265.
Putney et al., (1986). "HTLV-III/LAV-neutralizing antibodies to an *E. coli*-produced fragment of the virus envelope" *Science* 234:1392-1395.
Ratner et al., (1985). "Complete nucleotide sequence of the AIDS virus, HTLV-III" *Nature* 313:277-284.
Robert-Guroff et al., (1985). "HTLV-III-neutralizing antibodies in patients with AIDS and AIDS related complex" *Nature* (London) 316:72-74.
Roberts et al., (1996). "Prediction of HIV Peptide Epitopes by a Noval Algorithm," *AIDS Res. Hum. Retroviruses* 12(7):593-610.
Rusche et al., (1988). "Antibodies that inhibit fusion of human immunodeficiency virus-infected cells bind a 24-amino acid sequence of the viral envelope, gp120" *PNAS USA* 85:3198-3202.
Sanchez-Pescador et al., (1985). "Nucleotide sequence and expression of an AIDS-associated retrovirus (ARV-2)" *Science* 227(4686):484-492.
Schwartz, et al. (1992) "Mutational inactivation of an inhibitory sequence in human immunodeficiency virus type 1 results in Rev-independent gag expression," *J Virol.* 66(12):7176-7182.
Stamatatos et al., (1998). "Effect of major deletions in the V1 and V2 loops of a macrophage-tropic HIV type 1 isolate on viral envelope structure, cell entry, and replication" *AIDS Res. Hum. Retroviruses* 14(13):1129-1139.
Stamatatos et al., (1998). "The ability of an oligomeric human immunodeficiency virus type 1 (HIV-1) envelope antigen to elicit neutralizing antibodies against primary HIV•1 isolates is improved following partial deletion of the second hypervariable region" *J. Virol.* 72(10):7840-7845.
Thali et al., (1993). "Characterization of conserved human immunodeficiency virus type 1 gp120 neutralization epitopes exposed upon gp120-CD4 binding" *J. Virol.* 67(7):3978-3988.
Trkola et al., (1995). "Cross-clade neutralization of primary isolates of human immunodeficiency virus type 1 by human monoclonal antibodies and tetrameric CD4-IgG" *J. Virol.* 69(11):6609-6617.
Watkins, B. A., et al., (1993). "Immune escape by human immunodeficiency virus type 1 from neutralizing antibodies: evidence for multiple pathways," *J. Virol.* 67(12):7493-7500.
Weiss et al., (1985). "Neutralization of human T-Lymphotropic virus type III by sera of AIDS and AIDS-risk patients" *Nature* (London) 316:69-72.
Weiss et al., (1986). "Variable and conserved neutralization antigens of human immunodeficiency virus" *Nature* (London) 324:572-575.
Welling et al., (1985). "Prediction of sequential antigenic regions in proteins," *FEBS Lett.* 188:215-18.
Wyatt et al., (1995). "Involvement of the V1N2 variable loop structure in the exposure of human immunodeficiency virus type 1 gp120 epitopes induced by receptor binding" *J. Virol.* 69(9):5723-5733.
Wyatt et al., (1998). "The antigenic structure of the HIV gp120 envelope glycoprotein" *Nature* 393:705-711.
Zhu et al., (1993). "Genotypic and phenotypic characterization of HIV-1 patients with primary infection," *Science* 261:1179-1181.
zur Megede et al., (2006). "Evaluation of human immunodeficiency type 1 subtype C gag, pol, and gagpol DNA and alphavirus replicon vaccines," *Vaccine* 24:2755-2763.
zur Megede et al., (Jun. 2003). "Expression and Immunogenicity of Sequence-modified Human Immunodeficiency Virus Type 1 Subtype B pol and gagpol DNA Vaccines," *J Virol.* 77(11):6197-6207.

* cited by examiner

Gag_AF110965_BW_mod
ATGGGCGCCCGCGCCAGCATCCTGCGCGGCGGCAAGCTGGACGCCTGGGAGCGCATCCGCC
TGCGCCCCGGCGGCAAGAAGTGCTACATGATGAAGCACCTGGTGTGGGCCAGCCGCGAGCT
GGAGAAGTTCGCCCTGAACCCCGGCCTGCTGGAGACCAGCGAGGGCTGCAAGCAGATCATC
CGCCAGCTGCACCCCGCCCTGCAGACCGGCAGCGAGGAGCTGAAGAGCCTGTTCAACACCG
TGGCCACCCTGTACTGCGTGCACGAGAAGATCGAGGTCCGCGACACCAAGGAGGCCCTGGA
CAAGATCGAGGAGGAGCAGAACAAGTGCCAGCAGAAGATCCAGCAGGCCGAGGCCGCCGAC
AAGGGCAAGGTGAGCCAGAACTACCCCATCGTGCAGAACCTGCAGGGCCAGATGGTGCACC
AGGCCATCAGCCCCCGCACCCTGAACGCCTGGGTGAAGGTGATCGAGGAGAAGGCCTTCAG
CCCCGAGGTGATCCCCATGTTCACCGCCCTGAGCGAGGGCGCCACCCCCCAGGACCTGAAC
ACGATGTTGAACACCGTGGGCGGCCACCAGGCCGCCATGCAGATGCTGAAGGACACCATCA
ACGAGGAGGCCGCCGAGTGGGACCGCGTGCACCCCGTGCACGCCGGCCCCATCGCCCCCGG
CCAGATGCGCGAGCCCCGCGGCAGCGACATCGCCGGCACCACCAGCACCCTGCAGGAGCAG
ATCGCCTGGATGACCAGCAACCCCCCCATCCCCGTGGGCGACATCTACAAGCGGTGGATCA
TCCTGGGCCTGAACAAGATCGTGCGGATGTACAGCCCCGTGAGCATCCTGGACATCAAGCA
GGGCCCCAAGGAGCCCTTCCGCGACTACGTGGACCGCTTCTTCAAGACCCTGCGCGCCGAG
CAGAGCACCCAGGAGGTGAAGAACTGGATGACCGACACCCTGCTGGTGCAGAACGCCAACC
CCGACTGCAAGACCATCCTGCGCGCTCTCGGCCCCGGCGCCAGCCTGGAGGAGATGATGAC
CGCCTGCCAGGGCGTGGGCGGCCCCAGCCACAAGGCCCGCGTGCTGGCCGAGGCGATGAGC
CAGGCCAACACCAGCGTGATGATGCAGAAGAGCAACTTCAAGGGCCCCCGGCGCATCGTCA
AGTGCTTCAACTGCGGCAAGGAGGGCCACATCGCCCGCAACTGCCGCGCCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAGCC
GCCCCGAGCCCACCGCCCCCCCGCCGAGAGCTTCCGCTTCGAGGAGACCACCCCCGGCCA
GAAGCAGGAGAGCAAGGACCGCGAGACCCTGACCAGCCTGAAGAGCCTGTTCGGCAACGAC
CCCCTGAGCCAGTAA

FIG. 1

Gag_AF110967_BW_mod
ATGGGCGCCCGCGCCAGCATCCTGCGCGGCGAGAAGCTGGACAAGTGGGAGAAGATCCGCC
TGCGCCCCGGCGGCAAGAAGCACTACATGCTGAAGCACCTGGTGTGGGCCAGCCGCGAGCT
GGAGGGCTTCGCCCTGAACCCCGGCCTGCTGGAGACCGCCGAGGGCTGCAAGCAGATCATG
AAGCAGCTGCAGCCCGCCCTGCAGACCGGCACCGAGGAGCTGCGCAGCCTGTACAACACCG
TGGCCACCCTGTACTGCGTGCACGCCGGCATCGAGGTCCGCGACACCAAGGAGGCCCTGGA
CAAGATCGAGGAGGAGCAGAACAAGTCCAGCAGAAGACCCAGCAGGCCAAGGAGGCCGAC
GGCAAGGTGAGCCAGAACTACCCCATCGTGCAGAACCTGCAGGGCCAGATGGTGCACCAGG
CCATCAGCCCCGCACCCTGAACGCCTGGGTGAAGGTGATCGAGGAGAAGGCCTTCAGCCC
CGAGGTGATCCCCATGTTCACCGCCCTGAGCGAGGGCGCCACCCCCAGGACCTGAACACG
ATGTTGAACACCGTGGGCGGCCACCAGGCCGCCATGCAGATGCTGAAGGACACCATCAACG
AGGAGGCCGCCGAGTGGGACCGCCTGCACCCCGTGCAGGCCGGCCCCGTGGCCCCCGGCCA
GATGCGCGACCCCCGCGGCAGCGACATCGCCGGCGCCACCAGCACCCTGCAGGAGCAGATC
GCCTGGATGACCAGCAACCCCCCCGTGCCCGTGGGCGACATCTACAAGCGGTGGATCATCC
TGGGCCTGAACAAGATCGTGCGGATGTACAGCCCCGTGAGCATCCTGGACATCCGCCAGGG
CCCCAAGGAGCCCTTCCGCGACTACGTGGACCGCTTCTTCAAGACCCTGCGCGCCGAGCAG
GCCACCCAGGACGTGAAGAACTGGATGACCGAGACCCTGCTGGTGCAGAACGCCAACCCCG
ACTGCAAGACCATCCTGCGCGCTCTCGGCCCCGGCGCCACCCTGGAGGAGATGATGACCGC
CTGCCAGGGCGTGGGCGGCCCCGGCCACAAGGCCCGCGTGCTGGCCGAGGCGATGAGCCAG
GCCAACAGCGTGAACATCATGATGCAGAAGAGCAACTTCAAGGGCCCCCGGCGCAACGTCA
AGTGCTTCAACTGCGGCAAGGAGGGCCACATCGCCAAGAACTGCCGCGCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAACC
GCAGCGAGCCCGCCGCCCCCACCGTGCCCACCGCCCCCCCGCCGAGAGCTTCCGCTTCGA
GGAGACCACCCCCGCCCCCAAGCAGGAGCCCAAGGACCGCGAGCCCTACCGCGAGCCCCTG
ACCGCCCTGCGCAGCCTGTTCGGCAGCGGCCCCCTGAGCCAGTAA
```

FIG. 2

Env_AF110968_C_BW_opt

--> signal peptide (1-81)
ATGCGCGTGATGGGCATCCTGAAGAACTACCAGCAGTGGTGGATGTGGGGCATCCTGGGCTTCTGGATGCTGATCA
\/--> gp120/140/160 (82)
TCAGCAGCGTGGTGGGCAACCTGTGGGTGACCGTGTACTACGGCGTGCCCGTGTGGAAGGAGGCCAAGACCACCCT
GTTCTGCACCAGCGACGCCAAGGCCTACGAGACCGAGGTGCACAACGTGTGGGCCACCCACGCCTGCGTGCCCACC
GACCCCAACCCCCAGGAGATCGTGCTGGAGAACGTGACCGAGAACTTCAACATGTGGAAGAACGACATGGTGGACC
AGATGCACGAGGACATCATCAGCCTGTGGGACCAGAGCCTGAAGCCCTGCGTGAAGCTGACCCCCCTGTGCGTGAC
CCTGAAGTGCCGCAACGTGAACGCCACCAACAACATCAACAGCATGATCGACAACAGCAACAAGGGCGAGATGAAG
AACTGCAGCTTCAACGTGACCACCGAGCTGCGCGACCGCAAGCAGGAGGTGCACGCCCTGTTCTACCGCCTGGACG
TGGTGCCCCTGCAGGGCAACAACAGCAACGAGTACCGCCTGATCAACTGCAACACCAGCGCCATCACCCAGGCCTG
CCCCAAGGTGAGCTTCGACCCCATCCCCATCCACTACTGCACCCCCGCCGGCTACGCCATCCTGAAGTGCAACAAC
CAGACCTTCAACGGCACCGGCCCCTGCAACAACGTGAGCAGCGTGCAGTGCGCCCACGGCATCAAGCCCGTGGTGA
GCACCCAGCTGCTGCTGAACGGCAGCCTGGCCAAGGGCGAGATCATCATCCGCAGCGAGAACCTGGCCAACAACGC
CAAGATCATCATCGTGCAGCTGAACAAGCCCGTGAAGATCGTGTGCGTGCGCCCCAACAACAACACCCGCAAGAGC
GTGCGCATCGGCCCCGGCCAGACCTTCTACGCCACCGGCGAGATCATCGGCGACATCCGCCAGGCCTACTGCATCA
TCAACAAGACCGAGTGGAACAGCACCCTGCAGGGCGTGAGCAAGAAGCTGGAGGAGCACTTCAGCAAGAAGGCCAT
CAAGTTCGAGCCCAGCAGCGGCGGCGACCTGGAGATCACCACCCACAGCTTCAACTGCCGCGGCGAGTTCTTCTAC
TGCGACACCAGCCAGCTGTTCAACAGCACCTACAGCCCCAGCTTCAACGGCACCGAGAACAAGCTGAACGGCACCA
TCACCATCACCTGCCGCATCAAGCAGATCATCAACATGTGGCAGAAGGTGGGCCGCGCCATGTACGCCCCCCCCAT
CGCCGGCAACCTGACCTGCGAGAGCAACATCACCGGCCTGCTGCTGACCCGCGACGGCGGCAAGACCGGCCCCAAC
GACACCGAGATCTTCCGCCCCGGCGGCGGCGACATGCGCGACAACTGGCGCAACGAGCTGTACAAGTACAAGGTGG
                                                         gp120(1512)<--\/-->(1513)gp41
TGGAGATCAAGCCCCTGGGCGTGGCCCCCACCGAGGCCAAGCGCCGCGTGGTGGAGCGCGAGAAGCGCGCCGTGGG
CATCGGCGCCGTGTTCCTGGGCTTCCTGGGCGCCGCCGGCAGCACCATGGGCGCCGCCAGCATCACCCTGACCGTG
CAGGCCCGCCTGCTGCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGACCCGCATCCTGGCCGTGGAGCGCTACCTGAAGGACCA
GCAGCTGCTGGGCATCTGGGGCTGCAGCGGCAAGCTGATCTGCACCACCGCCGTGCCCTGGAACAGCAGCTGGAGC
AACCGCAGCCACGACGAGATCTGGGACAACATGACCTGGATGCAGTGGGACCGCGAGATCAACAACTACACCGACA
CCATCTACGCCCTGCTGGAGGAGAGCCAGAACCAGCAGGAGAAGAACGAGAAGGACCTGCTGGCCCTGGACAGCTG
                    gp140(2025)<--\/
GCAGAACCTGTGGAACTGGTTCAGCATCACCAACTGGCTGTGGTACATCAAGATCTTCATCATGATCGTGGGCGGC
CTGATCGGCCTGCGCATCATCTTCGCCGTGCTGAGCATCGTGAACCGCGTGCGCCAGGGCTACAGCCCCCTGCCCT
TCCAGACCCTGACCCCCAACCCCCGCGAGCCCGACCGCCTGGGCCGCATCGAGGAGGAGGGCGGCGAGCAGGACCG
CGGCCGCAGCATCCGCCTGGTGAGCGGCTTCCTGGCCCTGGCCTGGGACGACCTGCGCAGCCTGTGCCTGTTCAGC
TACCACCGCCTGCGCGACTTCATCCTGATCGCCGCCCGCGTGCTGGAGCTGCTGGGCCAGCGCGGCTGGGAGGCCC
TGAAGTACCTGGGCAGCCTGGTGCAGTACTGGGGCCTGGAGCTGAAGAAGAGCGCCATCAGCCTGCTGGACACCAT
CGCCATCGCCGTGGCCGAGGGCACCGACCGCATCATCGAGTTCATCCAGCGCATCTGCCGCGCCATCCGCAACATC
           gp160, gp41(2547)<--\
CCCCGCCGCATCCGCCAGGGCTTCGAGGCCGCCCTGCAGTAA

FIG. 3

Env_AF110975_C_BW_opt

```
--> signal peptide (1-72)                                                \/-->
ATGCGCGTGCGCGGCATCCTGCGCAGCTGGCAGCAGTGGTGGATCTGGGGCATCCTGGGCTTCTGGATCTGCAGCG
gp120/140/160 (72)
GCCTGGGCAACCTGTGGGTGACCGTGTACGACGGCGTGCCCGTGTGGCGCGAGGCCAGCACCACCCTGTTCTGCGC

CAGCGACGCCAAGGCCTACGAGAAGGAGGTGCACAACGTGTGGGCCACCCACGCCTGCGTGCCCACCGACCCCAAC

CCCCAGGAGATCGAGCTGGACAACGTGACCGAGAACTTCAACATGTGGAAGAACGACATGGTGGACCAGATGCACG

AGGACATCATCAGCCTGTGGGACCAGAGCCTGAAGCCCCGCGTGAAGCTGACCCCCCTGTGCGTGACCCTGAAGTG

CACCAACTACAGCACCAACTACAGCAACACCATGAACGCCACCAGCTACAACAACAACACCACCGAGGAGATCAAG

AACTGCACCTTCAACATGACCACCGAGCTGCGCGACAAGAAGCAGCAGGTGTACGCCCTGTTCTACAAGCTGGACA

TCGTGCCCCTGAACAGCAACAGCAGCGAGTACCGCCTGATCAACTGCAACACCAGCGCCATCACCCAGGCCTGCCC

CAAGGTGAGCTTCGACCCCATCCCCATCCACTACTGCGCCCCCGCCGGCTACGCCATCCTGAAGTGCAAGAACAAC

ACCAGCAACGGCACCGGCCCCTGCCAGAACGTGAGCACCGTGCAGTGCACCCACGGCATCAAGCCCGTGGTGAGCA

CCCCCCTGCTGCTGAACGGCAGCCTGGCCGAGGGCGGCGAGATCATCATCCGCAGCAAGAACCTGAGCAACAACGC

CTACACCATCATCGTGCACCTGAACGACAGCGTGGAGATCGTGTGCACCCGCCCCAACAACAACACCCGCAAGGGC

ATCCGCATCGGCCCCGGCCAGACCTTCTACGCCACCGAGAACATCATCGGCGACATCCGCCAGGCCCACTGCAACA

TCAGCGCCGGCGAGTGGAACAAGGCCGTGCAGCGCGTGAGCGCCAAGCTGCGCGAGCACTTCCCCAACAAGACCAT

CGAGTTCCAGCCCAGCAGCGGCGGCGACCTGGAGATCACCACCCACAGCTTCAACTGCCGCGGCGAGTTCTTCTAC

TGCAACACCAGCAAGCTGTTCAACAGCAGCTACAACGGCACCAGCTACCGCGGCACCGAGAGCAACAGCAGCATCA

TCACCCTGCCCTGCCGCATCAAGCAGATCATCGACATGTGGCAGAAGGTGGGCCGCGCCATCTACGCCCCCCCCAT

CGAGGGCAACATCACCTGCAGCAGCAGCATCACCGGCCTGCTGCTGGCCCGCGACGGCGGCCTGGACAACATCACC

ACCGAGATCTTCCGCCCCCAGGGCGGCGACATGAAGGACAACTGGCGCAACGAGCTGTACAAGTACAAGGTGGTGG
                                                     gp120(1509)<--\/-->(1510)gp41
AGATCAAGCCCCTGGGCGTGGCCCCCACCGAGGCCAAGCGCCGCGTGGTGGAGCGCGAGAAGCGCGCCGTGGGCAT

CGGCGCCGTGATCTTCGGCTTCCTGGGCGCCGCCGGCAGCAACATGGGCGCCGCCAGCATCACCCTGACCGCCCAG

GCCGCCAGCTGCTGAGCGGCATCGTGCAGCAGCAGAGCAACCTGCTGCGCGCCATCGAGGCCCAGCAGCACATGC

TGCAGCTGACCGTGTGGGGCATCAAGCAGCTGCAGGCCCGCGTGCTGGCCATCGAGCGCTACCTGAAGGACCAGCA

GCTGCTGGGCATCTGGGGCTGCAGCGGCAAGCTGATCTGCACCACCACCGTGCCCTGGAACAGCAGCTGGAGCAAC

AAGACCCAGGGCGAGATCTGGGAGAACATGACCTGGATGCAGTGGGACAAGGAGATCAGCAACTACACCGGCATCA

TCTACCGCCTGCTGGAGGAGAGCCAGAACCAGCAGGAGCAGAACGAGAAGGACCTGCTGGCCCTGGACAGCCGCAA
                   gp140(2022)<--\/
CAACCTGTGGAGCTGGTTCAACATCAGCAACTGGCTGTGGTACATCAAGATCTTCATCATGATCGTGGGCGGCCTG

ATCGGCCTGCGCATCATCTTCGCCGTGCTGAGCATCGTGAACCGCGTGCGCCAGGGCTACAGCCCCCTGAGCTTCC

AGACCCTGACCCCCAACCCCCGCGGCCTGGACCGCCTGGGCCGCATCGAGGAGGAGGGCGGCGAGCAGGACCGCGA

CCGCAGCATCCGCCTGGTGCAGGGCTTCCTGGCCCTGGCCTGGGACGACCTGCGCAGCCTGTGCCTGTTCAGCTAC

CACCGCCTGCGCGACCTGATCCTGGTGACCGCCCGCGTGGTGGAGCTGCTGGGCCGCAGCAGCCCCGCGGCCTGC

AGCGCGGCTGGGAGGCCCTGAAGTACCTGGGCAGCCTGGTGCAGTACTGGGGCCTGGAGCTGAAGAAGAGCGCCAC

CAGCCTGCTGGACAGCATCGCCATCGCCGTGGCCGAGGGCACCGACCGCATCATCGAGGTGATCCAGCGCATCTAC
               gp160, gp41(2565)<--\
CGCGCCTTCTGCAACATCCCCCGCCGCGTGCGCCAGGGCTTCGAGGCCGCCCTGCAGTAA
```

FIG. 4

Gag_AF110965_BW_opt
ATGGGCGCCCGCGCCAGCATCCTGCGCGGCGGCAAGCTGGACGCCTGGGAGCGCATCCGCCTGCGCCCCGG

CGGCAAGAAGTGCTACATGATGAAGCACCTGGTGTGGGCCAGCCGCGAGCTGGAGAAGTTCGCCCTGAACC

CCGGCCTGCTGGAGACCAGCGAGGGCTGCAAGCAGATCATCCGCCAGCTGCACCCCGCCCTGCAGACCGGC

AGCGAGGAGCTGAAGAGCCTGTTCAACACCGTGGCCACCCTGTACTGCGTGCACGAGAAGATCGAGGTGCG
                                                                  C

CGACACCAAGGAGGCCCTGGACAAGATCGAGGAGGAGCAGAACAAGAGCCAGCAGAAGATCCAGCAGGCCG

AGGCCGCCGACAAGGGCAAGGTGAGCCAGAACTACCCCATCGTGCAGAACCTGCAGGGCCAGATGGTGCAC

CAGGCCATCAGCCCCCGCACCCTGAACGCCTGGGTGAAGGTGATCGAGGAGAAGGCCTTCAGCCCCGAGGT

GATCCCCATGTTCACCGCCCTGAGCGAGGGCGCCACCCCCCAGGACCTGAACACCATGCTGAACACCGTGG
                                                       G   T

GCGGCCACCAGGCCGCCATGCAGATGCTGAAGGACACCATCAACGAGGAGGCCGCCGAGTGGGACCGCGTG

CACCCCGTGCACGCCGGCCCCATCGCCCCCGGCCAGATGCGCGAGCCCCGCGGCAGCGACATCGCCGGCAC

CACCAGCACCCTGCAGGAGCAGATCGCCTGGATGACCAGCAACCCCCCCATCCCCGTGGGCGACATCTACA

AGCGCTGGATCATCCTGGGCCTGAACAAGATCGTGCGCATGTACAGCCCCGTGAGCATCCTGGACATCAAG
    G                             G

CAGGGCCCCAAGGAGCCCTTCCGCGACTACGTGGACCGCTTCTTCAAGACCCTGCGCGCCGAGCAGAGCAC

CCAGGAGGTGAAGAACTGGATGACCGACACCCTGCTGGTGCAGAACGCCAACCCCGACTGCAAGACCATCC

TGCGCGCCCTGGGCCCCGGCGCCAGCCTGGAGGAGATGATGACCGCCTGCCAGGGCGTGGGCGGCCCCAGC
        T  C

CACAAGGCCCGCGTGCTGGCCGAGGCCATGAGCCAGGCCAACACCAGCGTGATGATGCAGAAGAGCAACTT
                     G

CAAGGGCCCCCGCCGCATCGTGAAGTGCTTCAACTGCGGCAAGGAGGGCCACATCGCCCGCAACTGCCGCG
              G    C

CCCCCCGCAAGAAGGGCTGCTGGAAGTGCGGCAAGGAGGGCCACCAGATGAAGGACTGCACCGAGCGCCAG

GCCAACTTCCTGGGCAAGATCTGGCCCAGCCACAAGGGCCGCCCCGGCAACTTCCTGCAGAGCCGCCCCGA

GCCCACCGCCCCCCCGCCGAGAGCTTCCGCTTCGAGGAGACCACCCCCGGCCAGAAGCAGGAGAGCAAGG

ACCGCGAGACCCTGACCAGCCTGAAGAGCCTGTTCGGCAACGACCCCCTGAGCCAGTAA

FIG. 5

Gag_AF110967_BW_opt
ATGGGCGCCCGCGCCAGCATCCTGCGCGGCGAGAAGCTGGACAAGTGGGAGAAGATCCGCCTGCGCCCCGG

CGGCAAGAAGCACTACATGCTGAAGCACCTGGTGTGGGCCAGCCGCGAGCTGGAGGGCTTCGCCCTGAACC

CCGGCCTGCTGGAGACCGCCGAGGGCTGCAAGCAGATCATGAAGCAGCTGCAGCCCGCCCTGCAGACCGGC

ACCGAGGAGCTGCGCAGCCTGTACAACACCGTGGCCACCCTGTACTGCGTGCACGCCGGCATCGAGGT[G]CG
                                                                   [C]

CGACACCAAGGAGGCCCTGGACAAGATCGAGGAGGAGCAGAACAA[AG]CCAGCAGAAGACCCAGCAGGCCA
                                             [TC]

AGGAGGCCGACGGCAAGGTGAGCCAGAACTACCCCATCGTGCAGAACCTGCAGGGCCAGATGGTGCACCAG

GCCATCAGCCCCCGCACCCTGAACGCCTGGGTGAAGGTGATCGAGGAGAAGGCCTTCAGCCCCGAGGTGAT

CCCCATGTTCACCGCCCTGAGCGAGGGCGCCACCCCCCAGGACCTGAACAC[CATGC]TGAACACCGTGGGCG
                                                    [ G   T]

GCCACCAGGCCGCCATGCAGATGCTGAAGGACACCATCAACGAGGAGGCCGCCGAGTGGGACCGCCTGCAC

CCCGTGCAGGCCGGCCCCGTGGCCCCCGGCCAGATGCGCGACCCCCGCGGCAGCGACATCGCCGGCGCCAC

CAGCACCCTGCAGGAGCAGATCGCCTGGATGACCAGCAACCCCCCCGTGCCCGTGGGCGACATCTACAAGC

G[C]TGGATCATCCTGGGCCTGAACAAGATCGTGCG[C]ATGTACAGCCCCGTGAGCATCCTGGACATCCGCCAG
 [G]                                 [G]

GGCCCCAAGGAGCCCTTCCGCGACTACGTGGACCGCTTCTTCAAGACCCTGCGCGCCGAGCAGGCCACCCA

GGACGTGAAGAACTGGATGACCGAGACCCTGCTGGTGCAGAACGCCAACCCCGACTGCAAGACCATCCTGC

GCG[CCTG]GCCCCGGCGCCACCCTGGAGGAGATGATGACCGCCTGCCAGGGCGTGGGCGGCCCCGGCCAC
   [T  C]

AAGGCCCGCGTGCTGGCCGAGG[C]ATGAGCCAGGCCAACAGCGTGAACATCATGATGCAGAAGAGCAACTT
                       [G]

CAAGGGCCCCCG[C]GCAACGT[G]AGTGCTTCAACTGCGGCAAGGAGGGCCACATCGCCAAGAACTGCCGCG
             [G]        [C]

CCCCCCGCAAGAAGGGCTGCTGGAAGTGCGGCAAGGAGGGCCACCAGATGAAGGACTGCACCGAGCGCCAG

GCCAACTTCCTGGGCAAGATCTGGCCCAGCCACAAGGGCCGCCCCGGCAACTTCCTGCAGAACCGCAGCGA

GCCCGCCGCCCCACCGTGCCCACCGCCCCCCCGCCGAGAGCTTCCGCTTCGAGGAGACCACCCCCGCCC

CCAAGCAGGAGCCCAAGGACCGCGAGCCCTACCGCGAGCCCCTGACCGCCCTGCGCAGCCTGTTCGGCAGC

GGCCCCCTGAGCCAGTAA

FIG. 6

PR975(+) (SEQ ID NO:30)

```
GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCCAGATCACCCTGTGGC
AGCGCCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGTACATGGACGACCTGTACGTGGGC
AGCGACCTGGAGATCGGCCAGCACCGCGCCAAGATCGAGGAGCTGCGCAAGCACCT
GCTGCGCTGGGGCTTCACCACCCCCGACAAGAAGCACCAGAAGGAGCCCCCCTTCCT
GTGGATGGGCTACGAGCTGCACCCCGACAAGTGGACCGTGCAGCCCATCGAGCTGCC
CGAGAAGGAGAGCTGGACCGTGAACGACATCCAGAAGCTGGTGGGCAAGCTGAACT
GGGCCAGCCAGATCTACCCCGGCATCAAGGTGCGCCAGCTGTGCAAGCTGCTGCGCG
GCGCCAAGGCCCTGACCGACATCGTGCCCCTGACCGAGGAGGCCGAGCTGGAGCTG
GCCGAGAACCGCGAGATCCTGCGCGAGCCCGTGCACGGCGTGTACTACGACCCCAG
CAAGGACCTGGTGGCCGAGATCCAGAAGCAGGGCCACGACCAGTGGACCTACCAGA
TCTACCAGGAGCCCTTCAAGAACCTGAAGACCGGCAAGTACGCCAAGATGCGCACC
GCCCACACCAACGACGTGAAGCAGCTGACCGAGGCCGTGCAGAAGATCGCCATGGA
GAGCATCGTGATCTGGGGCAAGACCCCCAAGTTCCGCCTGCCCATCCAGAAGGAGAC
CTGGGAGACCTGGTGGACCGACTACTGGCAGGCCACCTGGATCCCCGAGTGGGAGTT
CGTGAACACCCCCCCCCTGGTGAAGCTGTGGTACCAGCTGGAGAAGGAGCCCATCAT
CGGCGCCGAGACCTTCTACGTGGACGGCGCCGCCAACCGCGAGACCAAGATCGGCA
AGGCCGGCTACGTGACCGACCGGGGCCGGCAGAAGATCGTGAGCCTGACCGAGACC
ACCAACCAGAAGACCGAGCTGCAGGCCATCCAGCTGGCCCTGCAGGACAGCGGCAG
CGAGGTGAACATCGTGACCGACAGCCAGTACGCCCTGGGCATCATCCAGGCCCAGCC
CGACAAGAGCGAGAGCGAGCTGGTGAACCAGATCATCGAGCAGCTGATCAAGAAGG
AGAAGGTGTACCTGAGCTGGGTGCCCGCCCACAAGGGCATCGGCGGCAACGAGCAG
ATCGACAAGCTGGTGAGCAAGGGCATCCGCAAGGTGCTGTTCCTGGACGGCATCGAT
GGCGGCATCGTGATCTACCAGTACATGGACGACCTGTACGTGGGCAGCGGCGGCCCT
AGGATCGATTAAAAGCTTCCCGGGGCTAGCACCGGTGAATTC
```

FIG. 8

PR975YM (SEQ ID NO:31)
GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCCAGATCACCCTGTGGC
AGCGCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGGCCCCCCTGTACGTGGGCAGCGAC
CTGGAGATCGGCCAGCACCGCGCCAAGATCGAGGAGCTGCGCAAGCACCTGCTGCG
CTGGGGCTTCACCACCCCCGACAAGAAGCACCAGAAGGAGCCCCCCTTCCTGTGGAT
GGGCTACGAGCTGCACCCCGACAAGTGGACCGTGCAGCCCATCGAGCTGCCCGAGA
AGGAGAGCTGGACCGTGAACGACATCCAGAAGCTGGTGGGCAAGCTGAACTGGGCC
AGCCAGATCTACCCCGGCATCAAGGTGCGCCAGCTGTGCAAGCTGCTGCGCGGCGCC
AAGGCCCTGACCGACATCGTGCCCCTGACCGAGGAGGCCGAGCTGGAGCTGGCCGA
GAACCGCGAGATCCTGCGCGAGCCCGTGCACGGCGTGTACTACGACCCCAGCAAGG
ACCTGGTGGCCGAGATCCAGAAGCAGGGCCACGACCAGTGGACCTACCAGATCTAC
CAGGAGCCCTTCAAGAACCTGAAGACCGGCAAGTACGCCAAGATGCGCACCGCCCA
CACCAACGACGTGAAGCAGCTGACCGAGGCCGTGCAGAAGATCGCCATGGAGAGCA
TCGTGATCTGGGGCAAGACCCCCAAGTTCCGCCTGCCCATCCAGAAGGAGACCTGGG
AGACCTGGTGGACCGACTACTGGCAGGCCACCTGGATCCCCGAGTGGGAGTTCGTGA
ACACCCCCCCCCTGGTGAAGCTGTGGTACCAGCTGGAGAAGGAGCCCATCATCGGCG
CCGAGACCTTCTACGTGGACGGCGCCGCCAACCGCGAGACCAAGATCGGCAAGGCC
GGCTACGTGACCGACCGGGGCCGGCAGAAGATCGTGAGCCTGACCGAGACCACCAA
CCAGAAGACCGAGCTGCAGGCCATCCAGCTGGCCCTGCAGGACAGCGGCAGCGAGG
TGAACATCGTGACCGACAGCCAGTACGCCCTGGGCATCATCCAGGCCCAGCCCGACA
AGAGCGAGAGCGAGCTGGTGAACCAGATCATCGAGCAGCTGATCAAGAAGGAGAAG
GTGTACCTGAGCTGGGTGCCCGCCCACAAGGGCATCGGCGGCAACGAGCAGATCGA
CAAGCTGGTGAGCAAGGGCATCCGCAAGGTGCTGTTCCTGGACGGCATCGATGGCG
GCATCGTGATCTACCAGTACATGGACGACCTGTACGTGGGCAGCGGCGGCCCTAGGA
TCGATTAAAAGCTTCCCGGGGCTAGCACCGGTGAATTC

FIG. 9

PR975YMWM (SEQ ID NO:32)

GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCCAGATCACCCTGTGGC
AGCGCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGGCCCCCCTGTACGTGGGCAGCGAC
CTGGAGATCGGCCAGCACCGCGCCAAGATCGAGGAGCTGCGCAAGCACCTGCTGCG
CTGGGGCTTCACCACCCCCGACAAGAAGCACCAGAAGGAGCCCCCCTTCCTGCCCAT
CGAGCTGCACCCCGACAAGTGGACCGTGCAGCCCATCGAGCTGCCCGAGAAGGAGA
GCTGGACCGTGAACGACATCCAGAAGCTGGTGGGCAAGCTGAACTGGGCCAGCCAG
ATCTACCCCGGCATCAAGGTGCGCCAGCTGTGCAAGCTGCTGCGCGGCGCCAAGGCC
CTGACCGACATCGTGCCCCTGACCGAGGAGGCCGAGCTGGAGCTGGCCGAGAACCG
CGAGATCCTGCGCGAGCCCGTGCACGGCGTGTACTACGACCCCAGCAAGGACCTGGT
GGCCGAGATCCAGAAGCAGGGCCACGACCAGTGGACCTACCAGATCTACCAGGAGC
CCTTCAAGAACCTGAAGACCGGCAAGTACGCCAAGATGCGCACCGCCCACACCAAC
GACGTGAAGCAGCTGACCGAGGCCGTGCAGAAGATCGCCATGGAGAGCATCGTGAT
CTGGGGCAAGACCCCCAAGTTCCGCCTGCCCATCCAGAAGGAGACCTGGGAGACCT
GGTGGACCGACTACTGGCAGGCCACCTGGATCCCCGAGTGGGAGTTCGTGAACACCC
CCCCCCTGGTGAAGCTGTGGTACCAGCTGGAGAAGGAGCCCATCATCGGCGCCGAG
ACCTTCTACGTGGACGGCGCCGCCAACCGCGAGACCAAGATCGGCAAGGCCGGCTA
CGTGACCGACCGGGGCCGGCAGAAGATCGTGAGCCTGACCGAGACCACCAACCAGA
AGACCGAGCTGCAGGCCATCCAGCTGGCCCTGCAGGACAGCGGCAGCGAGGTGAAC
ATCGTGACCGACAGCCAGTACGCCCTGGGCATCATCCAGGCCCAGCCCGACAAGAG
CGAGAGCGAGCTGGTGAACCAGATCATCGAGCAGCTGATCAAGAAGGAGAAGGTGT
ACCTGAGCTGGGTGCCCGCCCACAAGGGCATCGGCGGCAACGAGCAGATCGACAAG
CTGGTGAGCAAGGGCATCCGCAAGGTGCTGTTCCTGGACGGCATCGATGGCGGCATC
GTGATCTACCAGTACATGGACGACCTGTACGTGGGCAGCGGCGGCCCTAGGATCGAT
TAAAAGCTTCCCGGGGCTAGCACCGGTGAATTC

FIG. 10

8_5_ZA  (SEQ ID NO:33)

```
   1 TGGAAGGGTT AATTTACTCC AAGAAAAGGC AAGAAATCCT TGATTTGTGG GTCTATCACA
  61 CACAAGGCTT CTTCCCTGAT TGGCAAAACT ACACACCGGG GCCAGGGGTC AGATATCCAC
 121 TGACCTTTGG ATGGTGCTAC AAGCTAGTGC CAGTTGACCC AGGGGAGGTG GAAGAGGCCA
 181 ACGGAGGAGA AGACAACTGT TTGCTACACC CTATGAGCCA ACATGGAGCA GAGGATGAAG
 241 ATAGAGAAGT ATTAAAGTGG AAGTTTGACA GCCTCCTAGC ACGCAGACAC ATGGCCCGCG
 301 AGCTACATCC GGAGTATTAC AAAGACTGCT GACACAGAAG GGACTTTCCG CCTGGGACTT
 361 TCCACTGGGG CGTTCCGGGA GGTGTGGTCT GGGCGGGACT TGGGAGTGGT CAACCCTCAG
 421 ATGCTGCATA TAAGCAGCTG CTTTTCGCCT GTACTGGGTC TCTCTCGGTA GACCAGATCT
 481 GAGCCTGGGA GCCCTCTGGC TATCTAGGGA ACCCACTGCT TAAGCCTCAA TAAAGCTTGC
 541 CTTGAGTGCT TTAAGTAGTG TGTGCCCATC TGTTGTGTGA CTCTGGTAAC TAGAGATCCC
 601 TCAGACCCTT TGTGGTAGTG TGGAAAATCT CTAGCAGTGG CGCCCGAACA GGGACCAGAA
 661 AGTGAAAGTG AGACCAGAGG AGATCTCTCG ACGCAGGACT CGGCTTGCTG AAGTGCACAC
 721 GGCAAGAGGC GAGAGGGGCG GCTGGTGAGT ACGCCAATTT TACTTGACTA GCGGAGGCTA
 781 GAAGGAGAGA GATGGGTGCG AGAGCGTCAA TATTAAGCGG CGGAAAATTA GATAAATGGG
 841 AAAGAATTAG GTTAAGGCCA GGGGGAAAGA AACATTATAT GTTAAAACAT CTAGTATGGG
 901 CAAGCAGGGA GCTGGAAAGA TTTGCACTTA ACCCTGGCCT GTTAGAAACA TCAGAAGGCT
 961 GTAAACAAAT AATAAAACAG CTACAACCAG CTCTTCAGAC AGGAACAGAG GAACTTAGAT
1021 CATTATTCAA CACAGTAGCA ACTCTCTATT GTGTACATAA AGGGATAGAG GTACGAGACA
1081 CCAAGGAAGC CTTAGACAAG ATAGAGGAAG AACAAAACAA ATGTCAGCAA AAAGCACAAC
1141 AGGCAAAAGC AGCTGACGAA AAGGTCAGTC AAAATTATCC TATAGTACAG AATGCCCAAG
1201 GGCAAATGGT ACACCAAGCT ATATCACCTA GAACATTGAA TGCATGGATA AAAGTAATAG
1261 AGGAAAAGGC TTTCAATCCA GAGGAAATAC CCATGTTTAC AGCATTATCA GAAGGAGCCA
1321 CCCCACAAGA TTTAAACACA ATGTTAAATA CAGTGGGGGG ACATCAAGCA GCCATGCAAA
1381 TGTTAAAAGA TACCATCAAT GAGGAGGCTG CAGAATGGGA TAGGACACAT CCAGTACATG
1441 CAGGGCCTGT TGCACCAGGC CAGATGAGAG AACCAAGGGG AAGTGACATA GCAGGAACTA
1501 CTAGTACCCT TCAGGAACAA ATAGCATGGA TGACAAGTAA TCCACCTATT CCAGTAGAAG
1561 ACATCTATAA AAGATGGATA ATTCTGGGGT TAAATAAAAT AGTAAGAATG TATAGCCCTG
1621 TTAGCATTTT GGACATAAAA CAAGGGCCAA AGAACCCTT TAGAGACTAT GTAGACCGGT
1681 TCTTTAAAAC CTTAAGAGCT GAACAAGCTA CACAAGATGT AAAGAATTGG ATGACAGACA
1741 CCTTGTTGGT CCAAAATGCG AACCCAGATT GTAAGACCAT TTTAAGAGCA TTAGGACCAG
1801 GGGCCTCATT AGAAGAAATG ATGACAGCAT GTCAGGGAGT GGGAGGACCT AGCCATAAAG
1861 CAAGAGTGTT GGCTGAGGCA ATGAGCCAAG CAAACAGTAA CATACTAGTG CAGAGAAGCA
1921 ATTTTAAAGG CTCTAACAGA ATTATTAAAT GTTTCAACTG TGGCAAAGTA GGGCACATAG
1981 CCAGAAATTG CAGGGCCCCT AGGAAAAAGG GCTGTTGGAA ATGTGGACAG GAAGGACACC
2041 AAATGAAAGA CTGTACTGAG AGGCAGGCTA ATTTTTTAGG GAAAATTTGG CCTTCCCACA
2101 AGGGGAGGCC AGGGAATTTC CTCCAGAACA GACCAGAGCC AACAGCCCCA CCAGCAGAAC
2161 CAACAGCCCC ACCAGCAGAG AGCTTCAGGT TCGAGGAGAC AACCCCCGTG CCGAGGAAGG
2221 AGAAAGAGAG GGAACCTTTA ACTTCCCTCA AATCACTCTT TGGCAGCGAC CCCTTGTCTC
2281 AATAAAAGTA GAGGGCCAGA TAAAGGAGGC TCTCTTAGAC ACAGGAGCAG ATGATACAGT
2341 ATTAGAAGAA ATAGATTTGC CAGGGAAATG GAAACCAAAA ATGATAGGGG GAATTGGAGG
2401 TTTTATCAAA GTAAGACAGT ATGATCAAAT ACTTATAGAA ATTTGTGGAA AAAAGGCTAT
2461 AGGTACAGTA TTAGTAGGGC CTACACCAGT CAACATAATT GGAAGAAATC TGTTAACTCA
2521 GCTTGGATGC ACACTAAATT TTCCAATTAG TCCTATTGAA ACTGTACCAG TAAAATTAAA
2581 ACCAGGAATG GATGGCCCAA AGGTCAAACA ATGGCCATTG ACAGAAGAAA AAATAAAAGC
2641 ATTAACAGCA ATTTGTGAGG AAATGGAGAA GGAAGGAAAA ATTACAAAAA TTGGGCCTGA
2701 TAATCCATAT AACACTCCAG TATTTGCCAT AAAAAAGAAG GACAGTACTA AGTGGAGAAA
2761 ATTAGTAGAT TTCAGGGAAC TCAATAAAAG AACTCAAGAC TTTTGGGAAG TTCAATTAGG
2821 AATACCACAC CCAGCAGGAT TAAAAAAGAA AAAATCAGTG ACAGTGCTAG ATGTGGGGGA
2881 TGCATATTTT TCAGTTCCTT TAGATGAAAG CTTCAGGAAA TATACTGCAT TCACCATACC
```

FIG. 11A

```
2941 TAGTATAAAC AATGAAACAC CAGGGATTAG ATATCAATAT AATGTGCTGC CACAGGGATG
3001 GAAAGGATCA CCAGCAATAT TCCAGAGTAG CATGACAAAA ATCTTAGAGC CCTTCAGAGC
3061 AAAAAATCCA GACATAGTTA TCTATCAATA TATGGATGAC TTGTATGTAG GATCTGACTT
3121 AGAAATAGGG CAACATAGAG CAAAAATAGA AGAGTTAAGG GAACATTTAT TGAAATGGGG
3181 ATTTACAACA CCAGACAAGA AACATCAAAA AGAACCCCCA TTTCTTTGGA TGGGGTATGA
3241 ACTCCATCCT GACAAATGGA CAGTACAACC TATACTGCTG CCAGAAAAGG ATAGTTGGAC
3301 TGTCAATGAT ATACAGAAGT TAGTGGGAAA ATTAAACTGG GCAAGTCAGA TTTACCCAGG
3361 GATTAAAGTA AGGCAACTCT GTAAACTCCT CAGGGGGGCC AAAGCACTAA CAGACATAGT
3421 ACCACTAACT GAAGAAGCAG AATTAGAATT GGCAGAGAAC AGGGAAATTT TAAGAGAACC
3481 AGTACATGGA GTATATTATG ATCCATCAAA AGACTTGATA GCTGAAATAC AGAAACAGGG
3541 GCATGAACAA TGGACATATC AAATTTATCA AGAACCATTT AAAAATCTGA AAACAGGGAA
3601 GTATGCAAAA ATGAGGACTA CCCACACTAA TGATGTAAAA CAGTTAACAG AGGCAGTGCA
3661 AAAAATAGCC ATGGAAAGCA TAGTAATATG GGGAAAGACT CCTAAATTTA GACTACCCAT
3721 CCAAAAAGAA ACATGGGAGA CATGGTGGAC AGACTATTGG CAAGCCACCT GGATCCCTGA
3781 GTGGGAGTTT GTTAATACCC CTCCCCTAGT AAAATTATGG TACCAACTAG AAAAAGATCC
3841 CATAGCAGGA GTAGAAACTT TCTATGTAGA TGGAGCAACT AATAGGGAAG CTAAAATAGG
3901 AAAAGCAGGG TATGTTACTG ACAGAGGAAG GCAGAAAATT GTTACTCTAA CTAACACAAC
3961 AAATCAGAAG ACTGAGTTAC AAGCAATTCA GCTAGCTCTG CAGGATTCAG GATCAGAAGT
4021 AAACATAGTA ACAGACTCAC AGTATGCATT AGGAATCATT CAAGCACAAC CAGATAAGAG
4081 TGACTCAGAG ATATTTAACC AAATAATAGA ACAGTTAATA AACAAGGAAA GAATCTACCT
4141 GTCATGGGTA CCAGCACATA AAGGAATTGG GGGAAATGAA CAAGTAGATA AATTAGTAAG
4201 TAAGGGAATT AGGAAAGTGT TGTTTCTAGA TGGAATAGAT AAAGCTCAAG AAGAGCATGA
4261 AAGGTACCAC AGCAATTGGA GAGCAATGGC TAATGAGTTT AATCTGCCAC CCATAGTAGC
4321 AAAAGAAATA GTAGCTAGCT GTGATAAATG TCAGCTAAAA GGGGAAGCCA TACATGGACA
4381 AGTCGACTGT AGTCCAGGGA TATGGCAATT AGATTGTACC CATTTAGAGG GAAAAATCAT
4441 CCTGGTAGCA GTCCATGTAG CTAGTGGCTA CATGGAAGCA GAGGTTATCC CAGCAGAAAC
4501 AGGACAAGAA ACAGCATATT TTATATTAAA ATTAGCAGGA AGATGGCCAG TCAAAGTAAT
4561 ACATACAGAC AATGGCAGTA ATTTTACCAG TACTGCAGTT AAGGCAGCCT GTTGGTGGGC
4621 AGGTATCCAA CAGGAATTTG GAATTCCCTA CAATCCCCAA AGTCAGGGAG TGGTAGAATC
4681 CATGAATAAA GAATTAAAGA AAATAATAGG ACAAGTAAGA GATCAAGCTG AGCACCTTAA
4741 GACAGCAGTA CAAATGGCAG TATTCATTCA CAATTTTAAA AGAAAAGGGG GAATTGGGGG
4801 GTACAGTGCA GGGGAAAGAA TAATAGACAT AATAGCAACA GACATACAAA CTAAAGAATT
4861 ACAAAAACAA ATTATAAGAA TTCAAAATTT TCGGGTTTAT TACAGAGACA GCAGAGACCC
4921 TATTTGGAAA GGACCAGCCG AACTACTCTG GAAAGGTGAA GGGGTAGTAG TAATAGAAGA
4981 TAAAGGTGAC ATAAAGGTAG TACCAAGGAG GAAAGCAAAA ATCATTAGAG ATTATGGAAA
5041 ACAGATGGCA GGTGCTGATT GTGTGGCAGG TGGACAGGAT GAAGATTAGA GCATGGAATA
5101 GTTTAGTAAA GCACCATATG TATATATCAA GGAGAGCTAG TGGATGGGTC TACAGACATC
5161 ATTTTGAAAG CAGACATCCA AAAGTAAGTT CAGAAGTACA TATCCCATTA GGGGATGCTA
5221 GATTAGTAAT AAAAACATAT TGGGGTTTGC AGACAGGAGA AAGAGATTGG CATTTGGGTC
5281 ATGGAGTCTC CATAGAATGG AGACTGAGAG AATACAGCAC ACAAGTAGAC CCTGACCTGG
5341 CAGACCAGCT AATTCACATG CATTATTTTG ATTGTTTTAC AGAATCTGCC ATAAGACAAG
5401 CCATATTAGG ACACATAGTT TTTCCTAGGT GTGACTATCA AGCAGGACAT AAGAAGGTAG
5461 GATCTCTGCA ATACTTGGCA CTGACAGCAT TGATAAAACC AAAAAAGAGA AAGCCACCTC
5521 TGCCTAGTGT TAGAAAATTA GTAGAGGATA GATGGAACGA CCCCCAGAAG ACCAGGGGCC
5581 GCAGAGGGAA CCATACAATG AATGGACACT AGAGATTCTA GAAGAACTCA AGCAGGAAGC
5641 TGTCAGACAC TTTCCTAGAC CATGGCTCCA TAGCTTAGGA CAATATATCT ATGAAACCTA
5701 TGGGGATACT TGGACGGGAG TTGAAGCTAT AATAAGAGTA CTGCAACAAC TACTGTTCAT
5761 TCATTTCAGA ATTGGATGCC AACATAGCAG AATAGGCATC TTGCGACAGA GAAGAGCAAG
5821 AAATGGAGCC AGTAGATCCT AAACTAAAGC CCTGGAACCA TCCAGGAAGC CAACCTAAAA
5881 CAGCTTGTAA TAATTGCTTT TGCAAACACT GTAGCTATCA TTGTCTAGTT TGCTTTCAGA
```

FIG. 11B

```
5941 CAAAAGGTTT AGGCATTTCC TATGGCAGGA AGAAGCGGAG ACAGCGACGA AGCGCTCCTC
6001 CAAGTGGTGA AGATCATCAA AATCCTCTAT CAAAGCAGTA AGTACACATA GTAGATGTAA
6061 TGGTAAGTTT AAGTTTATTT AAAGGAGTAG ATTATAGATT AGGAGTAGGA GCATTGATAG
6121 TAGCACTAAT CATAGCAATA ATAGTGTGGA CCATAGCATA TATAGAATAT AGGAAATTGG
6181 TAAGACAAAA GAAAATAGAC TGGTTAATTA AAAGAATTAG GGAAAGAGCA GAAGACAGTG
6241 GCAATGAGAG TGATGGGGAC ACAGAAGAAT TGTCAACAAT GGTGGATATG GGGCATCTTA
6301 GGCTTCTGGA TGCTAATGAT TTGTAACACG GAGGACTTGT GGGTCACAGT CTACTATGGG
6361 GTACCTGTGT GGAGAGAAGC AAAAACTACT CTATTCTGTG CATCAGATGC TAAAGCATAT
6421 GAGACAGAAG TGCATAATGT CTGGGCTACA CATGCTTGTG TACCCACAGA CCCCAACCCA
6481 CAAGAAATAG TTTTGGGAAA TGTAACAGAA AATTTTAATA TGTGGAAAAA TAACATGGCA
6541 GATCAGATGC ATGAGGATAT AATCAGTTTA TGGGATCAAA GCCTAAAGCC ATGTGTAAAG
6601 TTGACCCCAC TCTGTGTCAC TTTAAACTGT ACAGATACAA ATGTTACAGG TAATAGAACT
6661 GTTACAGGTA ATACAAATGA TACCAATATT GCAAATGCTA CATATAAGTA TGAAGAAATG
6721 AAAAATTGCT CTTTCAATGC AACCACAGAA TTAAGAGATA AGAAACATAA AGAGTATGCA
6781 CTCTTTTATA AACTTGATAT AGTACCACTT AATGAAAATA GTAACAACTT TACATATAGA
6841 TTAATAAATT GCAATACCTC AACCATAACA CAAGCCTGTC CAAAGGTCTC TTTTGACCCG
6901 ATTCCTATAC ATTACTGTGC TCCAGCTGAT TATGCGATTC TAAAGTGTAA TAATAAGACA
6961 TTCAATGGGA CAGGACCATG TTATAATGTC AGCACAGTAC AATGTACACA TGGAATTAAG
7021 CCAGTGGTAT CAACTCAACT ACTGTTAAAT GGTAGTCTAG CAGAAGAAGG GATAATAATT
7081 AGATCTGAAA ATTTGACAGA GAATACCAAA ACAATAATAG TACATCTTAA TGAATCTGTA
7141 GAGATTAATT GTACAAGGCC CAACAATAAT ACAAGGAAAA GTGTAAGGAT AGGACCAGGA
7201 CAAGCATTCT ATGCAACAAA TGACGTAATA GGAAACATAA GACAAGCACA TTGTAACATT
7261 AGTACAGATA GATGGAATAA AACTTTACAA CAGGTAATGA AAAAATTAGG AGAGCATTTC
7321 CCTAATAAAA CAATAAAATT TGAACCACAT GCAGGAGGGG ATCTAGAAAT TACAATGCAT
7381 AGCTTTAATT GTAGAGGAGA ATTTTTCTAT TGCAATACAT CAAACCTGTT TAATAGTACA
7441 TACTACCCTA AGAATGGTAC ATACAAATAC AATGGTAATT CAAGCTTACC CATCACACTC
7501 CAATGCAAAA TAAAACAAAT TGTACGCATG TGGCAAGGGG TAGGACAAGC AATGTATGCC
7561 CCTCCCATTG CAGGAAACAT AACATGTAGA TCAAACATCA CAGGAATACT ATTGACACGT
7621 GATGGGGGAT TTAACAACAC AAACAACGAC ACAGAGGAGA CATTCAGACC TGGAGGAGGA
7681 GATATGAGGG ATAACTGGAG AAGTGAATTA TATAAATATA AAGTGGTAGA AATTAAGCCA
7741 TTGGGAATAG CACCCACTAA GGCAAAAAGA AGAGTGGTGC AGAGAAAAAA AAGAGCAGTG
7801 GGAATAGGAG CTGTGTTCCT TGGGTTCTTG GGAGCAGCAG GAAGCACTAT GGGCGCAGCG
7861 TCAATAACGC TGACGGTACA GGCCAGACAA CTGTTGTCTG GTATAGTGCA ACAGCAAAGC
7921 AATTTGCTGA AGGCTATAGA GGCGCAACAG CATATGTTGC AACTCACAGT CTGGGGCATT
7981 AAGCAGCTCC AGGCGAGAGT CCTGGCTATA GAAAGATACC TAAAGGATCA ACAGCTCCTA
8041 GGGATTTGGG GCTGCTCTGG AAGACTCATC TGCACCACTG CTGTGCCTTG GAACTCCAGT
8101 TGGAGTAATA AATCTGAAGC AGATATTTGG GATAACATGA CTTGGATGCA GTGGGATAGA
8161 GAAATTAATA ATTACACAGA AACAATATTC AGGTTGCTTG AAGACTCGCA AAACCAGCAG
8221 GAAAAGAATG AAAAAGATTT ATTAGAATTG GACAAGTGGA ATAATCTGTG GAATTGGTTT
8281 GACATATCAA ACTGGCTGTG GTATATAAAA ATATTCATAA TGATAGTAGG AGGCTTGATA
8341 GGTTTAAGAA TAATTTTTGC TGTGCTCTCT ATAGTGAATA GAGTTAGGCA GGGATACTCA
8401 CCTTTGTCAT TTCAGACCCT TACCCCAAGC CCGAGGGGAC TCGACAGGCT CGGAGGAATC
8461 GAAGAAGAAG GTGGAGAGCA AGACAGAGAC AGATCCATAC GATTGGTGAG CGGATTCTTG
8521 TCGCTTGCCT GGGACGATCT GCGGAGCCTG TGCCTCTTCA GCTACCACCG CTTGAGAGAC
8581 TTCATATTAA TTGCAGTGAG GCAGTGGAA CTTCTGGGAC ACAGCAGTCT CAGGGGACTA
8641 CAGAGGGGGT GGGAGATCCT TAAGTATCTG GAAGTCTTG TGCAGTATTG GGTCTAGAG
8701 CTAAAAAAGA GTGCTATTAG TCCGCTTGAT ACCATAGCAA TAGCAGTAGC TGAAGGAACA
8761 GATAGGATTA TAGAATTGGT ACAAAGAATT TGTAGAGCTA TCCTCAACAT ACCTAGGAGA
8821 ATAAGACAGG GCTTTGAAGC AGCTTTGCTA TAAAATGGGA GGCAAGTGGT CAAAACGCAG
8881 CATAGTTGGA TGGCCTGCAG TAAGAGAAAG AATGAGAAGA ACTGAGCCAG CAGCAGAGGG
8941 AGTAGGAGCA GCGTCTCAAG ACTTAGATAG ACATGGGGCA CTTACAAGCA GCAACACACC
```

FIG. 11C

```
9001 TGCTACTAAT GAAGCTTGTG CCTGGCTGCA AGCACAAGAG GAGGACGGAG ATGTAGGCTT
9061 TCCAGTCAGA CCTCAGGTAC CTTTAAGACC AATGACTTAT AAGAGTGCAG TAGATCTCAG
9121 CTTCTTTTTA AAAGAAAAGG GGGGACTGGA AGGGTTAATT TACTCTAGGA AAAGGCAAGA
9181 AATCCTTGAT TTGTGGGTCT ATAACACACA AGGCTTCTTC CCTGATTGGC AAAACTACAC
9241 ATCGGGGCCA GGGGTCCGAT TCCCACTGAC CTTTGGATGG TGCTTCAAGC TAGTACCAGT
9301 TGACCCAAGG GAGGTGAAAG AGGCCAATGA AGGAGAAGAC AACTGTTTGC TACACCCTAT
9361 GAGCCAACAT GGAGCAGAGG ATGAAGATAG AGAAGTATTA AAGTGGAAGT TTGACAGCCT
9421 TCTAGCACAC AGACACATGG CCCGCGAGCT ACATCCGGAG TATTACAAAG ACTGCTGACA
9481 CAGAAGGGAC TTTCCGCCTG GGACTTTCCA CTGGGGCGTT CCGGGAGGTG TGGTCTGGGC
9541 GGGACTTGGG AGTGGTCACC CTCAGATGCT GCATATAAGC AGCTGCTTTT CGCTTGTACT
9601 GGGTCTCTCT CGGTAGACCA GATCTGAGCC TGGGAGCTCT CTGGCTATCT AGGGAACCCA
9661 CTGCTTAGGC CTCAATAAAG CTTGCCTTGA GTGCTCTAAG TAGTGTGTGC CCATCTGTTG
9721 TGTGACTCTG GTAACTAGAG ATCCCTCAGA CCCTTTGTGG TAGTGTGGAA AATCTCTAGC
9781 A
```

FIG. 11D

SEQ ID NO:34

GCTGAGGCAATGAGCCAAGCAACCAGCGCAAACATACTGATGCAGAGAAGCAATTT
CAAAGGCCCTAAAAGAATTATTAAATGTTTCAACTGTGGCAAGGAAGGGCACATAG
CTAGAAATTGTAGGGCCCCTAGGAAAAAAGGCTGTTGGAAATGTGGAAAGGAAGGA
CACCAAATGAAAGACTGTACTGAGAGGCAGGCTAA

FIG. 12

975Pol wt until 6aa Int: (SEQ ID NO:35)
TTTTTTAGGGAAGATTTGGCCTTCCCACAAGGGAAGGCCAGGGAATTTCCTTCAGAA
CAGAACAGAGCCAACAGCCCCACCAGCAGAGAGCTTCAAGTTCGAGGAGACAACCC
CCGCTCCGAAGCAGGAGCCGAAAGACAGGGAACCCTTAATTTCCCTCAAATCACTCT
TTGGCAGCGACCCCTTGTCTCAATAAAAGTAGGGGGTCAAATAAAGGAGGCTCTCTT
AGACACAGGAGCTGATGATACAGTATTAGAAGAAATGAGTTTGCCAGGAAAATGGA
AACCAAAAATGATAGGAGGAATTGGAGGTTTTATCAAAGTAAGACAGTATGATCAA
ATACTTATAGAAATTTGTGGAAAAAAGGCTATAGGTACAGTATTAATAGGACCTACA
CCTGTCAACATAATTGGAAGGAATATGTTGACTCAGCTTGGATGCACACTAAATTTT
CCAATTAGTCCCATTGAAACTGTGCCAGTAAAATTAAAGCCAGGAATGGATGGCCCA
AAGGTTAAACAATGGCCATTGACAGAAGAGAAAATAAAAGCATTAACAGCAATTTG
TGAAGAAATGGAGAAAGAAGGAAAAATTACAAAAATTGGGCCTGAAAATCCATATA
ACACTCCAGTATTTGCCATAAAAAAGAAGGACAGTACTAAGTGGAGAAAGTTAGTA
GATTTCAGGGAACTTAATAAAAGAACTCAAGACTTTTGGGAAGTTCAATTAGGAATA
CCACACCCAGCAGGGTTAAAAAAGAAAAAATCAGTGACAGTACTGGATGTGGGGGA
TGCATATTTTTCAGTTCCTTTAGATGAGGACTTCAGGAAATATACTGCATTCACCATA
CCTAGTATAAACAATGAAACACCAGGGATTAGATATCAATATAATGTGCTTCCACAG
GGATGGAAAGGATCACCATCAATATTCCAGAGTAGCATGACAAAAATCTTAGAGCC
CTTTAGAGCAAGAAATCCAGAAATAGTCATCTATCAATATATGGATGACTTGTATGT
AGGATCTGACTTAGAAATAGGGCAACATAGAGCAAAAATAGAGGAGTTAAGAAAAC
ATCTGTTAAGGTGGGGATTTACCACACCGGACAAGAAACATCAGAAAGAACCCCCA
TTTCTTTGGATGGGGTATGAACTCCATCCTGACAAATGGACAGTACAGCCTATAGAG
TTGCCAGAAAAGGAAAGCTGGACTGTCAATGATATACAGAAGTTAGTGGGAAAATT
AAATTGGGCCAGTCAGATTTACCCAGGAATTAAAGTAAGGCAACTTTGTAAACTCCT
TAGGGGGGCCAAAGCACTAACAGATATAGTACCACTAACTGAAGAAGCAGAATTAG
AATTGGCAGAGAACAGGGAAATTCTAAGAGAACCAGTACATGGAGTATATTATGAC
CCATCAAAAGACTTGGTAGCTGAAATACAGAAACAGGGGCATGACCAATGGACATA
TCAAATTTACCAAGAACCATTCAAAAACCTGAAAACAGGGAAGTATGCAAAAATGA
GGACTGCCCACACTAATGATGTAAAACAGTTAACAGAGGCAGTGCAAAAAATAGCT
ATGGAAAGCATAGTAATATGGGGAAAGACTCCTAAATTTAGACTACCCATCCAAAA
AGAAACATGGGAGACATGGTGGACAGACTATTGGCAAGCCACCTGGATTCCTGAGT
GGGAGTTTGTTAATACCCCTCCCTTAGTAAAATTATGGTACCAGCTAGAGAAAGAAC
CCATAATAGGAGCAGAAACTTTCTATGTAGATGGAGCAGCTAATAGGGAAACTAAA
ATAGGAAAAGCAGGGTATGTTACTGACAGAGGAAGGCAGAAAATTGTTTCTCTAAC
AGAAACAACAAATCAGAAGACTGAATTACAAGCAATTCAGCTAGCTTTGCAAGATTC
AGGATCAGAAGTAAACATAGTAACAGACTCACAGTATGCATTAGGAATCATTCAAG
CACAACCAGATAAGAGTGAATCAGAGTTAGTCAACCAAATAATAGAACAATTAATA
AAAAAGGAAAAGGTCTACCTGTCATGGGTACCAGCACATAAAGGAATTGGAGGAAA
TGAACAAATAGATAAATTAGTAAGTAAGGGAATCAGGAAAGTGCTGTTTCTAGATG
GAATAGAT

FIG. 13

SEQ ID NO:36

GGCGGCATCGTGATCTACCAGTACATGGACGACCTGTACGTGGGCAGCGGCG
GC

FIG. 14

SEQ ID NO: 37

GGIVIYQYMDDLYVGSGG

FIG. 15

12_5/1ZA (SEQ ID NO:45)

```
TGGAAGGGTTAATTTACTCCAGGAAAAGGCAAGAGATCCTTGATTTATGGGTCTATC
ACACACAAGGCTACTTCCCTGATTGGCAAAACTACACACCGGGACCAGGGGTCAGA
TATCCACTGACCTTTGGATGGTGCTTCAAGCTAGTGCCAGTTGACCCAAGGGAAGTA
GAAGAGGCCAACGGAGGAGAAGACAACTGTTTGCTACACCCTATGAGCCAGTATGG
AATGGATGATGAACACAAAGAAGTGTTACAGTGGAAGTTTGACAGCAGCCTAGCAC
GCAGACACCTGGCCCGCGAGCTACATCCGGATTATTACAAAGACTGCTGACACAGA
AGGGACTTTCCGCCTGGGACTTTCCACTGGGGCGTTCCAGGGGGAGTGGTCTGGGCG
GGACTGGGAGTGGCCAGCCCTCAGATGCTGCATATAAGCAGCGGCTTTTCGCCTGTA
CTGGGTCTCTCTAGGTAGACCAGATCCGAGCCTGGGAGCTCTCTGTCTATCTGGGGA
ACCCACTGCTTAGGCCTCAATAAAGCTTGCCTTGAGTGCTCTAAGTAGTGTGTGCCC
ATCTGTTGTGTGACTCTGGTAACTCTGGTAACTAGAGATCCCTCAGACCCTTTGTGGT
AGTGTGGAAAATCTCTAGCAGTGGCGCCCGAACAGGGACTTGAAAGCGAAAGTGAG
ACCAGAGAAGATCTCTCGACGCAGGACTCGGCTTGCTGAAGTGCACTCGGCAAGAG
GCGAGGGGGGCGACTGGTGAGTACGCCAAAATTTTTTTTGACTAGCGGAGGCTAGA
AGGAGAGAGATGGGTGCGAGAGCGTCAATATTAAGAGGGGGAAAATTAGACAAAT
GGGAAAAAATTAGGTTACGGCCAGGGGGAGAAAACACTATATGCTAAAACACCTA
GTATGGGCAAGCAGAGAGCTGGAAAGATTTGCAGTTAACCCTGGCCTTTTAGAGAC
ATCAGACGGATGTAGAC AAATAATAAAACAGCTACAACCAGCTCTTCAGA
CAGGAACAGAGGAAATTAGATCATTATTTAACACAGTAGCAACTCTCTATTGTGTAC
ATAAAGGGATAGATGTACGAGACACCAAGGAAGCCTTAGACAAGATAGAGGAGGA
ACAAAACAAATGTCAGCAAAAAACACAGCAGGCGGAAGCGGCTGACAAAAAGGTC
AGTCAAAATTATCCTATAGTGCAGAACCTCCAAGGGCAAATGGTACACCAGGCCAT
ATCACCTAGAACCTTGAATGCATGGGTAAAAGTAATAGAGGAGAAGGCTTTTAGCC
CAGAGGTAATACCCATGTTTACAGCATTATCAGAAGGAGCCACCCCACAAGATTTA
AACACCATGTTAAATACAGTGGGGGGACATCAAGCAGCCATGCAAATGTTAAAAG
ATACCATCAATGAGGAGGCTGCAGAATGGGATAGGTTACATCCAGTACATGCAGGG
CCTGTTGCACCAGGCCAGATGAGAGAACCAAGGGGAAGTGACATAGCAGGAACTA
CTAGTACCCTTCAAGAACAAATAGCATGGATGACAAGTAACCCACCTATCCCAGTA
GGGGACATCTATAAAAGGTGGATAATTCTGGGGTTAAATAAAATAGTAAGAATGTA
CAGCCCTGTCAGCATTTTAGACATAAAACAAGGACCAAAGGAACCCTTTAGAGACT
ATGTAGACCGGTTCTTCAAAACTTTAAGAGCTGAACAATCTACACAAGAGGTAAAA
AATTGGATGACAGACACCTTGTTAGTCCAAAATGCGAACCCAGATTGTAAGACCATT
TTAAGAGCATTAGGACCAGGGGCTTCATTAGAAGAAATGATGACAGCATGTCAGGG
AGTGGGAGGACCTAGCCACAAAGCAAGAGTTTTGGCTGAGGCAATGAGCCAAGCAA
ACAATACAAGTGTAATGATACAGAAAAGCAATTTTAAAGGCCCTAGAAGAGCTGTT
AAATGTTTCAACTGTGGCAGGGAAGGGCACATAGCCAGGAATTGCAGGGCCCCTAG
GAAAAGGGGCTGTTGGAAATGTGGAAAGGAAGGACACCAAATGAAAGACTGTACT
GAGAGGCAGGCTAATTTTTTAGGGAAAATTTGGCCTTCCCACAAGGGGAGGCCAGG
GAATTTCCTTCAGAGCAGACCAGAGCCAACAGCCCCACCACTAGAACCAACAGCCC
CACCAGCAGAGAGCTTCAAGTTCAAGGAGACTCCGAAGCAGGAGCCGAAAGACAG
GGAACCTTTAACTTCCCTCAAATCACTCTTTGGCAGCGACCCCTTGTCTCAATAAAA
```

FIG. 16A

```
GTAGCGGGCCAAACAAAGGAGGCTCTTTTAGATACAGGAGCAGATGATACAGTACT
AGAAGAAATAAACTTGCCAGGAAAATGGAAACCAAAAATGATAGGAGGAATTGGA
GGTTTTATCAAAGTAAGACAGTATGATCAAATACTTATAGAAATTTGTGGAAAAAGG
GCTATAGGTACAGTATTAGTAGGACCTACACCTGTCAACATAATTGGAAGAAATCTG
TTGACTCAGCTTGGATGCACACTAAATTTTCCAATTAGCCCCATTGAAACTGTACCA
GTAAAATTAAAGCCAGGAATGGATGGCCCAAAGGTTAAACAATGGCCATTGACAGA
AGAAAAAATAAAAGCATTAACAGAAATTTGTGAGGAAATGGAGAAGGAAGGAAAA
ATTACAAAAATTGGGCCTGAAAATCCATATAACACTCCAGTATTTGCCATAAAGAAG
AAGGACAGTACAAAGTGGAGAAAATTAGTAGATTTCAGGGAACTCAATAAAAGAAC
TCAAGACTTTTGGGAAGTCCAATTAGGAATACCACACCCAGCAGGGTTAAAAAAGA
AAAAATCAGTGACAGTACTGGATGTGGGAGATGCATATTTTTCAGTCCCTTTAGATG
AGAGCTTCAGAAAATATACTGCATTCACCATACCTAGTATAAACAATGAAACACCA
GGGATTAGATATCAATATAATGTTCTTCCACAGGGATGGAAAGGATCACCAGCAA
TATTCCAGAGTAGCATGACAAGAATCTTAGAGCCCTTTAGAACACAAAACCCAGAA
GTAGTTATCTATCAATATATGGATGACTTATATGTAGGATCTGACTTAGAAATAGGG
CAACATAGAGCAAAAATAGAGGAGTTAAGAGGACACCTATTGAAATGGGGATTTAC
CACACCAGACAAGAAACATCAGAAAGAACCCCCATTTCTTTGGATGGGGTATGAAC
TCCATCCTGACAAATGGACAGTACAGCCTATACAGCTGCCAGAAAAGGAGAGCTGG
ACTGTCAATGATATACAGAAGTTAGTGGGAAAGTTAAACTGGGCAAGTCAGATTTA
CCCAGGGATTAAAGTAAGGCAACTGTGTAAACTCCTTAGGGGAGCCAAAGCACTAA
CAGACATAGTGCCACTGACTGAAGAAGCAGAATTAGAATTGGCTGAGAACAGGGA
AATTCTAAAAGAACCAGTACATGGAGTATATTATGACCCATCAAAAGATTTAATAG
CTGAAATACAGAAACAGGGGAATGACCAATGGACATATCAAATTTACCAAGAACC
ATTTAAAAATCTGAGAACAGGAAAGTATGCAAAAATGAGGACTGCCCACACTAATG
ATGTGAAACAGTTAGCAGAGGCAGTGCAAAAGATAACCCAGGAAAGCATAGTAATA
TGGGGAAAAACTCCTAAATTTAGACTACCCATCCCAAAAGAAACATGGGAGACATG
GTGGTCAGACTATTGGCAAGCCACCTGGATTCCTGAGTGGGAGTTTGTCAATACCCC
TCCCCTAGTAAAATTGTGGTACCAGCTGGAAAAAGAACCCATAGTAGGGGCAGAAA
CTTTCTATGTAGATGGAGCAGCCAATAGGGAAACTAAAATAGGAAAAGCAGGGTAT
GTCACTGACAAAGGAAGGCAGAAAGTTGTTTCCTTCACTGAAACAACAAATCAGAA
GACTGAATTACAAGCAATTCAGCTAGCTTTGCAGGATTCAGGGCCAGAAGTAAACA
TAGTAACAGACTCACAGTATGCATTAGGAATCATTCAAGCACAACCAGATAAGAGT
GAATCAGAATTAGTCAGTCAAATAATAGAACAGTTGATAAAAAAGGAAAAAGTCTA
CCTATCATGGGTACCAGCACATAAAGGAATTGGAGGAAATGAACAAGTAGACAAAT
TAGTAAGTAGTGGAATCAGAAAAGTACTGTTTCTAGATGGAATAGATAAAGCTCAA
GAAGAGCATGAAAAATATCACAGCAATTGGAGAGCAATGGCTAGTGAGTTTAATCT
GCCACCCATAGTAGCAAAGGAAATAGTAGCCAGCTGTGATAAATGTCAGCTAAAAG
GGGAAGCCATGCATGGACAAGTCGACTGTAGTCCAGGAATATGGCAATTAGACTGT
ACACATTTAGAAGGAAAAATCATCCTAGTAGCAGTCCATGTAGCCAGTGGCTACAT
GGAAGCAGAGGTTATCCCAGCAGAAACAGGACAAGAAACAGCATACTTTATACTAA
AATTAGCAGGAAGATGGCCAGTCAAAGTAATACATACAGATAATGGCAGTAATTTC
ACCAGTACCGCAGTTAAGGCAGCCTGTTGGTGGGCAGATATCCAACGGGAATTTGG
AATTCCCTACAATCCCCAAAGTCAAGGAGTAGTAGAATCCATGAATAAAGAATTAA
```

FIG. 16B

```
AGAAAATCATAGGGCAAGTAAGAGATCAAGCTGAGCACCTTAAGACAGCAGTACAA
ATGGCAGTATTCATTCACAATTTTAAAAGAAAAGGGGGGATTGGGGGGTACAGTGC
AGGGGAGAGAATAATAGACATAATAGCATCAGACATACAAACTAAAGAATTACAAA
AACAAATTATAAAAATTCAAAATTTTCGGGTTTATTACAGAGACAGCAGAGACCCTA
TTTGGAAAGGACCAGCCAAACTACTCTGGAAAGGTGAAGGGGCAGTAGTAATACAA
GATAATAGTGATATAAAGGTAGTACCAAGAAGGAAAGCAAAAATCATTAAGGACTA
TGGAAAACAGATGGCAGGTGCTGATTGTGTGGCAGGTAGACAGGATGAAGATTAGA
ACATGGCACAGTTTAGTAAAGCACCATATGTATGTTTCGAGGAGAGCTGATGGATGG
TTCTACAGACATCATTATGAAAGCAGACACCCAAAAGTAAGTTCAGAAGTACACAT
CCCATTAGGAGATGCCAGGTTAGTAATAAAAACATATTGGGGTCTGCAGACAGGAG
AAAGAGCTTGGCATTTGGGTCACGGAGTCTCCATAGAATGGAGATTGAGAAGATAT
AGCACACAAGTAGACCCTGACCTGACAGACCAACTAATTCATATGCATTATTTTGAT
TGTTTTGCAGAATCTGCCATAAGGAAAGCCATACTAGGACAGATAGTTAGCCCTAA
GTGTGACTATCAAGCAGGACATAACAAGGTAGGATCTCTACAATACTTGGCACTGA
CAGCATTGATAAAACCAAAAAAGATAAAGCCACCTCTGCCTAGTGTTAGGAAATTA
GTAGAGGATAGATGGAACAAGCCCCAGAAGACCAGGGGCCGCAGAGGGAACCATA
CAATGAATGGACACTAGAGCTTTTAGAAGAACTCAAGCAGGAAGCTGTCAGACACT
TTCCTAGACCATGGCTCCATAACTTAGGACAACATATCTATGAAACCTATGGAGATA
CTTGGACAGGAGTTGAAGCAATAATAAGAATCCTGCAACAATTACTGTTTATTCATT
TCAGGATTGGGTGCCATCATAGCAGAATAGGCATTTTGCGACAGAGAAGAGCAAGA
AATGGAGCCAATAGATCCTAACCTAGAACCCTGGAACCATCCAGGAAGTCAGCCTA
AAACTGCTTGTAATGGGTGTTACTGTAAACGTTGCAGCTATCATTGTCTAGTTTGCTT
TCAGAAAAAAGGCTTAGGCATTTACTATGGCAGGAAGAAGCGGAGACAGCGACGAA
GCGCTCCTCCAAGCAATAAAGATCATCAAGATCCTCTACCAAAGCAGTAAGTACCG
AATAGTATATGTAATGTTAGATTTAACTGCAAGAATAGATTCTAGATTAGGAATAGG
AGCATTGATAGTAGCACTAATCATAGCAATAATAGTGTGGACCATAGTATATATAG
AATATAGGAAATTGGTAAGGCAAAGGAAAATAGACTGGTTAGTTAAAAGGATTAGG
GAAAGAGCAGAAGACAGTGGCAATGAGAGCGAGGGGGATACTGAAGAATTATCGA
CACTGGTGGATATGGGGCATCTTAGGCTTTTGGATGCTAATGATGTGTAATGTGAA
GGGCTTGTGGGTCACAGTCTACTACGGGGTACCTGTGGGAGAGAAGCAAAAACT
ACTCTATTTTGTGCATCAGATGCTAAAGCATATGAGAAAGAAGTGCATAATGTCTG
GGCTACACATGCCTGTGTACCCACAGACCCCAACCCACAAGAAGTGATTTTGGGC
AATGTAACAGAAAATTTTAACATGTGGAAAAATGACATGGTGGATCAGATGCAGG
AAGATATAATCAGTTTATGGGATCAAAGCCTTAAGCCATGTGTAAAATGACCCCA
CTCTGTGTCACTTTAAACTGTACAAATGCAACTGTTAACTACAATAATACCTCTAAA
GACATGAAAAATTGCTCTTTCTATGTAACCACAGAATTAAGAGATAAGAAAAAGAA
AGAAAATGCACTTTTTTATAGACTTGATATAGTACCACTTAATAATAGGAAGAATGG
GAATATTAACAACTATAGATTAATAAATTGTAATACCTCAGCCATAACACAAGCCTG
TCCAAAAGTCTCGTTTGACCCAATTCCTATACATTATTGTGCTCCAGCTGGTTATGCG
CCTCTAAAATGTAATAATAAGAAATTCAATGGAATAGGACCATGCGATAATGTCAG
CACAGTACAATGTACACATGGAATTAAGCCAGTGGTATCAACTCAATTACTGTTAAA
TGGTAGCCTAGCAGAAGAAGAGATAATAATTAGATCTGAAAATCTGACAAACAATG
TCAAAACAATAATAGTACATCTTAATGAATCTATAGAGATTAAATGTACAAGACC
```

FIG. 16C

```
TGGCAATAATACAAGAAAGAGTGTGAGAATAGGACCAGGACAAGCATTCTATGCA
ACAGGAGACATAATAGGAGATATAAGACAAGCACATTGTAACATTAGTAAAAATGA
ATGGAATACAACTTTACAAAGGGTAAGTCAAAAATTACAAGAACTCTTCCCTAATA
GTACAGGGATAAAATTTGCACCACACTCAGGAGGGGACCTAGAAATTACTACACAT
AGCTTTAATTGTGGAGGAGAATTTTTCTATTGCAATACAACAGACCTGTTTAATAGT
ACATACAGTAATGGTACATGCACTAATGGTACATGCATGTCTAATAATACAGAGCG
CATCACACTCCAATGCAGAATAAAACAAATTATAAACATGTGGCAGGAGGTAGGAC
GAGCAATGTATGCCCCTCCCATTGCAGGAAACATAACATGTAGATCAAATATTACA
GGACTACTATTAACACGTGATGGAGGAGATAATAATACTGAAACAGAGACATTCAG
ACCTGGAGGAGGAGACATGAGGGACAATTGGAGAAGTGAATTATATAAATACAAG
GTGGTAGAAATTAAACCATTAGGAGTAGCACCCACTGCTGCAAAAAGGAGAGTGGT
GGAGAGAGAAAAAAGAGCAGTAGGAATAGGAGCTGTGTTCCTTGGGTTCTTGGGAG
CAGCAGGAAGCACTATGGGCGCAGCATCAATAACGCTGACGGTACAGGCCAGACAA
TTATTGTCTGGTATAGTGCAACAGCAAAGTAATTTGCTGAGGGCTATAGAGGCGCAA
CAGCATATGTTGCAACTCACGGTCTGGGGCATTAAGCAGCTCCAGGCAAGAGTCCTG
GCTATAGAGAGATACCTACAGGATCAACAGCTCCTAGGACTGTGGGGCTGCTCTGG
AAAACTCATCTGCACCACTAATGTGCTTTGGAACTCTAGTTGGAGTAATAAAACTCA
AAGTGATATTTGGGATAACATGACCTGGATGCAGTGGGATAGGGAAATTAGTAATT
ACACAAACACAATATACAGGTTGCTTGAAGACTCGCAAAGCCAGCAGGAAAGAAA
TGAAAAAGATTTACTAGCATTGGACAGGTGGAACAATCTGTGGAATTGGTTTAGCAT
AACAAATTGGCTGTGGTATATAAAAATATTCATAATGATAGTAGGAGGCTTGATAG
GTTTAAGAATAATTTTTGCTGTGCTCTCTCTAGTAAATAGAGTTAGGCAGGGATACT
CACCCTTGTCATTGCAGACCCTTATCCCAAACCCGAGGGGACCCGACAGGCTCGGA
GGAATCGAAGAAGAAGGTGGAGAGCAAGACAGCAGCAGATCCATTCGATTAGTGA
GCGGATTCTTGACACTTGCCTGGGACGACCTACGAAGCCTGTGCCTCTTCTGCTACC
ACCGATTGAGAGACTTCATATTAATTGTAGTGAGAGCAGTGGAACTTCTGGGACAC
AGTAGTCTCAGGGGACTGCAGAGGGGGTGGGGAACCCTTAAGTATTTGGGGAGTCT
TGTGCAATATTGGGGTCTAGAGTTAAAAAAGAGTGCTATTAATCTGCTTGATACTAT
AGCAATAGCAGTAGCTGAAGGAACAGATAGGATTCTAGAATTCATACAAAACCTTT
GTAGAGGTATCCGCAACGTACCTAGAAGAATAAGACAGGGCTTCGAAGCAGCTTTG
CAATAAAATGGGGGGCAAGTGGTCAAAAAGCAGTATAATTGGATGGCCTGAAGTAA
GAGAAAGAATCAGACGAACTAGGTCAGCAGCAGAGGGAGTAGGATCAGCGTCTCA
AGACTTAGAGAAACATGGGGCACTTACAACCAGCAACACAGCCCACAACAATGCTG
CTTGCGCCTGGCTGGAAGCGCAAGAGGAGGAAGGAGAAGTAGGCTTTCCAGTCAGA
CCTCAGGTACCTTTAAGACCAATGACTTATAAAGCAGCAATAGATCTCAGCTTCTTT
TTAAAAGAAAAGGGGGGACTGGAAGGGTTAATTTACTCCAAGAAAAGGCAAGAGAT
CCTTGATTTGTGGGTTTATAACACACAAGGCTTCTTCCCTGATTGGCAAAACTACAC
ACCGGGACCAGGGGTCAGATTTCCACTGACCTTTGGATGGTACTTCAAGCTAGAGCC
AGTCGATCCAAGGGAAGTAGAAGAGGCCAATGAAGGAGAAAACAACTGTTTACTAC
ACCCTATGAGCCAGCATGGAATGGAGGATGAAGACAGAGAAGTATTAAGATGGAAG
TTTGACAGTACGCTAGCACGCAGACACATGGCCCGCGAGCTACATCCGGAGTATTAC
AAAGACTGCTGACACAGAAGGGACTTTCCGCTGGGACTTTCCACTGGGGCGTTCCAG
GAGGTGTGGTCTGGGCGGGACAGGGGAGTGGTCAGCCCTGAGATGCTGCATATAAG
CAGCTGCTTTTCGCCTGTACTGGGTCTCTCTAGGTAGACCAGATCTGAGCCCGGGAG
```

FIG. 16D

CTCTCTGGCTATCTAGGGAACCCACTGCTTAAGCCTCAATAAAGCTTGCCTTGAGTG
CCTTGAGTAGTGTGTGCCCGTCTGTTGTGTGACTCTGGTAACTAGAGATCCCTCAGA
CCACTTGTGGTAGTGTGGAAAATCTCTAGCA

FIG. 16E

› # POLYNUCLEOTIDES ENCODING ANTIGENIC HIV TYPE C POLYPEPTIDES, POLYPEPTIDES AND USES THEREOF

CROSS-REFERENCE TO RELATED APPLICATIONS

This application is a continuation-in-part of U.S. Ser. No. 09/475,704, filed Dec. 30, 1999 now abandoned, which in turn is related to provisional patent applications Ser. Nos. 60/114,495, filed Dec. 31, 1998 and 60/152,195, filed Sep. 1, 1999, from which priority is claimed under 35 U.S.C. §119 (e)(1) and which applications are incorporated herein by reference in their entireties.

TECHNICAL FIELD

Polynucleotides encoding antigenic Type C HIV Gag-, Env- and/or Pol-containing polypeptides are described, as are uses of these polynucleotides and polypeptide products in immunogenic compositions. Also described are polynucleotide sequences from South African variants of HIV Type C.

BACKGROUND OF THE INVENTION

Acquired immune deficiency syndrome (AIDS) is recognized as one of the greatest health threats facing modern medicine. There is, as yet, no cure for this disease. In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225:840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2 See, e.g., Guyader et al. (1987) Nature 326:662-669; Brun-Vezinet et al. (1986) Science 233: 343-346; Clavel et al. (1986) Nature 324:691-695.

A great deal of information has been gathered about the HIV virus, however, to date an effective vaccine has not been identified. Several targets for vaccine development have been examined including the env and Gag gene products encoded by HIV. Gag gene products include, but are not limited to, Gag-polymerase and Gag-protease. Env gene products include, but are not limited to, monomeric gp120 polypeptides, oligomeric gp140 polypeptides and gp160 polypeptides.

Haas, et al., (Current Biology 6(3):315-324, 1996) suggested that selective codon usage by HIV-1 appeared to account for a substantial fraction of the inefficiency of viral protein synthesis. Andre, et al., (J. Virol. 72(2):1497-1503, 1998) described an increased immune response elicited by DNA vaccination employing a synthetic gp120 sequence with optimized codon usage. Schneider, et al., (*J. Virol.* 71(7): 4892-4903, 1997) discuss inactivation of inhibitory (or instability) elements (INS) located within the coding sequences of the Gag and Gag-protease coding sequences.

The Gag proteins of HIV-1 are necessary for the assembly of virus-like particles. HIV-1 Gag proteins are involved in many stages of the life cycle of the virus including, assembly, virion maturation after particle release, and early post-entry steps in virus replication. The roles of HIV-1 Gag proteins are numerous and complex (Freed, E. O., *Virology* 251:1-15, 1998).

Wolf, et al., (PCT International Application, WO 96/30523, published 3 Oct. 1996; European Patent Application, Publication No. 0 449 116 A1, published 2 Oct. 1991) have described the use of altered pr55 Gag of HIV-1 to act as a non-infectious retroviral-like particulate carrier, in particular, for the presentation of immunologically important epitopes. Wang, et al., (*Virology* 200:524-534, 1994) describe a system to study assembly of HIV Gag-β-galactosidase fusion proteins into virions. They describe the construction of sequences encoding HIV Gag-β-galactosidase fusion proteins, the expression of such sequences in the presence of HIV Gag proteins, and assembly of these proteins into virus particles.

Shiver, et al., (PCT International Application, WO 98/34640, published 13 Aug. 1998) described altering HIV-1 (CAM1) Gag coding sequences to produce synthetic DNA molecules encoding HIV Gag and modifications of HIV Gag. The codons of the synthetic molecules were codons preferred by a projected host cell.

Recently, use of HIV Env polypeptides in immunogenic compositions has been described. (see, U.S. Pat. No. 5,846,546 to Hurwitz et al., issued Dec. 8, 1998, describing immunogenic compositions comprising a mixture of at least four different recombinant virus that each express a different HIV env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HIV-1 isolate containing the sequence GPGR. There remains a need for antigenic HIV polypeptides, particularly Type C isolates.

SUMMARY OF THE INVENTION

The present invention relates to synthetic expression cassettes encoding HIV Type C Pol (e.g., p6pol, prot, p66RT, p15RNAseH, p31Int)-containing polypeptides and to polynucleotides of novel HIV Type C variants. In addition, the present invention also relates to improved expression of HIV Type C Pol- and/or Gag-containing polypeptides and production of virus-like particles, as well as, Env-containing polypeptides. Synthetic expression cassettes encoding the HIV polypeptides (e.g., Gag-, pol-, prot-, reverse transcriptase, integrase and/or Env-containing polypeptides) are described, as are uses of the expression cassettes.

One aspect of the present invention relates to expression cassettes and polynucleotides contained therein. In one embodiment, an expression cassette comprises a polynucleotide sequence encoding one or more Pol-containing polypeptides, wherein the polynucleotide sequence comprises a sequence having at least about 85%, preferably about 90%, more preferably about 95%, and more preferably about 98% sequence (and any integers between these values) identity to the sequences taught in the present specification. The polynucleotide sequences encoding Pol-containing polypeptides include, but are not limited to, those shown in SEQ ID NO:30, SEQ ID NO:31 and SEQ ID NO:32.

The polynucleotides encoding the Pol-containing polypeptides of the present invention may also include sequences encoding additional polypeptides. Such additional polynucleotides encoding polypeptides may include, for example, coding sequences for other viral proteins (e.g., hepatitis B or C or other HIV proteins, such as, polynucleotide sequences encoding an HIV Gag polypeptide, polynucleotide sequences encoding an HIV Env polypeptide and/or polynucleotides encoding one or more of vif, vpr, tat, rev, vpu and nef); cytokines or other transgenes. In one embodiment, the sequence encoding the HIV Pol polypeptide(s) can be modified by deletions of coding regions corresponding to reverse transcriptase and integrase. Such deletions in the polymerase polypeptide can also be made such that the polynucleotide sequence preserves T-helper cell and CTL epitopes. Other antigens of interest may be inserted into the polymerase as well.

In another embodiment, an expression cassette comprises a polynucleotide sequence encoding a polypeptide including an HIV Gag-containing polypeptide, wherein the polynucleotide sequence encoding the Gag polypeptide comprises a sequence having at least about 85%, preferably about 90%, more preferably about 95%, and most preferably about 98% sequence identity to the sequences taught in the present specification. The polynucleotide sequences encoding Gag-containing polypeptides include, but are not limited to, the following polynucleotides: nucleotides 844-903 of FIG. 1 (a Gag major homology region) (SEQ ID NO:1); nucleotides 841-900 of FIG. 2 (a Gag major homology region) (SEQ ID NO:2); the sequence presented as FIG. 1 (SEQ ID NO:3); and the sequence presented as FIG. 2 (SEQ ID NO:4). As noted above, the polynucleotides encoding the Gag-containing polypeptides of the present invention may also include sequences encoding additional polypeptides.

In another embodiment, an expression cassette comprises a polynucleotide sequence encoding a polypeptide including an HIV Env-containing polypeptide, wherein the polynucleotide sequence encoding the Env polypeptide comprises a sequence having at least about 85%, preferably about 90%, more preferably about 95%, and most preferably about 98% sequence identity to the sequences taught in the present specification. The polynucleotide sequences encoding Env-containing polypeptides include, but are not limited to, the following polynucleotides: nucleotides 1213-1353 of FIG. 3 (SEQ ID NO:5) (an Env common region); nucleotides 82-1512 of FIG. 3 (SEQ ID NO:6) (a gp120 polypeptide); nucleotides 82-2025 of FIG. 3 (SEQ ID NO:7) (a gp140 polypeptide); nucleotides 82-2547 of FIG. 3 (SEQ ID NO:8) (a gp160 polypeptide); nucleotides 1-2547 of FIG. 3 (SEQ ID NO:9) (a gp160 polypeptide with signal sequence); nucleotides 1513-2547 of FIG. 3 (SEQ ID NO:10) (a gp41 polypeptide); nucleotides 1210-1353 of FIG. 4 (SEQ ID NO:11) (an Env common region); nucleotides 73-1509 of FIG. 4 (SEQ ID NO:12) (a gp120 polypeptide); nucleotides 73-2022 of FIG. 4 (SEQ ID NO:13) (a gp140 polypeptide); nucleotides 73-2565 of FIG. 4 (SEQ ID NO:14) (a gp160 polypeptide); nucleotides 1-2565 of FIG. 4 (SEQ ID NO:15) (a gp160 polypeptide with signal sequence); and nucleotides 1510-2565 of FIG. 4 (SEQ ID NO:16) (a gp41 polypeptide).

The present invention further includes recombinant expression systems for use in selected host cells, wherein the recombinant expression systems employ one or more of the polynucleotides and expression cassettes of the present invention. In such systems, the polynucleotide sequences are operably linked to control elements compatible with expression in the selected host cell. Numerous expression control elements are known to those in the art, including, but not limited to, the following: transcription promoters, transcription enhancer elements, transcription termination signals, polyadenylation sequences, sequences for optimization of initiation of translation, and translation termination sequences. Exemplary transcription promoters include, but are not limited to those derived from CMV, CMV+intron A, SV40, RSV, HIV-Ltr, MMLV-ltr, and metallothionein.

In another aspect the invention includes cells comprising the expression cassettes of the present invention where the polynucleotide sequence (e.g., encoding a Pol, Env- and/or Gag-containing polypeptide) is operably linked to control elements compatible with expression in the selected cell. In one embodiment such cells are mammalian cells. Exemplary mammalian cells include, but are not limited to, BHK, VER0, HT1080, 293, RD, COS-7, and CHO cells. Other cells, cell types, tissue types, etc., that may be useful in the practice of the present invention include, but are not limited to, those obtained from the following: insects (e.g., *Trichoplusia ni* (Tn5) and Sf9), bacteria, yeast, plants, antigen presenting cells (e.g., macrophage, monocytes, dendritic cells, B-cells, T-cells, stem cells, and progenitor cells thereof), primary cells, immortalized cells, tumor-derived cells.

In a further aspect, the present invention includes compositions for generating an immunological response, where the composition typically comprises at least one of the expression cassettes of the present invention and may, for example, contain combinations of expression cassettes (such as one or more expression cassettes carrying a Pol-polypeptide-encoding polynucleotide, one or more expression cassettes carrying a Gag-polypeptide-encoding polynucleotide and/or one or more expression cassettes carrying an Env-polypeptide-encoding polynucleotide). Such compositions may further contain an adjuvant or adjuvants. The compositions may also contain one or more Pol-containing polypeptides, one or more Gag-containing polypeptides and/or one or more Env-containing polypeptides. The Pol-containing polypetpides, Gag-containing polypeptides and/or Env-containing polypeptides may correspond to the polypeptides encoded by the expression cassette(s) in the composition, or, the Pol-containing polypeptides, Gag-containing polypeptides and/or Env-containing polypeptides may be different from those encoded by the expression cassettes. An example of the polynucleotide in the expression cassette encoding the same polypeptide as is being provided in the composition is as follows: the polynucleotide in the expression cassette encodes the Gag-polypeptide of FIG. 1 (SEQ ID NO:3), and the polypeptide is the polypeptide encoded by the sequence shown in FIG. 1 (SEQ ID NO:17). An example of the polynucleotide in the expression cassette encoding a different polypeptide as is being provided in the composition is as follows: an expression cassette having a polynucleotide encoding a Gag-polymerase polypeptide, and the polypeptide provided in the composition may be a Gag and/or Gag-protease polypeptide. In compositions containing both expression cassettes (or polynucleotides of the present invention) and polypeptides, the Pol, Env and Gag expression cassettes of the present invention can be mixed and/or matched with Pol, Env-containing and Gag-containing polypeptides described herein.

In another aspect the present invention includes methods of immunization of a subject. In the method any of the above described compositions are into the subject under conditions that are compatible with expression of the expression cassette in the subject. In one embodiment, the expression cassettes (or polynucleotides of the present invention) can be introduced using a gene delivery vector. The gene delivery vector can, for example, be a non-viral vector or a viral vector. Exemplary viral vectors include, but are not limited to Sindbis-virus derived vectors, retroviral vectors, and lentiviral vectors. Compositions useful for generating an immunological response can also be delivered using a particulate carrier.

Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

In a further aspect, the invention includes methods of generating an immune response in a subject, wherein the expression cassettes or polynucleotides of the present invention are expressed in a suitable cell to provide for the expression of the Pol-, Env- and/or Gag-containing polypeptides encoded by the polynucleotides of the present invention. The polypeptide(s) are then isolated (e.g., substantially purified) and administered to the subject in an amount sufficient to elicit an immune response.

The invention further includes methods of generating an immune response in a subject, where cells of a subject are transfected with any of the above-described expression cassettes or polynucleotides of the present invention, under conditions that permit the expression of a selected polynucleotide and production of a polypeptide of interest (e.g., encoded by any expression cassette of the present invention). By this method an immunological response to the polypeptide is elicited in the subject. Transfection of the cells may be performed ex vivo and the transfected cells are reintroduced into the subject. Alternately, or in addition, the cells may be transfected in vivo in the subject. The immune response may be humoral and/or cell-mediated (cellular). In a further embodiment, this method may also include administration of an Env-, Pol- and/or Gag-containing polypeptide before, concurrently with, and/or after introduction of the expression cassette into the subject.

Further embodiments of the present invention include purified polynucleotides. Exemplary polynucleotide sequences encoding Gag-containing polypeptides include, but are not limited to, the following polynucleotides: nucleotides 844-903 of FIG. 1 (SEQ ID NO:1) (a Gag major homology region); nucleotides 841-900 of FIG. 2 (SEQ ID NO:2) (a Gag major homology region); the sequence presented as FIG. 1 (SEQ ID NO:3); and the sequence presented as FIG. 2 (SEQ ID NO:4). Exemplary polynucleotide sequences encoding Env-containing polypeptides include, but are not limited to, the following polynucleotides: nucleotides 1213-1353 of FIG. 3 (SEQ ID NO:5) (an Env common region); nucleotides 82-1512 of FIG. 3 (SEQ ID NO:6) (a gp120 polypeptide); nucleotides 82-2025 of FIG. 3 (SEQ ID NO:7) (a gp140 polypeptide); nucleotides 82-2547 of FIG. 3 (SEQ ID NO:8) (a gp160 polypeptide); nucleotides 1-2547 of FIG. 3 (SEQ ID NO:9) (a gp160 polypeptide with signal sequence); nucleotides 1513-2547 of FIG. 3 (SEQ ID NO:10) (a gp41 polypeptide); nucleotides 1210-1353 of FIG. 4 (SEQ ID NO:11) (an Env common region); nucleotides 73-1509 of FIG. 4 (SEQ ID NO:12) (a gp120 polypeptide); nucleotides 73-2022 of FIG. 4 (SEQ ID NO:13) (a gp140 polypeptide); nucleotides 73-2565 of FIG. 4 (SEQ ID NO:14) (a gp160 polypeptide); nucleotides 1-2565 of FIG. 4 (SEQ ID NO:15) (a gp160 polypeptide with signal sequence); and nucleotides 1510-2565 of FIG. 4 (SEQ ID NO:16) (a gp41 polypeptide). The polynucleotide sequence encoding the Gag-containing and Env-containing polypeptides of the present invention typically have at least about 85%, preferably about 90%, more preferably about 95%, and most preferably about 98% sequence identity to the sequences taught herein.

The polynucleotides of the present invention can be produced by recombinant techniques, synthetic techniques, or combinations thereof.

Also described herein are novel Type C HIV sequences, for example, 8_5_ZA and 12_5/1ZA and synthetic expression cassettes generated from these sequences.

These and other embodiments of the present invention will readily occur to those of ordinary skill in the art in view of the disclosure herein.

BRIEF DESCRIPTION OF THE FIGURES

FIG. 1 (SEQ ID NO:3) shows the nucleotide sequence of a polynucleotide encoding a synthetic Gag polypeptide. The nucleotide sequence shown was obtained by modifying type C strain AF110965 and include further modifications of INS.

FIG. 2 (SEQ ID NO: 4) shows the nucleotide sequence of a polynucleotide encoding a synthetic Gag polypeptide. The nucleotide sequence shown was obtained by modifying type C strain AF110967 and include further modifications of INS.

FIG. 3 (SEQ ID NO:9) shows the nucleotide sequence of a polynucleotide encoding a synthetic Env polypeptide. The nucleotide sequence depicts gp160 (including a signal peptide) and was obtained by modifying type C strain AF110968. The arrows indicate the positions of various regions of the polynucleotide, including the sequence encoding a signal peptide (nucleotides 1-81) (SEQ ID NO:18), a gp120 polypeptide (nucleotides 82-1512) (SEQ ID NO:6), a gp41 polypeptide (nucleotides 1513-2547) (SEQ ID NO:10), a gp140 polypeptide (nucleotides 82-2025) (SEQ ID NO:7) and a gp160 polypeptide (nucleotides 82-2547) (SEQ ID NO:8). The codons encoding the signal peptide are modified (as described herein) from the native HIV-1 signal sequence.

FIG. 4 (SEQ ID NO:15) shows the nucleotide sequence of a polynucleotide encoding a synthetic Env polypeptide. The nucleotide sequence depicts gp160 (including a signal peptide) and was obtained by modifying type C strain AF110975. The arrows indicate the positions of various regions of the polynucleotide, including the sequence encoding a signal peptide (nucleotides 1-72) (SEQ ID NO:19), a gp120 polypeptide (nucleotides 73-1509) (SEQ ID NO:12), a gp41 polypeptide (nucleotides 1510-2565) (SEQ ID NO:16), a gp140 polypeptide (nucleotides 73-2022) (SEQ ID NO:13), and a gp160 polypeptide (nucleotides 73-2565) (SEQ ID NO:14). The codons encoding the signal peptide are modified (as described herein) from the native HIV-1 signal sequence.

FIG. 5 shows the location of some remaining INS in synthetic Gag sequences derived from AF110965. The changes made to these sequences are boxed in the Figures. The top line depicts a codon optimized sequence of Gag polypeptides from the indicated strains (SEQ ID NO:20). The nucleotide(s) appearing below the line in the boxed region(s) depicts changes made to remove further INS and correspond to the sequence depicted in FIG. 1 (SEQ ID NO:3).

FIG. 6 shows the location of some remaining INS in synthetic Gag sequences derived from AF110968. The changes made to these sequences are boxed in the Figures. The top line depicts a codon optimized sequence of Gag polypeptides from the indicated strains (SEQ ID NO:21). The nucleotide(s) appearing below the line in the boxed region(s) depicts changes made to remove further INS and correspond to the sequence depicted in FIG. 2 (SEQ ID NO:4).

FIG. 8 (SEQ ID NO:30) depicts the nucleotide sequence of the construct designated PR975(+). "(+)" indicates that the reverse transcriptase is functional. This construct includes sequence from p2 (nucleotides 16 to 54 of SEQ ID NO:30); p7 (nucleotides 55 to 219 of SEQ ID NO:30); p1/p6 (nucleotides 220-375 of SEQ ID NO:30); prot (nucleotides 376 to 672 of SEQ ID NO:30), reverse transcriptase (nucleotides 673 to 2352 of SEQ ID NO:30); and 6 amino acids of integrase shown in FIG. 7 (nucleotides 2353 to 2370 of SEQ ID NO:30). In addition, the construct contains a multiple cloning site (MCS, nucleotides 2425 to 2463 of SEQ ID NO:30) for insertion of a transgene and a YMDD epitope cassette (nucleotides 2371 to 2424 of SEQ ID NO:30).

FIG. 9 (SEQ ID NO:31) depicts the nucleotide sequence of the construct designated PR975YM. As illustrated in FIG. 7, the RT region includes a mutation in the catalytic center (mut. cat. center). "YM" refers to constructs in which the nucleotides encode the amino acids AP instead of YMDD in this region. Reverse transcriptase is not functional in this construct. This construct includes sequence from the p2 (nucleotides 16 to 54 of SEQ ID NO:31); p7 (nucleotides 55 to 219 of SEQ ID NO:31); p1/p6 (nucleotides 220 to 375 of SEQ ID NO:31); prot (nucleotides 376 to 672 of SEQ ID NO:31); and reverse transcriptase (nucleotides 673 to 2346 of SEQ ID NO:31) shown in FIG. 7, although the reverse transcriptase protein is not functional. In addition, the construct contains a multiple cloning site (MCS, nucleotides 2419 to 2457 of SEQ ID NO:31) for insertion of a transgene and a YMDD epitope cassette (nucleotides 2365 to 2418 of SEQ ID NO:31).

FIG. 10 (SEQ ID NO:32) depicts the nucleotide sequence of the construct designated PR975YMWM. "YM" refers to constructs in which the nucleotides encode the amino acids AP instead of YMDD in this region. "WM" refers to constructs in which the nucleotides encode amino acids PI instead of WMGY in this region. This construct includes sequence from the p2 (nucleotides 16 to 54 of SEQ ID NO:32); p7 (nucleotides 55 to 219 of SEQ ID NO:32); p1/p6 (nucleotides 220 to 375 of SEQ ID NO:32); prot (nucleotides 376 to 672 of SEQ ID NO:32); and reverse transcriptase (nucleotides 673 to 2340 of SEQ ID NO:32) shown in FIG. 7, although the reverse transcriptase protein is not functional. In addition, the construct contains a multiple cloning site (MCS, nucleotides 2413 to 2451 of SEQ ID NO:32) for insertion of a transgene and a YMDD epitope cassette (nucleotides 2359 to 2412 of SEQ ID NO:32).

FIG. 11 (SEQ ID NO:33) depicts the nucleotide sequence of 8_5_ZA. Various regions are shown in Table B.

FIG. 12 (SEQ ID NO:34) depicts the wild type nucleotide sequence of AF110975 Pol from p2gag until p7gag.

FIG. 13 (SEQ ID NO:35) depicts the wild type nucleotide sequence of AF110975 Pol from p1 through the first 6 amino acids of the integrase protein.

FIG. 14 (SEQ ID NO:36) depicts the nucleotide sequence of a cassette encoding Ile178 through Serine 191 of reverse transcriptase.

FIG. 15 (SEQ ID NO:37) shows amino acid sequence which includes an epitope in the region of the catalytic center of the reverse transcriptase protein.

FIG. 16 (SEQ ID NO:45) depicts the nucleotide sequence of 12_5/1ZA

DETAILED DESCRIPTION OF THE INVENTION

Figure 7:
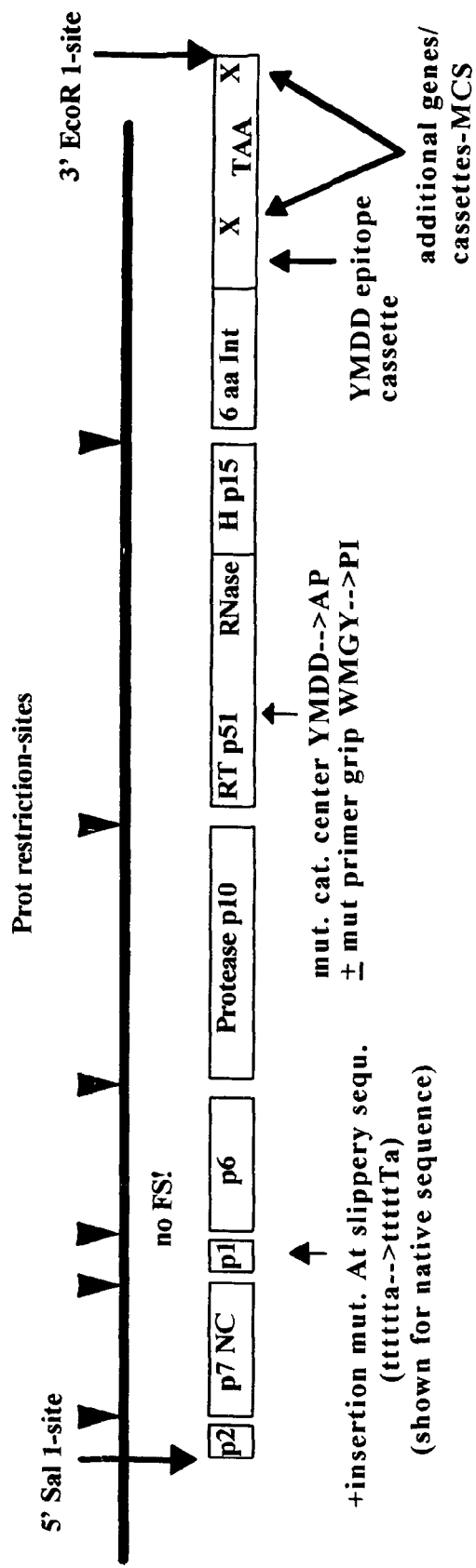
FIG. 7 is a schematic depicting the selected domains in the Pol region of HIV.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology,* 4th ed. (Ausubel et al. eds., 1999, John Wiley & Sons); *Molecular Biology Techniques: An Intensive Laboratory Course*, (Ream et al., eds., 1998, Academic Press); PCR *(Introduction to Biotechniques Series)*, 2nd ed. (Newton & Graham eds., 1997, Springer Verlag).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. DEFINITIONS

In describing the present invention, the following terms will be employed, and are intended to be defined as indicated below.

"Synthetic" sequences, as used herein, refers to Type C HIV polypeptide-encoding polynucleotides whose expression has been optimized as described herein, for example, by codon substitution and inactivation of inhibitory sequences. "Wild-type" or "native" sequences, as used herein, refers to polypeptide encoding sequences that are essentially as they are found in nature, e.g., Pol, Gag and/or Env encoding sequences as found in Type C isolates, e.g., AF110965, AF110967, AF110968, AF110975 or 8_5_ZA. The various regions of the HIV genome are shown in Table A, with numbering relative to 8_5 ZA (SEQ ID NO:33). Thus, the term "Pol" refers to one or more of the following polypeptides: polymerase (p6Pol); protease (prot); reverse transcriptase (p66RT or RT); RNAseH (p15RNAseH); and/or integrase (p31Int or Int).

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, X-ray crystallography, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP.

Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% sequence (including all integer values falling within these described ranges) identity to the synthetic expression cassette sequences disclosed herein (for example, to the claimed sequences or other sequences of the present invention) when the sequences of the present invention are used as the query sequence.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279-287. Examples of suicide genes are thymidine kinase of herpes simplex virus (HSV-tk), cytochrome P450 (Manome et al. (1996) *Gene Therapy* 3:513-520), human deoxycytidine kinase (Manome et al. (1996) *Nature Medicine* 2(5):567-573) and the bacterial enzyme cytosine deaminase (Dong et al. (1996) *Human Gene Therapy* 7:713-720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) *Science* 256:1550-1552, Huber et al. (1994) *Proc. Natl. Acad. Sci. USA* 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (I) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

"Lentiviral vector", and "recombinant lentiviral vector" refer to a nucleic acid construct which carries, and within certain embodiments, is capable of directing the expression of a nucleic acid molecule of interest. The lentiviral vector include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the retrovirus used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof.

"Lentiviral vector particle" as utilized within the present invention refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

"Packaging cell" refers to a cell which contains those elements necessary for production of infectious recombinant retrovirus which are lacking in a recombinant retroviral vector. Typically, such packaging cells contain one or more expression cassettes which are capable of expressing proteins which encode Gag, pol and env proteins.

"Producer cell" or "vector producing cell" refers to a cell which contains all elements necessary for production of recombinant retroviral vector particles.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1. The HIV Genome

The HIV genome and various polypeptide-encoding regions are shown in Table A. The nucleotide positions are given relative to 8_5_ZA (SEQ ID NO:33, FIG. 11). However, it will be readily apparent to one of ordinary skill in the art in view of the teachings of the present disclosure how to determine corresponding regions in other HIV strains or variants (e.g., isolates $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HIV-2_{UC2}$), and simian immunodeficiency virus (SIV). (See, e.g., Virology, 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

TABLE A

Regions of the HIV Genome

| Region | Position in nucleotide sequ. |
| --- | --- |
| 5'LTR | 1-636 |
| U3 | 1-457 |
| R | 458-553 |
| U5 | 554-636 |
| NFkB II | 340-348 |
| NFkB I | 354-362 |
| Sp1 III | 379-388 |
| Sp1 II | 390-398 |

TABLE A-continued

Regions of the HIV Genome

| Region | Position in nucleotide sequ. |
| --- | --- |
| Sp1 I | 400-410 |
| TATA Box | 429-433 |
| TAR | 474-499 |
| Poly A signal | 529-534 |
| PBS | 638-655 |
| p7 binding region, packaging signal | 685-791 |
| Gag: | 792-2285 |
| p17 | 792-1178 |
| p24 | 1179-1871 |
| Cyclophilin A bdg. | 1395-1505 |
| MHR | 1632-1694 |
| p2 | 1872-1907 |
| P7 | 1908-2072 |
| Frameshift slip | 2072-2078 |
| p1 | 2073-2120 |
| p6Gag | 2121-2285 |
| Zn-motif I | 1950-1991 |
| Zn-motif II | 2013-2054 |
| Pol: | 2072-5086 |
| p6Pol | 2072-2245 |
| Prot | 2246-2542 |
| p66RT | 2543-4210 |
| p15RNaseH | 3857-4210 |
| p31Int | 4211-5086 |
| Vif: | 5034-5612 |
| Hydrophilic region | 5292-5315 |
| Vpr: | 5552-5839 |
| Oligomerization | 5552-5677 |
| Amphipathic α-helix | 5597-5653 |
| Tat: | 5823-6038 and 8417-8509 |
| Tat-1 exon | 5823-6038 |
| Tat-2 exon | 8417-8509 |
| N-terminal domain | 5823-5885 |
| Trans-activation domain | 5886-5933 |
| Transduction domain | 5961-5993 |
| Rev: | 5962-6036 and 8416-8663 |
| Rev-1 exon | 5962-6036 |
| Rev-2 exon | 8416-8663 |
| High-affinity bdg. site | 8439-8486 |
| Leu-rich effector domain | 8562-8588 |
| Vpu: | 6060-6326 |
| Transmembrane domain | 6060-6161 |
| Cytoplasmic domain | 6162-6326 |
| Env (gp160): | 6244-8853 |
| Signal peptide | 6244-6324 |
| gp120 | 6325-7794 |
| V1 | 6628-6729 |
| V2 | 6727-6852 |
| V3 | 7150-7254 |
| V4 | 7411-7506 |
| V5 | 7663-7674 |
| C1 | 6325-6627 |
| C2 | 6853-7149 |
| C3 | 7255-7410 |
| C4 | 7507-7662 |
| C5 | 7675-7794 |
| CD4 binding | 7540-7566 |
| gp41 | 7795-8853 |
| Fusion peptide | 7789-7842 |
| Oligomerization domain | 7924-7959 |
| N-terminal heptad repeat | 7921-8028 |
| C-terminal heptad repeat | 8173-8280 |
| Immunodominant region | 8023-8076 |
| Nef: | 8855-9478 |
| Myristoylation | 8858-8875 |
| SH3 binding | 9062-9091 |
| Polypurine tract | 9128-9154 |
| SH3 binding | 9296-9307 |

2.2 Synthetic Expression Cassettes 2.2.1 Modification of HIV-1-Type C Pol-, Prot-, Rt-, Int-, Gag and Env Nucleic Acid Coding Sequences One aspect of the present invention is the generation of HIV-1 type C Gag, Env and Pol coding sequences, and related sequences, having improved expression relative to the corresponding wild-type sequences.

2.2.1.1. Modification of Gag Nucleic Acid Coding Sequences

An exemplary embodiment of the present invention is illustrated herein by modifying the Gag protein wild-type sequences obtained from the AF110965 and AF110967 strains of HIV-1, subtype C. (see, for example, Korber et al. (1998) *Human Retroviruses and Aids*, Los Alamos, N. Mex. Los Alamos National Laboratory; Novitsky et al. (1999) *J. Virol.* 73(5):4427-4432, for molecular cloning of various subtype C clones from Botswana). Gag sequence obtained from other Type C HIV-1 variants may be manipulated in similar fashion following the teachings of the present specification. Such other variants include, but are not limited to, Gag protein encoding sequences obtained from the isolates of HIV-1 Type C, for example as described in Novitsky et al., (1999), supra; Myers et al., infra; Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa. and on the World Wide Web (Internet).

First, the HIV-1 codon usage pattern was modified so that the resulting nucleic acid coding sequence was comparable to codon usage found in highly expressed human genes (Example 1). The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The Gag coding sequences were modified to be comparable to codon usage found in highly expressed human genes.

Second, there are inhibitory (or instability) elements (INS) located within the coding sequences of the Gag coding sequences. The RRE is a secondary RNA structure that interacts with the HIV encoded Rev-protein to overcome the expression down-regulating effects of the INS. To overcome the post-transcriptional activating mechanisms of RRE and Rev, the instability elements can be inactivated by introducing multiple point mutations that do not alter the reading frame of the encoded proteins. Subtype C Gag-encoding sequences having inactivated RRE sites are shown in FIGS. 1 (SEQ ID NO:3), 2 (SEQ ID NO:4), 5 (SEQ ID NO:20) and 6 (SEQ ID NO:26).

Modification of the Gag polypeptide coding sequences results in improved expression relative to the wild-type coding sequences in a number of mammalian cell lines (as well as other types of cell lines, including, but not limited to, insect cells). Further, expression of the sequences results in production of virus-like particles (VLPs) by these cell lines (see below).

2.2.1.2 Modification of Env Nucleic Acid Coding Sequences

Similarly, the present invention also includes modified Env proteins. Wild-type Env sequences are obtained from the AF110968 and AF110975 strains of HIV-1, type C. (see, for example, Novitsky et al. (1999) *J. Virol.* 73(5):4427-4432, for molecular cloning of various subtype C clones from Botswana). Env sequence obtained from other Type C HIV-1 variants may be manipulated in similar fashion following the teachings of the present specification. Such other variants include, but are not limited to, Env protein encoding sequences obtained from the isolates of HIV-1 Type C, described above.

The codon usage pattern for Env was modified as described above for Gag so that the resulting nucleic acid coding sequence was comparable to codon usage found in highly expressed human genes. Experiments can be performed in support of the present invention to show that the synthetic Env sequences were capable of higher level of protein production relative to the native Env sequences.

Modification of the Env polypeptide coding sequences results in improved expression relative to the wild-type coding sequences in a number of mammalian cell lines (as well as other types of cell lines, including, but not limited to, insect cells). Similar Env polypeptide coding sequences can be obtained, optimized and tested for improved expression from a variety of isolates, including those described above for Gag.

2.2.1.3 Modification of Sequences Including Hiv-1 Pol Nucleic Acid Coding Sequences The present invention also includes expression cassettes which include synthetic Pol sequences. As noted above, "Pol" includes, but is not limited to, the protein-encoding regions shown in FIG. 7, for example polymerase, protease, reverse transcriptase and/or integrase-containing sequences. The regions shown in FIG. 7 are described, for example, in Wan et et al (1996) *Biochem. J.* 316:569-573; Kohl et al. (1988) *PNAS USA* 85:4686-4690; Krausslich et al. (1988) *J. Virol.* 62:4393-4397; Coffin, "Retroviridae and their Replication" in Virology, pp 1437-1500 (Raven, New York, 1990); Patel et. al. (1995) *Biochemistry* 34:5351-5363. Thus, the synthetic expression cassettes exemplified herein include one or more of these regions and one or more changes to the resulting amino acid sequences.

Wild type Pol sequences were obtained from the AF110975 strains of HIV-1, type C. (see, for example, Novitsky et al. (1999) *J. Virol.* 73(5):4427-4432, for molecular cloning of various subtype C clones from Botswana). SEQ ID NO:34 shows the wild type sequence from the p2 through p7 region of Pol (see, FIG. 7 and Table A). SEQ ID NO:35 shows the wild type sequence from p1 through the first 6 amino acids of integrase (see, FIG. 7 and Table A). Sequence obtained from other Type C HIV-1 variants may be manipulated in similar fashion following the teachings of the present specification. Such other variants include, but are not limited to, Pol protein encoding sequences obtained from the isolates of HIV-1 Type C described herein.

The codon usage pattern for Pol was modified as described above for Gag and Env so that the resulting nucleic acid coding sequence was comparable to codon usage found in highly expressed human genes.

Table B shows the nucleotide positions of various regions found in the Pol constructs exemplified herein (SEQ ID NOs: 30-32).

TABLE B

| | Position in nucleotide sequence in construct | | |
|---|---|---|---|
| Region | PR975(+) Seq Id No: 30 | PR975YM Seq Id No: 31 | PR975(+)YMWM Seq Id No: 32 |
| Sal 1 restriction site | 1-6 | 1-6 | 1-6 |
| Kozak start codon | 7-16 | 7-16 | 7-16 |
| p2 | 16-54 | 16-54 | 16-54 |
| P7 | 55-219 | 55-219 | 55-219 |
| p1/p6 pol | 220-375 | 220-375 | 220-375 |
| Insertion mutation for in frame | 225 | 225 | 225 |
| p10Protease | 376-672 | 376-672 | 376-672 |
| p66RT | 673-2352 | 673-2346 | 673-2340 |
| p51RT | 673-1992 | 673-1986 | 673-1980 |
| p15RNaseH | 1993-2352 | 1993-2346 | 1993-2340 |

TABLE B-continued

| | Position in nucleotide sequence in construct | | |
|---|---|---|---|
| Region | PR975(+) Seq Id No: 30 | PR975YM Seq Id No: 31 | PR975(+)YMWM Seq Id No: 32 |
| catalytic center region (YMDD) | 1219-1230 | 1219-1224 | 1219-1224 |
| primer grip region (WMGy) | 1357-1368 | 1351-1362 | 1351-1356 |
| 6aa Integrase | 2353-2370 | 2347-2364 | 2341-2358 |
| YMDD epitope cassette (incl. 5' + 3' Gly) | 2371-2424 | 2365-2418 | 2359-2412 |
| MCS (multiple cloning site) | 2425-2463 | 2419-2457 | 2413-2451 |
| EcoR 1 restriction site | 2464-2469 | 2458-2463 | 2452-2457 |

As shown in Table B, exemplary constructs were modified in various ways. For example, the expression constructs exemplified herein include sequence that encodes the first 6 amino acids of the integrase polypeptide. This 6 amino acid region is believed to provide a cleavage recognition site recognized by HIV protease (see, e.g., McCornack et al. (1997) *FEBS Letts* 414:84-88). As noted above, certain constructs exemplified herein include a multiple cloning site (MCS) for insertion of one or more transgenes, typically at the 3' end of the construct. In addition, a cassette encoding a catalytic center epitope derived from the catalytic center in RT is typically included 3' of the sequence encoding 6 amino acids of integrase. This cassette (SEQ ID NO:36) encodes Ile178 through Serine 191 of RT (amino acids 3 through 16 of SEQ ID NO:37) and was added to keep this well conserved region as a possible CTL epitope. Further, the constructs contain an insertion mutations (position 225 of SEQ ID NOs:30 to 32) to preserve the reading frame. (see, e.g., Park et al. (1991) *J. Virol.* 65:5111).

In certain embodiments, the catalytic center and/or primer grip region of RT are modified. The catalytic center and primer grip regions of RT are described, for example, in Patel et al. (1995) *Biochem.* 34:5351 and Palaniappan et al. (1997) *J. Biol. Chem.* 272(17):11157. For example, in the construct designated PR975YM (SEQ ID NO:31), wild type sequence encoding the amino acids YMDD at positions 183-185 of p66 RT, numbered relative to AF110975, are replaced with sequence encoding the amino acids "AP". In the construct designated PR975YMWM (SEQ ID NO:32), the same mutation in YMDD is made and, in addition, the primer grip region (amino acids WMGY, residues 229-232 of p66RT, numbered relative to AF110975) are replaced with sequence encoding the amino acids "PI."

For the Pol sequence, the changes in codon usage are typically restricted to the regions up to the −1 frameshift and starting again at the end of the Gag reading frame; however, regions within the frameshift translation region can be modified as well. Finally, inhibitory (or instability) elements (INS) located within the coding sequences of the protease polypeptide coding sequence can be altered as well.

Experiments can be performed in support of the present invention to show that the synthetic Pol sequences were capable of higher level of protein production relative to the native Pol sequences. Modification of the Pol polypeptide coding sequences results in improved expression relative to the wild-type coding sequences in a number of mammalian cell lines (as well as other types of cell lines, including, but not limited to, insect cells). Similar Pol polypeptide coding sequences can be obtained, optimized and tested for improved expression from a variety of isolates, including those described above for Gag.

2.2.1.4 Modification of Sequences from 8__5_ZA

The present invention also includes expression cassettes which include synthetic HIV Type C sequences derived from 8_5_ZA (SEQ ID NO:33). Wild-type sequences for various polypeptide-encoding regions are obtained from #8_5_ZA (SEQ ID NO:33) and manipulated in similar fashion following the teachings of the present specification. The codon usage pattern for 8_5_ZA is modified as described above for Gag, Env and Pol so that the resulting nucleic acid coding sequence is comparable to codon usage found in highly expressed human genes. Experiments can be performed in support of the present invention to show that the synthetic 8_5_ZA sequences were capable of higher level of protein production relative to the native 8_5_ZA sequences.

Modification of the 8_5 ZA polypeptide coding sequences results in improved expression relative to the wild-type coding sequences in a number of mammalian cell lines (as well as other types of cell lines, including, but not limited to, insect cells).

2.2.1.5 Further Modification of Sequences Including HIV-1 Nucleic Acid Coding Sequences The Type C HIV polypeptide-encoding expression cassettes described herein may also contain one or more further sequences encoding, for example, one or more transgenes. Further sequences (e.g., transgenes) useful in the practice of the present invention include, but are not limited to, further sequences are those encoding further viral epitopes/antigens {including but not limited to, HCV antigens (e.g., E1, E2; Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference), HIV antigens (e.g., derived from tat, rev, nef and/or env); and sequences encoding tumor antigens/epitopes. Further sequences may also be derived from non-viral sources, for instance, sequences encoding cytokines such interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-11), interleukin-11 (IL-11), MIP-11, tumor necrosis factor (TNF), leukemia inhibitory factor (LIF), c-kit ligand, thrombopoietin (TPO) and flt3 ligand, commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additional sequences are described below, for example in Section 2.3. Also, variations on the orientation of the Gag and other coding sequences, relative to each other, are described below.

Gag, Env, and Pol polypeptide coding sequences can be obtained from other Type C HIV isolates, see, e.g., Myers et al. Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory. Synthetic expression cassettes can be generated using such coding sequences as starting material by following the teachings of the present specification (e.g., see Example 1).

Further, the synthetic expression cassettes of the present invention include related Pol, Gag and/or containing polypeptide sequences having greater than 85%, preferably greater than 90%, more preferably greater than 95%, and most preferably greater than 98% sequence identity to the synthetic expression cassette sequences disclosed herein (for example, (SEQ ID NOs:30-32; SEQ ID NOs: 3, 4, 20, and 21 and SEQ ID NOs:5-17). Various coding regions are indicated in FIGS. 3 and 4, for example in FIG. 3 (AF110968), nucleotides 1-81 (SEQ ID NO:18) encode a signal peptide, nucleotides 82-1512 (SEQ ID NO:6) encode a gp120 polypeptide, nucleotides 1513 to 2547 (SEQ ID NO:10) encode a gp41 polypeptide, nucleotides 82-2025 (SEQ ID NO:7) encode a gp140 polypeptide and nucleotides 82-2547 (SEQ ID NO:8) encode a gp160 polypeptide.

2.2.3 Expression of Synthetic Sequences Encoding HIV-1 Pol, Gag or Env and Related Polypeptides Synthetic Pol-, Gag- and/or Env-encoding sequences (expression cassettes) of the present invention can be cloned into a number of different expression vectors to evaluate levels of expression and, in the case of Gag, production of VLPs. The synthetic DNA fragments for Pol, Env and Gag can be cloned into eucaryotic expression vectors, including, a transient expression vector, CMV-promoter-based mammalian vectors, and a shuttle vector for use in baculovirus expression systems. Corresponding wild-type sequences can also be cloned into the same vectors.

These vectors can then be transfected into a several different cell types, including a variety of mammalian cell lines (293, RD, COS-7, and CHO, cell lines available, for example, from the A.T.C.C.). The cell lines are then cultured under appropriate conditions and the levels of p24 (Gag) or, gp160 or gp120 (Env) expression in supernatants can be evaluated (Example 2). Env polypeptides include, but are not limited to, for example, native gp160, oligomeric gp140, monomeric gp120 as well as modified sequences of these polypeptides. The results of these assays demonstrate that expression of synthetic Pol, Env, Gag encoding sequences are significantly higher than corresponding wild-type sequences.

Further, Western Blot analysis can be used to show that cells containing the synthetic Pol, Gag or Env expression cassette produce the expected protein at higher per-cell concentrations than cells containing the native expression cassette. The Pol, Gag and Env proteins can be seen in both cell lysates and supernatants. The levels of production are significantly higher in cell supernatants for cells transfected with the synthetic expression cassettes of the present invention.

Fractionation of the supernatants from mammalian cells transfected with the synthetic Pol, Gag or Env expression cassette can be used to show that the cassettes provide superior production of both Gag and Env proteins and, in the case of Gag, VLPs, relative to the wild-type sequences.

Efficient expression of these Pol, Gag- and/or Env-containing polypeptides in mammalian cell lines provides the following benefits: the polypeptides are free of baculovirus contaminants; production by established methods approved by the FDA; increased purity; greater yields (relative to native coding sequences); and a novel method of producing the Pol, Gag- and/or Env-containing polypeptides in CHO cells which is not feasible in the absence of the increased expression obtained using the constructs of the present invention. Exemplary Mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, and CEMX174, such cell lines are available, for example, from the A.T.C.C.).

A synthetic Gag expression cassette of the present invention will also exhibit high levels of expression and VLP production when transfected into insect cells. Synthetic Env expression cassettes also demonstrate high levels of expression in insect cells. Further, in addition to a higher total protein yield, the final product from the synthetic polypeptides consistently contains lower amounts of contaminating baculovirus proteins than the final product from the native Pol, Gag or Env.

Further, synthetic Pol, Gag and Env expression cassettes of the present invention can also be introduced into yeast vectors which, in turn, can be transformed into and efficiently expressed by yeast cells (*Saccharomyces cerevisea*; using vectors as described in Rosenberg, S, and Tekamp-Olson, P., U.S. Pat. No. RE35,749, issued, Mar. 17, 1998, herein incorporated by reference).

In addition to the mammalian and insect vectors, the synthetic expression cassettes of the present invention can be incorporated into a variety of expression vectors using selected expression control elements. Appropriate vectors and control elements for any given cell type can be selected by one having ordinary skill in the art in view of the teachings of the present specification and information known in the art about expression vectors.

For example, a synthetic Pol, Gag or Env expression cassette can be inserted into a vector which includes control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-Ltr, the mouse mammary tumor virus LTR promoter (MMLV-ltr), the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res.* (1991) 19:3979-3986), Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence (Chapman et al., *Nuc. Acids Res.* (1991) 19:3979-3986).

The desired synthetic Pol, Gag or Env polypeptide encoding sequences can be cloned into any number of commercially available vectors to generate expression of the polypeptide in an appropriate host system. These systems include, but are not limited to, the following: baculovirus expression {Reilly, P. R., et al., *BACULOVIRUS EXPRESSION VECTORS: A LABORATORY MANUAL* (1992); Beames, et al., *Biotechniques* 11:378 (1991); Pharmingen; Clontech, Palo Alto, Calif.)}, vaccinia expression {Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., CURRENT PROTOCOLS IN MOLECULAR BIOLOGY, John Wiley and Sons, Inc., Media Pa.; Clontech}, expression in yeast {Rosenberg, S, and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., *Antonie Van Leeuwenhoek,* 62(1-2):79-93 (1992); Romanos, M. A., et al., *Yeast* 8(6):423-488 (1992); Goeddel, D. V., *Methods in Enzymology* 185 (1990); Guthrie, C., and G. R. Fink, *Methods in Enzymology* 194 (1991)1, expression in mammalian cells {Clontech; Gibco-BRL, Ground Island, N.Y.; e.g., Chinese hamster ovary (CHO) cell lines (Haynes, J., et al., *Nuc. Acid. Res.* 11:687-706 (1983); 1983, Lau, Y. F., et al., *Mol. Cell. Biol.* 4:1469-1475 (1984); Kaufman, R. J., "Selection and coamplification of heterologous genes in mammalian cells," in *Methods in Enzymology,* vol. 185, pp 537-566. Academic Press, Inc., San Diego Calif. (1991)1, and expression in plant cells {plant cloning vectors, Clontech Laboratories, Inc., Palo Alto, Calif., and Pharmacia LKB Biotechnology, Inc., Pistcataway, N J; Hood, E., et al., *J. Bacteriol.* 168:1291-1301 (1986); Nagel, R., et al., *FEMS Microbiol. Lett.* 67:325 (1990); An, et al., "Binary Vectors", and others in *Plant Molecular Biology Manual A*3:1-19 (1988); Miki, B. L. A., et al., pp. 249-265, and others in *Plant DNA Infectious Agents* (Hohn, T., et al., eds.) Springer-Verlag, Wien, Austria, (1987); *Plant Molecular Biology: Essential Techniques,* P. G. Jones and J. M. Sutton, New York, J. Wiley, 1997; Miglani, Gurbachan *Dictionary of Plant Genetics and Molecular Biology,* New York, Food Products Press, 1998; Henry, R. J., *Practical Applications of Plant Molecular Biology,* New York, Chapman & Hall, 1997}.

Also included in the invention is an expression vector, containing coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., *Mamm. Genome* 7(8):563-574, 1996; Kozak, M., *Biochimie* 76(9): 815-821, 1994; Kozak, M., *J Cell Biol* 108(2):229-241, 1989; Kozak, M., and Shatkin, A. J., *Methods Enzymol* 60:360-375, 1979).

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic Pol, Gag- and/or Env-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, Gag or Env antigens.

Advantages of expressing the Pol, Gag- and/or Env-containing proteins of the present invention using mammalian cells include, but are not limited to, the following: well-established protocols for scale-up production; the ability to produce VLPs; cell lines are suitable to meet good manufacturing process (GMP) standards; culture conditions for mammalian cells are known in the art.

Various forms of the different embodiments of the invention, described herein, may be combined.

2.3 Production of Virus-Like Particles and Use of the Constructs of the Present Invention to Create Packaging Cell Lines.

The group-specific antigens (Gag) of human immunodeficiency virus type-1 (HIV-1) self-assemble into noninfectious virus-like particles (VLP) that are released from various eucaryotic cells by budding (reviewed by Freed, E. O., *Virology* 251:1-15, 1998). The synthetic expression cassettes of the present invention provide efficient means for the production of HIV-Gag virus-like particles (VLPs) using a variety of different cell types, including, but not limited to, mammalian cells.

Viral particles can be used as a matrix for the proper presentation of an antigen entrapped or associated therewith to the immune system of the host.

2.3.1 VLP Production Using the Synthetic Expression Cassettes of The Present Invention Experiments can be performed in support of the present invention to demonstrate that the synthetic expression cassettes of the present invention provide superior production of both Gag proteins and VLPs, relative to native Gag coding sequences. Further, electron microscopic evaluation of VLP production can show that free and budding immature virus particles of the expected size are produced by cells containing the synthetic expression cassettes.

Using the synthetic expression cassettes of the present invention, rather than native Gag coding sequences, for the production of virus-like particles provide several advantages. First, VLPs can be produced in enhanced quantity making isolation and purification of the VLPs easier. Second, VLPs can be produced in a variety of cell types using the synthetic expression cassettes, in particular, mammalian cell lines can be used for VLP production, for example, CHO cells. Production using CHO cells provides (i) VLP formation; (ii) correct myristylation and budding; (iii) absence of non-mammalian cell contaminants (e.g., insect viruses and/or cells); and (iv) ease of purification. The synthetic expression cassettes of the present invention are also useful for enhanced expression in cell-types other than mammalian cell lines. For example, infection of insect cells with baculovirus vectors encoding the synthetic expression cassettes results in higher levels of total Gag protein yield and higher levels of VLP production (relative to wild-type coding sequences). Further, the final product from insect cells infected with the baculovirus-Gag synthetic expression cassettes consistently contains lower amounts of contaminating insect proteins than the final product when wild-type coding sequences are used.

VLPs can spontaneously form when the particle-forming polypeptide of interest is recombinantly expressed in an appropriate host cell. Thus, the VLPs produced using the synthetic expression cassettes of the present invention are conveniently prepared using recombinant techniques. As discussed below, the Gag polypeptide encoding synthetic expression cassettes of the present invention can include other polypeptide coding sequences of interest (for example, HIV protease, HIV polymerase, HCV core; Env; synthetic Env; see, Example 1). Expression of such synthetic expression cassettes yields VLPs comprising the Gag polypeptide, as well as, the polypeptide of interest.

Once coding sequences for the desired particle-forming polypeptides have been isolated or synthesized, they can be cloned into any suitable vector or replicon for expression.

Numerous cloning vectors are known to those of skill in the art, and the selection of an appropriate cloning vector is a matter of choice. See, generally, Sambrook et al, supra. The vector is then used to transform an appropriate host cell. Suitable recombinant expression systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

For example, a number of mammalian cell lines are known in the art and include immortalized cell lines available from the American Type Culture Collection (A.T.C.C.), such as, but not limited to, Chinese hamster ovary (CHO) cells, HeLa cells, baby hamster kidney (BHK) cells, monkey kidney cells (COS), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. See, e.g., Summers and Smith, *Texas Agricultural Experiment Station Bulletin No.* 1555 (1987).

Viral vectors can be used for the production of particles in eucaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, *J. Mol. Biol.* (1986) 189:113-130). The method provides for high level, transient, cytoplasmic production of large quantities of RNA and its translation product(s).

Depending on the expression system and host selected, the VLPS are produced by growing host cells transformed by an expression vector under conditions whereby the particle-forming polypeptide is expressed and VLPs can be formed. The selection of the appropriate growth conditions is within the skill of the art. If the VLPs are formed intracellularly, the cells are then disrupted, using chemical, physical or mechanical means, which lyse the cells yet keep the VLPs substantially intact. Such methods are known to those of skill in the art and are described in, e.g., *Protein Purification Applications: A Practical Approach*, (E. L. V. Harris and S. Angal, Eds., 1990).

The particles are then isolated (or substantially purified) using methods that preserve the integrity thereof, such as, by gradient centrifugation, e.g., cesium chloride (CsCl) sucrose gradients, pelleting and the like (see, e.g., Kirnbauer et al. *J. Virol.* (1993) 67:6929-6936), as well as standard purification techniques including, e.g., ion exchange and gel filtration chromatography.

VLPs produced by cells containing the synthetic expression cassettes of the present invention can be used to elicit an immune response when administered to a subject. One advantage of the present invention is that VLPs can be produced by mammalian cells carrying the synthetic expression cassettes at levels previously not possible. As discussed above, the VLPs can comprise a variety of antigens in addition to the Gag polypeptide (e.g., Gag-protease, Gag-polymerase, Env, synthetic Env, etc.). Purified VLPs, produced using the synthetic expression cassettes of the present invention, can be administered to a vertebrate subject, usually in the form of vaccine compositions. Combination vaccines may also be used, where such vaccines contain, for example, an adjuvant subunit protein (e.g., Env). Administration can take place using the VLPs formulated alone or formulated with other antigens; Further, the VLPs can be administered prior to, concurrent with, or subsequent to, delivery of the synthetic expression cassettes for DNA immunization (see below) and/or delivery of other vaccines. Also, the site of VLP administration may be the same or different as other vaccine compositions that are being administered. Gene delivery can be accomplished by a number of methods including, but are not limited to, immunization with DNA, alphavirus vectors, pox virus vectors, and vaccinia virus vectors.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 1000 µg, more preferably about 1 µg to about 300 µg, of VLP/antigen.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli*.

Adjuvants may also be used to enhance the effectiveness of the compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) oligonucleotides or polymeric molecules encoding immunostimulatory CpG mofits (Davis, H. L., et al., *J. Immunology* 160:870-876, 1998; Sato, Y. et al., *Science* 273:352-354, 1996) or complexes of antigens/oligonucleotides {Polymeric molecules include double and single stranded RNA and DNA, and backbone modifications thereof, for example, methylphosphonate linkages; or (7) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and W092/19265); and (8) other substances that act as immunostimulating agents to enhance the effectiveness of the composition. Further, such polymeric molecules include alternative polymer backbone structures such as, but not limited to, polyvinyl backbones (Pitha, *Biochem Biophys Acta*, 204:39, 1970a; Pitha, *Biopolymers*, δ: 965, 1970b), and morpholino backbones (Summerton, J., et al., U.S. Pat. No. 5,142,047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).}; and (7) other substances that act as immunostimulating agents to enhance the effectiveness of the VLP immune-stimulating (or vaccine) composition. Alum, CpG oligonucleotides, and MF59 are preferred.

Muramyl peptides include, but are not limited to, N-acetylmuramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner.

If prevention of disease is desired, the antigen carrying VLPs are generally administered prior to primary infection with the pathogen of interest. If treatment is desired, e.g., the reduction of symptoms or recurrences, the VLP compositions are generally administered subsequent to primary infection.

2.3.2 Using the Synthetic Expression Cassettes of the Present Invention to Create Packaging Cell Lines A number of viral based systems have been developed for use as gene transfer vectors for mammalian host cells. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo. A number of retroviral systems have been described, including, for example, the following: (U.S. Pat. No. 5,219,740; Miller et al. (1989) *BioTechniques* 7:980; Miller, A. D. (1990) *Human Gene Therapy* 1:5; Scarpa et al. (1991) *Virology* 180:849; Burns et al. (1993) *Proc. Natl. Acad. Sci. USA* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. No. 5,219,740; U.S. Pat. No. 4,405,712; U.S. Pat. No. 4,861,719; U.S. Pat. No. 4,980,289 and U.S. Pat. No. 4,777,127; in U.S. Ser. No. 07/800,921; and in Vile (1993) *Cancer Res* 53:3860-3864; Vile (1993) *Cancer Res* 53:962-967; Ram (1993) *Cancer Res* 53:83-88; Takamiya (1992) *Neurosci Res* 33:493-503; Baba (1993) *J Neurosurg* 79:729-735; Mann (1983) *Cell* 33:153; Cane (1984) *Proc Natl Acad Sci USA* 81; 6349; and Miller (1990) *Human Gene Therapy* 1.

In other embodiments, gene transfer vectors can be constructed to encode a cytokine or other immunomodulatory molecule. For example, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879,227, respectively. In particular aspects of the invention, retroviral vectors expressing cytokine or immunomodulatory genes can be produced as described herein (for example, employing the packaging cell lines of the present invention) and in International Application No. PCT US 94/02951, entitled "Compositions and Methods for Cancer Immunotherapy."

Examples of suitable immunomodulatory molecules for use herein include the following: IL-1 and IL-2 (Karupiah et al. (1990) *J. Immunology* 144:290-298, Weber et al. (1987) *J. Exp. Med.* 166:1716-1733, Gansbacher et al. (1990) *J. Exp. Med.* 172:1217-1224, and U.S. Pat. No. 4,738,927); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (*Cytokine Bulletin*, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-

394, Twu et al. (1989) *Proc. Natl. Acad. Sci. USA* 86:2046-2050, and Faktor et al. (1990) *Oncogene* 5:867-872); beta-interferon (Seif et al. (1991) *J. Virol.* 65:664-671); gamma-interferons (Radford et al. (1991) *The American Society of Hepatology* 20082015, Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188).

Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids containing cytokine genes or immunomodulatory genes (International Publication Nos. WO 94/02951 and WO 96/21015, both of which are incorporated by reference in their entirety) can be digested with appropriate restriction enzymes, and DNA fragments containing the particular gene of interest can be inserted into a gene transfer vector using standard molecular biology techniques. (See, e.g., Sambrook et al., supra., or Ausbel et al. (eds) *Current Protocols in Molecular Biology*, Greene Publishing and Wiley-Interscience).

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlich (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The synthetic expression cassettes of the present invention can be employed in the construction of packaging cell lines for use with retroviral vectors.

One type of retrovirus, the murine leukemia virus, or "MLV", has been widely utilized for gene therapy applications (see generally Maim et al. (*Cell* 33:153, 1993), Cane and Mulligan (*Proc, Nat'l. Acad. Sci. USA* 81:6349, 1984), and Miller et al., *Human Gene 2Ierapy* 1:5-14, 1990.

Lentiviral vectors typically, comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). Within certain embodiments, the nuclear transport element is not RRE. Within one embodiment the packaging signal is an extended packaging signal. Within other embodiments the promoter is a tissue specific promoter, or, alternatively, a promoter such as CMV. Within other embodiments, the lentiviral vector further comprises an internal ribosome entry site.

A wide variety of lentiviruses may be utilized within the context of the present invention, including for example, lentiviruses selected from the group consisting of HIV, HIV-1, HIV-2, FIV and SIV.

In one embodiment of the present invention synthetic Gag-polymerase expression cassettes are provided comprising a promoter and a sequence encoding synthetic Gag-polymerase and at least one of vpr, vpu, nef or vif, wherein the promoter is operably linked to Gag-polymerase and vpr, vpu, nef or vif.

Within yet another aspect of the invention, host cells (e.g., packaging cell lines) are provided which contain any of the expression cassettes described herein. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Packaging cell lines may further comprise a promoter and a sequence encoding tat, rev, or an envelope, wherein the promoter is operably linked to the sequence encoding tat, rev, Env or modified Env proteins. The packaging cell line may further comprise a sequence encoding any one or more of nef, vif, vpu or vpr.

In one embodiment, the expression cassette (carrying, for example, the synthetic Gag-polymerase) is stably integrated.

The packaging cell line, upon introduction of a lentiviral vector, typically produces particles. The promoter regulating expression of the synthetic expression cassette may be inducible. Typically, the packaging cell line, upon introduction of a lentiviral vector, produces particles that are essentially free of replication competent virus.

Packaging cell lines are provided comprising an expression cassette which directs the expression of a synthetic Gag-polymerase gene or comprising an expression cassette which directs the expression of a synthetic Env genes described herein. (See, also, Andre, S., et al., *Journal of Virology* 72(2): 1497-1503, 1998; Haas, J., et al., *Current Biology* 6(3):315-324, 1996) for a description of other modified Env sequences). A lentiviral vector is introduced into the packaging cell line to produce a vector producing cell line.

As noted above, lentiviral vectors can be designed to carry or express a selected gene(s) or sequences of interest. Lentiviral vectors may be readily constructed from a wide variety of lentiviruses (see RNA Tumor Viruses, Second Edition, Cold Spring Harbor Laboratory, 1985). Representative examples of lentiviruses included HIV, HIV-1, HIV-2, FIV and SIV. Such lentiviruses may either be obtained from patient isolates, or, more preferably, from depositories or collections such as the American Type Culture Collection, or isolated from known sources using available techniques.

Portions of the lentiviral gene delivery vectors (or vehicles) may be derived from different viruses. For example, in a given recombinant lentiviral vector, LTRs may be derived from an HIV, a packaging signal from SIV, and an origin of second strand synthesis from HrV-2. Lentiviral vector constructs may comprise a 5' lentiviral LTR, a tRNA binding site, a packaging signal, one or more heterologous sequences, an origin of second strand DNA synthesis and a 3' LTR, wherein said lentiviral vector contains a nuclear transport element that is not RRE.

Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5'LTR. Similarly, the origin of second strand DNA synthesis is, as its name implies, important for the second strand DNA synthesis of a retrovirus. This region, which is also referred to as the poly-purine tract, is located just upstream of the 3'LTR.

In addition to a 5' and 3' LTR, tRNA binding site, and origin of second strand DNA synthesis, recombinant retroviral vector constructs may also comprise a packaging signal, as well as one or more genes or coding sequences of interest. In addition, the lentiviral vectors have a nuclear transport element which, in preferred embodiments is not RRE. Representative examples of suitable nuclear transport elements include the element in Rous sarcoma virus (Ogert, et al., *J. ViroL* 70, 3834-3843, 1996), the element in Rous sarcoma virus (Liu & Mertz, *Genes & Dev.*, 9, 1766-1789, 1995) and the element in the genome of simian retrovirus type I (Zolotukhin, et al., *J. Virol.* 68, 7944-7952, 1994). Other potential elements include the elements in the histone gene (Kedes, *Annu. Rev. Biochem.* 48, 837-870, 1970), the α-interferon gene (Nagata et al., *Nature* 287, 401-408, 1980), the β-adrenergic receptor gene (Koilka, et al., *Nature* 329, 75-79, 1987), and the c-Jun gene (Hattorie, et al., *Proc. Natl. Acad. Sci. USA* 85, 9148-9152, 1988).

Recombinant lentiviral vector constructs typically lack both Gag-polymerase and Env coding sequences. Recombinant lentiviral vector typically contain less than 20, preferably 15, more preferably 10, and most preferably 8 consecutive nucleotides found in Gag-polymerase and Env genes. One advantage of the present invention is that the synthetic Gag-polymerase expression cassettes, which can be used to construct packaging cell lines for the recombinant retroviral vector constructs, have little homology to wild-type Gag-polymerase sequences and thus considerably reduce or eliminate the possibility of homologous recombination between the synthetic and wild-type sequences.

Lentiviral vectors may also include tissue-specific promoters to drive expression of one or more genes or sequences of interest.

Lentiviral vector constructs may be generated such that more than one gene of interest is expressed. This may be accomplished through the use of di- or oligo-cistronic cassettes (e.g., where the coding regions are separated by 80 nucleotides or less, see generally Levin et al., *Gene* 108:167-174, 1991), or through the use of Internal Ribosome Entry Sites ("IRES").

Packaging cell lines suitable for use with the above described recombinant retroviral vector constructs may be readily prepared given the disclosure provided herein.

Briefly, the parent cell line from which the packaging cell line is derived can be selected from a variety of mammalian cell lines, including for example, 293, RD, COS-7, CHO, BHK, VERO HT1080, and myeloma cells.

After selection of a suitable host cell for the generation of a packaging cell line, one or more expression cassettes are introduced into the cell line in order to complement or supply in trans components of the vector which have been deleted.

Representative examples of suitable expression cassettes have been described herein and include synthetic Env, synthetic Gag, synthetic Gag-protease, and synthetic Gag-polymerase expression cassettes, which comprise a promoter and a sequence encoding, e.g., Gag-polymerase and at least one of vpr, vpu, nef or vif, wherein the promoter is operably linked to Gag-polymerase and vpr, vpu, nef or vif. As described above, the native and/or modified Env coding sequences may also be utilized in these expression cassettes.

Utilizing the above-described expression cassettes, a wide variety of packaging cell lines can be generated. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Within other aspects, packaging cell lines are provided comprising a promoter and a sequence encoding tat, rev, Env, or other HIV antigens or epitopes derived therefrom, wherein the promoter is operably linked to the sequence encoding tat, rev, Env, or the HIV antigen or epitope. Within further embodiments, the packaging cell line may comprise a sequence encoding any one or more of nef, vif, vpu or vpr. For example, the packaging cell line may contain only nef, vif, vpu, or vpr alone, nef and vif, nef and vpu, nef and vpr, vif and vpu, vif and vpr, vpu and vpr, nef vif and vpu, nef vif and vpr, nef vpu and vpr, vvir vpu and vpr, or, all four of nef vif vpu and vpr.

In one embodiment, the expression cassette is stably integrated. Within another embodiment, the packaging cell line, upon introduction of a lentiviral vector, produces particles. Within further embodiments the promoter is inducible. Within certain preferred embodiments of the invention, the packaging cell line, upon introduction of a lentiviral vector, produces particles that are free of replication competent virus.

The synthetic cassettes containing optimized coding sequences are transfected into a selected cell line. Transfected cells are selected that (i) carry, typically, integrated, stable copies of the Gag, Pol, and Env coding sequences, and (ii) are expressing acceptable levels of these polypeptides (expression can be evaluated by methods known in the prior art, e.g., see Examples 1-4). The ability of the cell line to produce VLPs may also be verified.

A sequence of interest is constructed into a suitable viral vector as discussed above. This defective virus is then transfected into the packaging cell line. The packaging cell line provides the viral functions necessary for producing virus-like particles into which the defective viral genome, containing the sequence of interest, are packaged. These VLPs are then isolated and can be used, for example, in gene delivery or gene therapy.

Further, such packaging cell lines can also be used to produce VLPs alone, which can, for example, be used as adjuvants for administration with other antigens or in vaccine compositions. Also, co-expression of a selected sequence of interest encoding a polypeptide (for example, an antigen) in the packaging cell line can also result in the entrapment and/or association of the selected polypeptide in/with the VLPs.

Various forms of the different embodiments of the present invention (e.g., constructs) may be combined.

2.4 DNA Immunization and Gene Delivery

A variety of HIV polypeptide antigens, particularly Type C HIV antigens, can be used in the practice of the present invention. HIV antigens can be included in DNA immunization constructs containing, for example, a synthetic Gag expression cassette fused in-frame to a coding sequence for the polypeptide antigen, where expression of the construct results in VLPs presenting the antigen of interest.

HIV antigens of particular interest to be used in the practice of the present invention include tat, rev, nef, vif, vpu, vpr, and other HIV antigens or epitopes derived therefrom. For example, the packaging cell line may contain only nef, and HIV-1 (also known as HTLV-III, LAV, ARV, etc.), including, but not limited to, antigens such as gp120, gp41, gp160 (both native and modified); Gag; and pol from a variety of isolates including, but not limited to, $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HW-2_{UC2}$). See, e.g., Myers, et al., Los Alamos Database, Los Alamos National Laboratory, Los Alamos, N. Mex.; Myers, et al., *Human Retroviruses and Aids,* 1990, Los Alamos, N. Mex. Los Alamos National Laboratory.

To evaluate efficacy, DNA immunization using synthetic expression cassettes of the present invention can be performed, for instance as described in Example 4. Mice are immunized with both the Gag (and/or Env) synthetic expression cassette and the Gag (and/or Env) wild type expression cassette. Mouse immunizations with plasmid-DNAs will show that the synthetic expression cassettes provide a clear improvement of immunogenicity relative to the native expression cassettes. Also, the second boost immunization will induce a secondary immune response, for example, after approximately two weeks. Further, the results of CTL assays will show increased potency of synthetic Gag (and/or Env) expression cassettes for induction of cytotoxic T-lymphocyte (CTL) responses by DNA immunization.

It is readily apparent that the subject invention can be used to mount an immune response to a wide variety of antigens and hence to treat or prevent a HIV infection, particularly Type C HIV infection.

2.4.1 Delivery of the Synthetic Expression Cassettes of the Present Invention

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223: 1299; Jay et al., *J. Biol. Chem.* (1984) 259:6311; Stemmer, W. P. C., (1995) *Gene* 164:49-53.

Next, the gene sequence encoding the desired antigen can be inserted into a vector containing a synthetic Gag or synthetic Env expression cassette of the present invention. The antigen is inserted into the synthetic Gag coding sequence such that when the combined sequence is expressed it results in the production of VLPs comprising the Gag polypeptide and the antigen of interest, e.g., Env (native or modified) or other antigen derived from HIV. Insertions can be made within the coding sequence or at either end of the coding sequence (5', amino terminus of the expressed Gag polypeptide; or 3', carboxy terminus of the expressed Gag polypeptide)(Wagner, R., et al., *Arch Virol.* 127:117-137, 1992; Wagner, R., et al., *Virology* 200:162-175, 1994; Wu, X., et al., *J. Virol.* 69(6):3389-3398, 1995; Wang, C-T., et al., *Virology* 200:524-534, 1994; Chazal, N., et al., *Virology* 68(1):111-122, 1994; Griffiths, J. C., et al., *J. Virol.* 67(6):3191-3198, 1993; Reicin, A. S., et al., *J. Virol.* 69(2):642-650, 1995).

Up to 50% of the coding sequences of p55Gag can be deleted without affecting the assembly to virus-like particles and expression efficiency (Borsetti, A., et al, *J. Virol.* 72(11): 9313-9317, 1998; Garnier, L., et al., *J Virol* 72(6):4667-4677, 1998; Zhang, Y., et al., *J Virol* 72(3):1782-1789, 1998; Wang, C., et al., *J Virol* 72(10): 7950-7959, 1998). In one embodiment of the present invention, immunogenicity of the high level expressing synthetic Gag expression cassettes can be increased by the insertion of different structural or non-structural HIV antigens, multiepitope cassettes, or cytokine sequences into deleted regions of Gag sequence. Such deletions may be generated following the teachings of the present invention and information available to one of ordinary skill in the art. One possible advantage of this approach, relative to using full-length sequences fused to heterologous polypeptides, can be higher expression/secretion efficiency of the expression product.

When sequences are added to the amino terminal end of Gag, the polynucletide can contain coding sequences at the 5' end that encode a signal for addition of a myristic moiety to the Gag-containing polypeptide (e.g., sequences that encode Met-Gly).

The ability of Gag-containing polypeptide constructs to form VLPs can be empirically determined following the teachings of the present specification.

Gag/antigen (e.g., Gag/Env) synthetic expression cassettes include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric antigen-coding gene sequences, encoding, e.g., multiple antigens/epitopes of interest, for example derived from more than one viral isolate.

Typically the antigen coding sequences precede or follow the synthetic coding sequence and the chimeric transcription unit will have a single open reading frame encoding both the antigen of interest and the synthetic Gag coding sequences. Alternatively, multi-cistronic cassettes (e.g., bi-cistronic cassettes) can be constructed allowing expression of multiple antigens from a single mRNA using the EMCV IRES, or the like.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic Gag/or Env/antigen coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.*

(1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Gag-polypeptide encoding expression cassette). For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, *Gene* (1994) 143:245-249; Gao et al., *Biochem. Biophys. Res. Commun.* (1994) 200:1201-1206; Gao and Huang, *Nuc. Acids Res.* (1993). 21:2867-2872; Chen et al., *Nuc. Acids Res.* (1994) 22:2114-2120; and U.S. Pat. No. 5,135,855.

A synthetic Gag- and/or Env-containing expression cassette of interest can also be delivered without a viral vector. For example, the synthetic expression cassette can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097: 1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Feigner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein antigen(s) can also be delivered in cochleate lipid compositions similar to those described by Papahadjopoulos et al., *Biochem. Biophys. Acta.* (1975) 394: 483-491. See, also, U.S. Pat. Nos. 4,663,161 and 4,871,488.

The synthetic expression cassette of interest may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, *Vaccine* 12:1503-1509, 1994; Bioject, Inc., Portland, Oreg.).

Recombinant vectors carrying a synthetic expression cassette of the present invention are formulated into compositions for delivery to the vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

2.4.2 Ex Vivo Delivery of the Synthetic Expression Cassettes of the Present Invention In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4$^+$ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4$^+$ cells), or can be isolated by the use of CD8 antibodies coupled to a solid support. CD4 lymphocytes from HIV-1 infected patients can be expanded ex vivo, before or after transduction as described by Wilson et. al. (1995) *J. Infect. Dis.* 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) *Exp. Hematol.* 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic expression cassette of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACS-Vantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Generation of Synthetic Expression Cassettes

A. Modification of HIV-1 Env, Gag, Pol Nucleic Acid Coding Sequences

The Pol coding sequences were selected from Type C strain AF110975. The Gag coding sequences were selected from the Type C strains AF110965 and AF110967. The Env coding sequences were selected from Type C strains AF110968 and AF110975. These sequences were manipulated to maximize expression of their gene products.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The coding sequences were modified to be comparable to codon usage found in highly expressed human genes.

Second, there are inhibitory (or instability) elements (INS) located within the coding sequences of the Gag and Gag-protease coding sequences (Schneider R, et al., *J. Virol.* 71(7): 4892-4903, 1997). RRE is a secondary RNA structure that interacts with the HIV encoded Rev-protein to overcome the expression down-regulating effects of the INS. To overcome the post-transcriptional activating mechanisms of RRE and Rev, the instability elements are inactivated by introducing multiple point mutations that do not alter the reading frame of the encoded proteins. FIGS. 5 and 6 (SEQ ID Nos: 3, 4, 20 and 21) show the location of some remaining INS in synthetic sequences derived from strains AF110965 and AF110967. The changes made to these sequences are boxed in the Figures. In FIGS. 5 and 6, the top line depicts a codon optimized sequence of Gag polypeptides from the indicated strains. The nucleotide(s) appearing below the line in the boxed region(s) depicts changes made to further remove INS. Thus, when the changes indicated in the boxed regions are made, the resulting sequences correspond to the sequences depicted in FIGS. 1 and 2, respectively.

The synthetic coding sequences are assembled by methods known in the art, for example by companies such as the Midland Certified Reagent Company (Midland, Tex.).

In one embodiment of the invention, sequences encoding Pol-polypeptides are included with the synthetic Gag or Env sequences in order to increase the number of epitopes for virus-like particles expressed by the synthetic, optimized Gag/Env expression cassette. Because synthetic HIV-1 Pol expresses the functional enzymes reverse transcriptase (RT) and integrase (INT) (in addition to the structural proteins and protease), it may be helpful in some instances to inactivate RT and INT functions. Several deletions or mutations in the RT and INT coding regions can be made to achieve catalytic nonfunctional enzymes with respect to their RT and INT activity. {Jay. A. Levy (Editor) (1995) *The Retroviridae*, Plenum Press, New York. ISBN 0-306-45033X. Pages 215-20; Grimison, B. and Laurence, J. (1995), *Journal Of Acquired Immune Deficiency Syndromes and Human Retrovirology* 9(1):58-68; Wakefield, J. K., et al., (1992) *Journal Of Virology* 66(11):6806-6812; Esnouf, R., et al., (1995) *Nature Structural Biology* 2(4):303-308; Maignan, S., et al., (1998) *Journal Of Molecular Biology* 282(2):359-368; Katz, R. A. and Skalka, A. M. (1994) *Annual Review Of Biochemistry* 73 (1994); Jacobo-Molina, A., et al., (1993) *Proceedings Of the National Academy Of Sciences Of the United States Of America* 90(13):6320-6324; Hickman, A. B., et al., (1994) *Journal Of Biological Chemistry* 269(46):29279-29287; Goldgur, Y., et al., (1998) *Proceedings Of the National Academy Of Sciences Of the United States Of America* 95(16): 9150-9154; Goette, M., et al., (1998) *Journal Of Biological Chemistry* 273(17):10139-10146; Gorton, J. L., et al., (1998) *Journal of Virology* 72(6):5046-5055; Engelman, A., et al., (1997) *Journal Of Virology* 71(5):3507-3514; Dyda, F., et al., *Science* 266(5193):1981-1986; Davies, J. F., et al., (1991) *Science* 252(5002):88-95; Bujacz, G., et al., (1996) *Febs Letters* 398(2-3):175-178; Beard, W. A., et al., (1996) *Journal Of Biological Chemistry* 271(21):12213-12220; Kohlstaedt, L. A., et al., (1992) *Science* 256(5065):1783-1790; Krug, M. S, and Berger, S. L. (1991) *Biochemistry* 30(44):10614-10623; Mazumder, A., et al., (1996) *Molecular Pharmacology* 49(4): 621-628; Palaniappan, C., et al., (1997) *Journal Of Biological Chemistry* 272(17):11157-11164; Rodgers, D. W., et al., (1995) *Proceedings Of the National Academy Of Sciences Of the United States Of America* 92(4):1222-1226; Sheng, N. and Dennis, D. (1993) *Biochemistry* 32(18):4938-4942; Spence, R. A., et al., (1995) *Science* 267(5200):988-993}.

Furthermore selected B- and/or T-cell epitopes can be added to the Pol constructs (e.g., 3' of the truncated INT or within the deletions of the RT- and INT-coding sequence) to replace and augment any epitopes deleted by the functional modifications of RT and INT. Alternately, selected B- and T-cell epitopes (including CTL epitopes) from RT and INT can be included in a minimal VLP formed by expression of the synthetic Gag or synthetic Pol cassette, described above. (For descriptions of known HIV B- and T-cell epitopes see, HIV Molecular Immunology Database CTL Search Interface; Los Alamos Sequence Compendia, 1987-1997; Internet address: http://hiv-web.lanl.gov/immunology/index.html.)

The resulting modified coding sequences are presented as a synthetic Env expression cassette; a synthetic Gag expression cassette; a synthetic Pol expression cassette. A common Gag region (Gag-common) extends from nucleotide position 844 to position 903 (SEQ ID NO:1), relative to AF110965 (or from approximately amino acid residues 282 to 301 of SEQ ID NO:17) and from nucleotide position 841 to position 900 (SEQ ID NO:2), relative to AF110967 (or from approximately amino acid residues 281 to 300 of SEQ ID NO:22). A common Env region (Env-common) extends from nucleotide position 1213 to position 1353 (SEQ ID NO:5) and amino acid positions 405 to 451 of SEQ ID NO:23, relative to AF110968 and from nucleotide position 1210 to position 1353 (SEQ ID NO:11) and amino acid positions 404-451 (SEQ ID NO:24), relative to AF110975.

The synthetic DNA fragments for Pol, Gag and Env are cloned into the following eucaryotic expression vectors: pCMVKm2, for transient expression assays and DNA immunization studies, the pCMVKm2 vector is derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site is inserted into pCMVKm2 to generate pCMV-link; pESN2dhfr and pCMVPLEdhfr, for expression in Chinese Hamster Ovary (CHO) cells; and, pAcC13, a shuttle vector for use in the Baculovirus expression system (pAcC13, is derived from pAcC12 which is described by Munemitsu S., et al., *Mol Cell Biol.* 10(145977-5982, 1990).

Briefly, construction of pCMVPLEdhfr was as follows.

To construct a DHFR cassette, the EMCV IRES (internal ribosome entry site) leader was PCR-amplified from pCite-4a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser (SEQ ID NO: 46) spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/Neo(m2). Finally the bovine growth hormone terminator from pcDNA3 (Invitrogen, Inc., Carlsbad, Calif.) was inserted downstream of the neo gene to give pET-E-DHFR/Neo(m2)BGHt. The EMCV-dhfr/neo selectable marker cassette fragment was prepared by cleavage of pET-E-DHFR/Neo(m2)BGHt.

The CMV enhancer/promoter plus Intron A was transferred from pCMV6a (Chapman et al., *Nuc. Acids Res.* (1991) 19:3979-3986) as a HindIII-SalI fragment into pUC19 (New England Biolabs, Inc., Beverly, Mass.). The vector backbone of pUC19 was deleted from the NdeI to the Sapl sites. The above described DHFR cassette was added to the construct such that the EMCV IRES followed the CMV promoter. The vector also contained an ampr gene and an SV40 origin of replication.

B. Defining of the Major Homology Region (MHR) of HIV-1 p55Gag

The Major Homology Region (MHR) of HIV-1 p55 (Gag) is located in the p24-CA sequence of Gag. It is a conserved stretch of approximately 20 amino acids. The position in the wild type AF110965 Gag protein is from 282-301 (SEQ ID NO:25) and spans a region from 844-903 (SEQ ID NO:26) for the Gag DNA-sequence. The position in the synthetic Gag protein is also from 282-301 (SEQ ID NO:25) and spans a region from 844-903 (SEQ ID NO:1) for the synthetic Gag DNA-sequence. The position in the wild type and synthetic AF110967 Gag protein is from 281-300 (SEQ ID NO:27) and spans a region from 841-900 (SEQ ID NO:2) for the modified Gag DNA-sequence. Mutations or deletions in the MHR can severely impair particle production (Borsetti, A., et al., *J. Virol.* 72(11):9313-9317, 1998; Mammano, F., et al., *J Virol* 68(8):4927-4936, 1994).

Percent identity to this sequence can be determined, for example, using the Smith-Waterman search algorithm (Time Logic, Incline Village, NV), with the following exemplary parameters: weight matrix=nuc4×4hb; gap opening penalty=20, gap extension penalty=5.

C. Defining of the Common Sequence Region of HIV-1 Env

The common sequence region (CSR) of HIV-1 Env is located in the C4 sequence of Env. It is a conserved stretch of approximately 47 amino acids. The position in the wild type and synthetic AF110968 Env protein is from approximately amino acid residue 405 to 451 (SEQ ID NO:28) and spans a region from 1213 to 1353 (SEQ ID NO:5) for the Env DNA-sequence. The position in the wild type and synthetic AF110975 Env protein is from approximately amino acid residue 404 to 451 (SEQ ID NO:29) and spans a region from 1210 to 1353 (SEQ ID NO:11) for the Env DNA-sequence.

Percent identity to this sequence can be determined, for example, using the Smith-Waterman search algorithm (Time Logic, Incline Village, NV), with the following exemplary parameters: weight matrix=nuc4×4hb; gap opening penalty=20, gap extension penalty=5.

Various forms of the different embodiments of the invention, described herein, may be combined.

Example 2

Expression Assays for the Synthetic Coding Sequences

A. Env, Gag and Gag-Protease Coding Sequences

The wild-type Pol (from AF110975), Env (from AF110968 or AF110975) and Gag (from AF110965 and AF110967) sequences are cloned into expression vectors having the same features as the vectors into which the synthetic Pol, Env and Gag and sequences are cloned.

Expression efficiencies for various vectors carrying the wild-type and synthetic Pol, Env and Gag sequences are evaluated as follows. Cells from several mammalian cell lines (293, RD, COS-7, and CHO; all obtained from the American Type Culture Collection, 10801 University Boulevard, Manassas, Va. 20110-2209) are transfected with 2 μg of DNA in transfection reagent LT1 (PanVera Corporation, 545 Science Dr., Madison, Wis.). The cells are incubated for 5 hours in reduced serum medium (Opti-MEM, Gibco-BRL, Gaithersburg, Md.). The medium is then replaced with normal medium as follows: 293 cells, IMDM, 10% fetal'calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells are incubated for either 48 or 60 hours. Cell lysates are collected as described below in Example 3. Supernatants are harvested and filtered through 0.45 pm syringe filters. Supernatants are evaluated using the Coulter p24-assay (Coulter Corporation, Hialeah, Fla., US), using 96-well plates coated with a murine monoclonal antibody directed against HIV core antigen. The HIV-1 p24 antigen binds to the coated wells. Biotinylated antibodies against HIV recognize the bound p24 antigen. Conjugated strepavidin-horseradish peroxidase reacts with the biotin. Color develops from the reaction of peroxidase with TMB substrate. The reaction is terminated by addition of 4N $H_2SO_4$. The intensity of the color is directly proportional to the amount of HIV p24 antigen in a sample.

Synthetic Pol, Env, Gag expression cassettes provides dramatic increases in production of their protein products, relative to the native (wild-type Type C) sequences, when expressed in a variety of cell lines.

Example 3

Western Blot Analysis of Expression

A. Env, Gag and Pol Coding Sequences

Human 293 cells are transfected as described in Example 2 with pCMV6a-based vectors containing native or synthetic Pol, Env or Gag expression cassettes. Cells are cultivated for 60 hours post-transfection. Supernatants are prepared as described. Cell lysates are prepared as follows. The cells are washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. SDS-polyacrylamide gels (pre-cast 8-16%; Novex, San Diego, Calif.) are loaded with 20 µl of supernatant or 12.5 µl of cell lysate. A protein standard is also loaded (5 µl, broad size range standard; BioRad Laboratories, Hercules, Calif.). Electrophoresis is carried out and the proteins are transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer is performed at 100 volts for 90 minutes. The membranes are exposed to HIV-1-positive human patient serum and immunostained using o-phenylenediamine dihydrochloride (OPD; Sigma).

Immunoblotting analysis shows that cells containing the synthetic Pol, Env or Gag expression cassette produce the expected protein at higher per-cell concentrations than cells containing the native expression cassette. The proteins are seen in both cell lysates and supernatants. The levels of production are significantly higher in cell supernatants for cells transfected with the synthetic expression cassettes of the present invention.

In addition, supernatants from the transfected 293 cells are fractionated on sucrose gradients. Aliquots of the supernatant are transferred to Polyclear™ ultra-centrifuge tubes (Beckman Instruments, Columbia, Md.), under-laid with a solution of 20% (wt/wt) sucrose, and subjected to 2 hours centrifugation at 28,000 rpm in a Beckman SW28 rotor. The resulting pellet is suspended in PBS and layered onto a 20-60% (wt/wt) sucrose gradient and subjected to 2 hours centrifugation at 40,000 rpm in a Beckman SW41ti rotor.

The gradient is then fractionated into approximately 10×1 ml aliquots (starting at the top, 20%-end, of the gradient). Samples are taken from fractions 1-9 and are electrophoresed on 8-16% SDS polyacrylamide gels. The supernatants from 293/synthetic Pol, Env or Gag cells give much stronger bands than supernatants from 293/native Pol, Env or Gag cells.

Example 4

In Vivo Immunogenicity of Synthetic Pol, Gag and Env Expression Cassettes

A. Immunization

To evaluate the possibly improved immunogenicity of the synthetic Pol, Gag and Env expression cassettes, a mouse study is performed. The plasmid DNA, pCMVKM2 carrying the synthetic Gag expression cassette, is diluted to the following final concentrations in a total injection volume of 100 µl: 20 µg, 2 µg, 0.2 µg, 0.02 and 0.002 µg. To overcome possible negative dilution effects of the diluted DNA, the total DNA concentration in each sample is brought up to 20 µg using the vector (pCMVKM2) alone. As a control, plasmid DNA of the native Gag expression cassette is handled in the same manner. Twelve groups of four to ten Balb/c mice (Charles River, Boston, Mass.) are intramuscularly immunized (50 µl per leg, intramuscular injection into the tibialis anterior) according to the schedule in Table 1.

TABLE 1

| Group | Gag or Env Expression Cassette | Concentration of Gag or Env plasmid DNA (µg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |
| 11 | Native | 20 | 0, 4 |
| 12 | Native | 2 | 0, 4 |
| 13 | Native | 0.2 | 0, 4 |
| 14 | Native | 0.02 | 0, 4 |
| 15 | Native | 0.002 | 0, 4 |
| 16 | Native | 20 | 0 |
| 17 | Native | 2 | 0 |
| 18 | Native | 0.2 | 0 |
| 19 | Native | 0.02 | 0 |
| 20 | Native | 0.002 | 0 |

[1] = initial immunization at "week 0"

Groups 1-5 and 11-15 are bled at week 0 (before immunization), week 4, week 6, week 8, and week 12. Groups 6-20 and 16-20 are bled at week 0 (before immunization) and at week 4.

B. Humoral Immune Response

The humoral immune response is checked with an anti-HIV Pol, Gag or Env antibody ELISAs (enzyme-linked immunosorbent assays) of the mice sera 0 and 4 weeks post immunization (groups 5-12) and, in addition, 6 and 8 weeks post immunization, respectively, 2 and 4 weeks post second immunization (groups 1-4).

The antibody titers of the sera are determined by anti-Pol, anti-Gag or anti-Env antibody ELISA. Briefly, sera from immunized mice are screened for antibodies directed against the HIV p55 Gag protein, an Env protein, e.g., gp160 or gp120 or a Pol protein, e.g., p6, prot or RT. ELISA microtiter plates are coated with 0.2 µg of Pol, Gag or Env protein per well overnight and washed four times; subsequently, blocking is done with PBS-0.2% Tween (Sigma) for 2 hours. After removal of the blocking solution, 100 µl of diluted mouse serum is added. Sera are tested at 1/25 dilutions and by serial 3-fold dilutions, thereafter. Microtiter plates are washed four times and incubated with a secondary, peroxidase-coupled anti-mouse IgG antibody (Pierce, Rockford, Ill.). ELISA plates are washed and 100 µl of 3, 3', 5, 5'-tetramethyl benzidine (TMB; Pierce) is added per well. The optical density of each well is measured after 15 minutes. The titers reported are the reciprocal of the dilution of serum that gave a half-maximum optical density (O.D.).

Synthetic expression cassettes will provide a clear improvement of immunogenicity relative to the native expression cassettes.

C. Cellular Immune Response

The frequency of specific cytotoxic T-lymphocytes (CTL) is evaluated by a standard chromium release assay of peptide pulsed mouse (Balb/c, CB6F1 and/or C3H) CD4 cells. Pol, Gag or Env expressing vaccinia virus infected CD-8 cells are used as a positive control. Briefly, spleen cells (Effector cells, E) are obtained from the mice immunized as described above are cultured, restimulated, and assayed for CTL activity against Gag peptide-pulsed target cells as described (Doe, B., and Walker, C. M., *AIDS* 10(7):793-794, 1996). Cytotoxic activity is measured in a standard $^{51}$Cr release assay. Target (T) cells are cultured with effector (E) cells at various E:T ratios for 4 hours and the average cpm from duplicate wells are used to calculate percent specific $^{51}$Cr release.

Cytotoxic T-cell (CTL) activity is measured in splenocytes recovered from the mice immunized with HIV Gag or Env DNA. Effector cells from the Gag or Env DNA-immunized animals exhibit specific lysis of Pol, Gag or Env peptide-pulsed SV-BALB (MHC matched) targets cells, indicative of a CTL response. Target cells that are peptide-pulsed and derived from an MHC-unmatched mouse strain (MC57) are not lysed.

Thus, synthetic Pol, Env and Gag expression cassettes exhibit increased potency for induction of cytotoxic T-lymphocyte (CTL) responses by DNA immunization.

Example 5

DNA-immunization of Non-Human Primates Using a Synthetic Pol, Env or Gag Expression Cassette Non-human primates are immunized multiple times (e.g., weeks 0, 4, 8 and 24) intradermally, mucosally or bilaterally, intramuscular, into the quadriceps using various doses (e.g., 1-5 mg) synthetic Pol, Gag- and/or Env-containing plasmids. The animals are bled two weeks after each immunization and ELISA is performed with isolated plasma. The ELISA is performed essentially as described in Example 4 except the second antibody-conjugate is an anti-human IgG, g-chain specific, peroxidase conjugate (Sigma Chemical Co., St. Louis, Md. 63178) used at a dilution of 1:500. Fifty µg/ml yeast extract is added to the dilutions of plasma samples and antibody conjugate to reduce non-specific background due to preexisting yeast antibodies in the non-human primates.

Further, lymphoproliferative responses to antigen can also be evaluated post-immunization, indicative of induction of T-helper cell functions.

Synthetic Pol, Env and Gag plasmid DNA are expected to be immunogenic in non-human primates.

Example 6

In Vitro Expression of Recombinant Sindbis RNA and DNA Containing the Synthetic Pol, Env and Gag Expression Cassette To evaluate the expression efficiency of the synthetic Pol, Env and Gag expression cassette in Alphavirus vectors, the selected synthetic expression cassette is subcloned into both plasmid DNA-based and recombinant vector particle-based Sindbis virus vectors. Specifically, a cDNA vector construct for in vitro transcription of Sindbis virus RNA vector replicons (pRSIN-luc; Dubensky, et al., *J. Virol.* 70:508-519, 1996) is modified to contain a PmeI site for plasmid linearization and a polylinker for insertion of heterologous genes. A polylinker is generated using two oligonucleotides that contain the sites XhoI, PmlI, ApaI, NarI, XbaI, and NotI (XPANXNF, and XPANXNR).

The plasmid pRSIN-luc (Dubensky et al., supra) is digested with XhoI and NotI to remove the luciferase gene insert, blunt-ended using Klenow and dNTPs, and purified from an agarose get using GeneCleanII (Bio101, Vista, Calif.). The oligonucleotides are annealed to each other and ligated into the plasmid. The resulting construct is digested with NotI and SacI to remove the minimal Sindbis 3'-end sequence and $A_{40}$ tract, and ligated with an approximately 0.4 kbp fragment from PKSSIN1-BV (WO 97/38087). This 0.4 kbp fragment is obtained by digestion of pKSSIN1-BV with NotI and Sad, and purification after size fractionation from an agarose gel. The fragment contains the complete Sindbis virus 3'-end, an $A_{40}$ tract and a PmeI site for linearization. This new vector construct is designated SINBVE.

The synthetic HIV Pol, Gag and Env coding sequences are obtained from the parental plasmid by digestion with EcoRI, blunt-ending with Klenow and dNTPs, purification with GeneCleanII, digestion with SalI, size fractionation on an agarose gel, and purification from the agarose gel using GeneCleanII. The synthetic Pol, Gag or Env coding fragment is ligated into the SINBVE vector that is digested with XhoI and PmtI. The resulting vector is purified using GeneCleanII and is designated SINBVGag. Vector RNA replicons may be transcribed in vitro (Dubensky et al., supra) from SINBVGag and used directly for transfection of cells. Alternatively, the replicons may be packaged into recombinant vector particles by co-transfection with defective helper RNAs or using an alphavirus packaging cell line.

The DNA-based Sindbis virus vector pDCMVSIN-beta-gal (Dubensky, et al., *J. Virol.* 70:508-519, 1996) is digested with SalI and XbaI, to remove the beta-galactosidase gene insert, and purified using GeneCleanII after agarose gel size fractionation. The HIV Gag or Env gene is inserted into the pDCMVSIN-beta-gal by digestion of SINBVGag with SalI and XhoI, purification using GeneCleanII of the Gag-containing fragment after agarose gel size fractionation, and ligation. The resulting construct is designated pDSIN-Gag, and may be used directly for in vivo administration or formulated using any of the methods described herein.

BHK and 293 cells are transfected with recombinant Sindbis RNA and DNA, respectively. The supernatants and cell lysates are tested with the Coulter capture ELISA (Example 2).

BHK cells are transfected by electroporation with recombinant Sindbis RNA.

293 cells are transfected using LT-1 (Example 2) with recombinant Sindbis DNA. Synthetic Gag- and/or Env-containing plasmids are used as positive controls. Supernatants and lysates are collected 48 h post transfection.

Pol, Gag and Env proteins can be efficiently expressed from both DNA and RNA-based Sindbis vector systems using the synthetic expression cassettes.

Example 7

In Vivo Immunogenicity of Recombinant Sindbis Replicon Vectors Containing Synthetic Pol, Gag and/or Env Expression Cassettes A. Immunization To evaluate the immunogenicity of recombinant synthetic Pol, Gag and Env expression cassettes in Sindbis replicons, a mouse study is performed. The Sindbis virus DNA vector carrying the synthetic Pol, Gag and/or Env expression cassette (Example 6), is diluted to the following final concentrations in a total injection volume of 100 µl: 20 µg, 2 µg, 0.2 µg, 0.02 and 0.002 µg. To overcome possible negative dilution effects of the diluted DNA, the total DNA concentration in each sample is brought up to 20 µg using the Sindbis replicon vector DNA alone. Twelve groups of four to ten Balb/c mice (Charles River, Boston, Mass.) are intramuscularly immunized (50 μl per leg, intramuscular injection into the tibialis anterior) according to the schedule in Table 2. Alternatively, Sindbis viral particles are prepared at the following doses: $10^3$ pfu, $10^5$ pfu and 10' pfu in 100 as shown in Table 3. Sindbis Pol, Env or Gag particle preparations are administered to mice using intramuscular and subcutaneous routes (50 μl per site).

TABLE 2

| Group | Gag or Env Expression Cassette | Concentration of Gag or Env DNA (μg) | Immunized at time (weeks): |
|---|---|---|---|
| 1 | Synthetic | 20 | $0^1$, 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |

$^1$= initial immunization at "week 0"

TABLE 3

| Group | Gag or Env sequence | Concentration of viral particle (pfu) | Immunized at time (weeks): |
|---|---|---|---|
| 1 | Synthetic | $10^3$ | $0^1$, 4 |
| 2 | Synthetic | $10^5$ | 0, 4 |
| 3 | Synthetic | $10^7$ | 0, 4 |
| 8 | Synthetic | $10^3$ | 0 |
| 9 | Synthetic | $10^5$ | 0 |
| 10 | Synthetic | $10^7$ | 0 |

$^1$= initial immunization at "week 0"

Groups are bled and assessment of both humoral and cellular (e.g., frequency of specific CTLs) is performed, essentially as described in Example 4.

Example 8

Identification and Sequencing of a Novel HIV Type C Variants

A full-length clone, called 8_5_ZA, encoding an HIV Type C was isolated and sequenced. Briefly, genomic DNA from HIV-1 subtype C infected South African patients was isolated from PBMC (peripheral blood mononuclear cells) by alkaline lysis and anion-exchange columns (Quiagen). To get the genome of full-length clones two halves were amplified, that could later be joined together in frame within the Pol region using an unique Sal 1 site in both fragments. For the amplification, 200-800 ng of genomic DNA were added to the buffer and enzyme mix of the Expand Long Template PCR System after the protocol of the manufacturer (Boehringer Mannheim). The primer were designed after alignments of known full length sequences. For the 5' half a primer mix of 2 forward primers containing either thymidine (S1FCSacTA 5'-GTTTCTTGAGCTCTGGAAGGGTTAATTTAC TCCAAGAA-3', SEQ ID NO:38) or cytosine on position 20 (S1FTSacTA 5'-GTTTCTTGAGCTCTGGAAGGGT-TAATTTACTCTAAGAA, SEQ ID NO:39) plus Sal 1 site, were used. The reverse primer were also a mix of two primers with either thymidine or cytosine on position 13 (S145RTSalTA 5'-GTTTCTTGTCGACTTGTCCATG-TATGGCTTCCCC T-3', SEQ ID NO:40 and S145RCSalTA 5'-GTTTCTTGTCGACTTGTCCATGCATGGCTTCCCT-3' SEQ ID NO:41) and contained a Sal 1 site. The forward primer for the 3' half was also a mixture of two primers (S245FASalTA 5'-GTTTCTTGTCGACTGTAGTCCAG-GaATATGGCAAT TAG-3' SEQ ID NO:42 and S245FGSalTA 5'-GTTTCTTGTCGACTGTAGTCCAGG-gATATG GCAA TTAG-3' SEQ ID NO:43) with Sal 1 site and adenine or guanine on position 12. The reverse primer had a Not 1 site (S2_FullNotTA 5'-GTTTCTTGCGGCCGCT-GCTAGA GATTTTCCACACTACCA-3' SEQ ID NO:44). After amplification the PCR products were purified using a 1% agarose gel and cloned into the pCR-XL-TOPO vector via TA cloning (Invitrogen). Colonies were checked by restriction analysis and sequence verified. For the full length sequence the sequences of the 5'- and 3' half were combined. The sequence is shown in SEQ ID NO:33. Furthermore, important domains are shown in Table A.

Another clone, designated 12_5/1ZA was also sequenced and is shown in SEQ ID NO:45.

As described in Example 1, synthetic expression cassettes are generated using one or more polynucleotide sequence obtained from 8_5_ZA or 12_5/1ZA.

Although preferred embodiments of the subject invention have been described in some detail, it is understood that obvious variations can be made without departing from the spirit and the scope of the invention as defined by the appended claims.

SEQUENCE LISTING

<160> NUMBER OF SEQ ID NOS: 46

<210> SEQ ID NO 1
<211> LENGTH: 60
<212> TYPE: DNA
<213> ORGANISM: Human immunodeficiency virus

<400> SEQUENCE: 1
gacatcaagc agggccccaa ggagcccttc cgcgactacg tggaccgctt cttcaagacc    60

<210> SEQ ID NO 2
<211> LENGTH: 60
<212> TYPE: DNA
<213> ORGANISM: Human immunodeficiency virus

<400> SEQUENCE: 2

```
gacatccgcc agggccccaa ggagcccttc gcgactacg tggaccgctt cttcaagacc    60
```

<210> SEQ ID NO 3
<211> LENGTH: 1479
<212> TYPE: DNA
<213> ORGANISM: Artificial Sequence
<220> FEATURE:
<223> OTHER INFORMATION: Description of Artificial Sequence: synthetic
      Gag of HIV strain AF110965

<400> SEQUENCE: 3

```
atgggcgccc cgccagcat cctgcgcggc ggcaagctgg acgcctggga gcgcatccgc      60
ctgcgccccg gcggcaagaa gtgctacatg atgaagcacc tggtgtgggc cagccgcgag    120
ctggagaagt tcgccctgaa ccccggcctg ctggagacca gcgagggctg caagcagatc    180
atccgccagc tgcaccccgc cctgcagacc ggcagcgagg agctgaagag cctgttcaac    240
accgtggcca ccctgtactg cgtgcacgag aagatcgagg tccgcgacac caaggaggcc    300
ctggacaaga tcgaggagga gcagaacaag tgccagcaga gatccagca ggccgaggcc    360
gccgacaagg caaggtgag ccagaactac cccatcgtgc agaacctgca gggccagatg    420
gtgcaccagg ccatcagccc ccgcaccctg aacgcctggg tgaaggtgat cgaggagaag    480
gccttcagcc ccgaggtgat ccccatgttc accgccctga gcgagggcgc caccccccag    540
gacctgaaca cgatgttgaa caccgtgggc ggccaccagg ccgccatgca gatgctgaag    600
gacaccatca cgaggaggc cgccgagtgg accgcgtgc accccgtgca cgccggcccc    660
atcgcccccg ccagatgcg cgagcccgc ggcagcgaca tcgccggcac caccagcacc    720
ctgcaggagc agatcgcctg gatgaccagc aaccccccca tccccgtggg cgacatctac    780
aagcggtgga tcatcctggg cctgaacaag atcgtgcgga tgtacagccc cgtgagcatc    840
ctggacatca gcagggccc caaggagccc ttccgcgact acgtggaccg cttcttcaag    900
accctgcgcg ccgagcagag caccaggag gtgaagaact ggatgaccga caccctgctg    960
gtgcagaacg ccaaccccga ctgcaagacc atcctgcgcg ctctcggccc cggcgccagc   1020
ctggaggaga tgatgaccgc ctgccagggc gtggcggcc ccagccacaa ggcccgcgtg   1080
ctggccgagg cgatgagcca ggccaacacc agcgtgatga tgcagaagag caacttcaag   1140
ggccccggc gcatcgtcaa gtgcttcaac tgcggcaagg agggcacat cgcccgcaac   1200
tgccgcgccc ccgcaagaa gggctgctgg aagtgcggca aggagggcca ccagatgaag   1260
gactgcaccg agcgccaggc caacttcctg ggcaagatct ggcccagcca aagggccgc   1320
cccggcaact tcctgcagag ccgccccgag cccaccgccc ccccgccga gcttccgc     1380
ttcgaggaga ccaccccgg ccagaagcag gagagcaagg accgcgagac cctgaccagc   1440
ctgaagagcc tgttcggcaa cgacccctg agccagtaa                          1479
```

<210> SEQ ID NO 4
<211> LENGTH: 1509
<212> TYPE: DNA
<213> ORGANISM: Artificial Sequence
<220> FEATURE:
<223> OTHER INFORMATION: Description of Artificial Sequence: synthetic
      Gag of HIV strain AF110967

<400> SEQUENCE: 4

```
atgggcgccc cgccagcat cctgcgcggc gagaagctgg acaagtggga gaagatccgc     60
ctgcgccccg gcggcaagaa gcactacatg ctgaagcacc tggtgtgggc cagccgcgag   120
ctggagggct tcgccctgaa ccccggcctg ctggagaccg ccgagggctg caagcagatc   180
```

```
atgaagcagc tgcagcccgc cctgcagacc ggcaccgagg agctgcgcag cctgtacaac    240
accgtggcca ccctgtactg cgtgcacgcc ggcatcgagg tccgcgacac caaggaggcc    300
ctggacaaga tcgaggagga gcagaacaag tcccagcaga agacccagca ggccaaggag    360
gccgacggca aggtgagcca gaactacccc atcgtgcaga acctgcaggg ccagatggtg    420
caccaggcca tcagccccg cacccctgaac gcctgggtga aggtgatcga ggagaaggcc    480
ttcagccccg aggtgatccc catgttcacc gccctgagcg agggcgccac cccccaggac    540
ctgaacacga tgttgaacac cgtgggcggc caccaggccg ccatgcagat gctgaaggac    600
accatcaacg aggaggccgc cgagtgggac cgcctgcacc ccgtgcaggc cggccccgtg    660
gcccccggcc agatgcgcga cccccgcggc agcgacatcg ccggcgccac cagcaccctg    720
caggagcaga tcgcctggat gaccagcaac cccccgtgc ccgtgggcga catctacaag    780
cggtggatca tcctgggcct gaacaagatc gtgcggatgt acagcccgt gagcatcctg    840 gacatccgcc agggccccaa ggagcccttc gcgactacg tggaccgctt cttcaagacc    900
ctgcgcgccg agcaggccac ccaggacgtg aagaactgga tgaccgagac cctgctggtg    960
cagaacgcca ccccgactg caagaccatc ctgcgcgctc tcggcccgg cgccaccctg    1020 gaggagatga tgaccgcctg ccagggcgtg ggcggccccg ccacaaggc ccgcgtgctg    1080 gccgaggcga tgagccaggc caacagcgtg aacatcatga tgcagaagag caacttcaag    1140
ggcccccggc gcaacgtcaa gtgcttcaac tgcggcaagg agggccacat cgccaagaac    1200
tgccgcgccc cccgcaagaa gggctgctgg aagtgcggca aggagggcca ccagatgaag    1260
gactgcaccg agcgccaggc caacttcctg ggcaagatct ggcccagcca aagggccgc    1320 cccggcaact tcctgcagaa ccgcagcgag cccgccgccc ccaccgtgcc caccgccccc    1380
cccgccgaga gcttccgctt cgaggagacc accccgccc caagcagga gcccaaggac    1440 cgcgagccct accgcgagcc cctgaccgcc ctgcgcagcc tgttcggcag cggccccctg    1500
agccagtaa                                                          1509

<210> SEQ ID NO 5
<211> LENGTH: 141
<212> TYPE: DNA
<213> ORGANISM: Artificial Sequence
<220> FEATURE:
<223> OTHER INFORMATION: Description of Artificial Sequence: Env common
      region of HIV strain AF110968

<400> SEQUENCE: 5
accatcacca tcacctgccg catcaagcag atcatcaaca tgtggcagaa ggtgggccgc    60
gccatgtacg cccccccat cgccggcaac ctgacctgcg agagcaacat caccggcctg    120
ctgctgaccc gcgacggcgg c                                              141

<210> SEQ ID NO 6
<211> LENGTH: 1431
<212> TYPE: DNA
<213> ORGANISM: Artificial Sequence
<220> FEATURE:
<223> OTHER INFORMATION: Description of Artificial Sequence: synthetic
      gp120 coding region of HIV strain AF110968

<400> SEQUENCE: 6
agcgtggtgg gcaacctgtg ggtgaccgtg tactacggcg tgcccgtgtg ga

```
gtgaccgaga acttcaacat gtggaagaac gacatggtgg accagatgca cgaggacatc      240
atcagcctgt gggaccagag cctgaagccc tgcgtgaagc tgacccccct gtgcgtgacc      300
ctgaagtgcc gcaacgtgaa cgccaccaac aacatcaaca gcatgatcga caacagcaac      360
aagggcgaga tgaagaactg cagcttcaac gtgaccaccg agctgcgcga ccgcaagcag      420
gaggtgcacg ccctgttcta ccgcctggac gtggtgcccc tgcagggcaa caacagcaac      480
gagtaccgcc tgatcaactg caacaccagc gccatcaccc aggcctgccc caaggtgagc      540
ttcgacccca tccccatcca ctactgcacc ccgccggct acgccatcct gaagtgcaac       600
aaccagacct tcaacggcac cggcccctgc aacaacgtga gcagcgtgca gtgcgcccac      660
ggcatcaagc ccgtggtgag cacccagctg ctgctgaacg gcagcctggc caagggcgag      720
atcatcatcc gcagcgagaa cctggccaac aacgccaaga tcatcatcgt gcagctgaac      780
aagcccgtga agatcgtgtg cgtgcgcccc aacaacaaca cccgcaagag cgtgcgcatc      840 ggcccccggcc agaccttcta cgccaccggc gagatcatcg cgacatccg ccaggcctac      900 tgcatcatca acaagaccga gtggaacagc accctgcagg gcgtgagcaa gaagctggag      960
gagcacttca gcaagaaggc catcaagttc gagcccagca gcggcggcga cctggagatc     1020
accacccaca gcttcaactg ccgcggcgag ttcttctact gcgacaccag ccagctgttc     1080
aacagcacct acagccccag cttcaacggc accgagaaca gctgaacgg caccatcacc      1140 atcacctgcc gcatcaagca gatcatcaac atgtggcaga aggtgggccg cgccatgtac     1200
gcccccccca tcgccggcaa cctgacctgc gagagcaaca tcaccggcct gctgctgacc     1260
cgcgacggcg gcaagaccgg ccccaacgac accgagatct ccgcccccgg cggcggcgac     1320
atgcgcgaca ctggcgcaa cgagctgtac aagtacaagg tggtggagat caagcccctg      1380
ggcgtggccc ccaccgaggc caagcgccgc gtggtggagc gcgagaagcg c             1431
```

<210> SEQ ID NO 7
<211> LENGTH: 1944
<212> TYPE: DNA
<213> ORGANISM: Artificial Sequence
<220> FEATURE:
<223> OTHER INFORMATION: Description of Artificial Sequence: synthetic
      gp140 coding region of HIV strain AF110968

<400> SEQUENCE: 7

```
agcgtggtgg gcaacctgtg ggtgaccgtg tactacggcg tgcccgtgtg aaggaggcc       60 aagaccaccc tgttctgcac cagcgacgcc aaggcctacg agaccgaggt gcacaacgtg     120
tgggccaccc acgcctgcgt gcccaccgac cccaaccccc aggagatcgt gctggagaac     180
gtgaccgaga acttcaacat gtggaagaac gacatggtgg accagatgca cgaggacatc    240
atcagcctgt gggaccagag cctgaagccc tgcgtgaagc tgacccccct gtgcgtgacc    300
ctgaagtgcc gcaacgtgaa cgccaccaac aacatcaaca gcatgatcga caacagcaac    360
aagggcgaga tgaagaactg cagcttcaac gtgaccaccg agctgcgcga ccgcaagcag    420
gaggtgcacg ccctgttcta ccgcctggac gtggtgcccc tgcagggcaa caacagcaac    480
gagtaccgcc tgatcaactg caacaccagc gccatcaccc aggcctgccc caaggtgagc    540
ttcgacccca tccccatcca ctactgcacc ccgccggct acgccatcct gaagtgcaac     600
aaccagacct tcaacggcac cggcccctgc aacaacgtga gcagcgtgca gtgcgcccac    660
ggcatcaagc ccgtggtgag cacccagctg ctgctgaacg gcagcctggc caagggcgag    720
atcatcatcc gcagcgagaa cctggccaac aacgccaaga tcatcatcgt gcagctgaac    780
```

-continued

| | |
|---|---|
| aagcccgtga agatcgtgtg cgtgcgcccc aacaacaaca cccgcaagag cgtgcgcatc | 840 |
| ggcccccggcc agaccttcta cgccaccggc gagatcatcg gcgacatccg ccaggcctac | 900 |
| tgcatcatca acaagaccga gtggaacagc accctgcagg gcgtgagcaa gaagctggag | 960 |
| gagcacttca gcaagaaggc catcaagttc gagcccagca cgcggcggcga cctggagatc | 1020 |
| accacccaca gcttcaactg ccgcggcgag ttcttctact gcgacaccag ccagctgttc | 1080 |
| aacagcacct acagcccag cttcaacggc accgagaaca agctgaacgg caccatcacc | 1140 |
| atcacctgcc gcatcaagca gatcatcaac atgtggcaga aggtgggccg cgccatgtac | 1200 |
| gccccccca tcgccggcaa cctgacctgc gagagcaaca tcaccggcct gctgctgacc | 1260 |
| cgcgacggcg gcaagaccgg ccccaacgac accgagatct ccgccccgg cggcggcgac | 1320 |
| atgcgcgaca ctggcgcaa cgagctgtac aagtacaagg tggtggagat caagcccctg | 1380 |
| ggcgtggccc ccaccgaggc caagcgccgc gtggtggagc gcgagaagcg cgccgtgggc | 1440 |
| atcgcgcgcc tgttcctggg cttcctgggc gccgccggca gcaccatggg cgccgccagc | 1500 |
| atcaccctga ccgtgcaggc ccgcctgctg ctgagcggca tcgtgcagca gcagaacaac | 1560 |
| ctgctgcgcg ccatcgaggc ccagcagcac ctgctgcagc tgaccgtgtg ggcatcaag | 1620 |
| cagctgcaga cccgcatcct ggccgtggag cgctacctga aggaccagca gctgctgggc | 1680 |
| atctggggct gcagcggcaa gctgatctgc accaccgccg tgccctggaa cagcagctgg | 1740 |
| agcaaccgca gccacgacga gatctgggac aacatgacct ggatgcagtg ggaccgcgag | 1800 |
| atcaacaact acaccgacac catctaccgc ctgctggagg agagccagaa ccagcaggag | 1860 |
| aagaacgaga aggacctgct ggccctggac agctggcaga acctgtggaa ctggttcagc | 1920 |
| atcaccaact ggctgtggta catc | 1944 |

<210> SEQ ID NO 8
<211> LENGTH: 2466
<212> TYPE: DNA
<213> ORGANISM: Artificial Sequence
<220> FEATURE:
<223> OTHER INFORMATION: Description of Artificial Sequence: synthetic
  gp160 coding region of HIV strain AF110968

<400> SEQUENCE: 8

| | |
|---|---|
| agcgtggtgg gcaacctgtg ggtgaccgtg tactacggcg tgcccgtgtg gaaggaggcc | 60 |
| aagaccaccc tgttctgcac cagcgacgcc aaggcctacg agaccgaggt gcacaacgtg | 120 |
| tgggccaccc acgcctgcgt gcccaccgac cccaaccccc aggagatcgt gctggagaac | 180 |
| gtgaccgaga acttcaacat gtggaagaac gacatggtgg accagatgca cgaggacatc | 240 |
| atcagcctgt gggaccagag cctgaagccc tgcgtgaagc tgaccccccct gtgcgtgacc | 300 |
| ctgaagtgcc gcaacgtgaa cgccaccaac aacatcaaca gcatgatcga caacagcaac | 360 |
| aagggcgaga tgaagaactg cagcttcaac gtgaccaccg agctgcgcga ccgcaagcag | 420 |
| gaggtgcacg ccctgttcta ccgcctggac gtggtgcccc tgcagggcaa caacagcaac | 480 |
| gagtaccgcc tgatcaactg caacaccagc gccatcaccc aggcctgccc caaggtgagc | 540 |
| ttcgacccca tccccatcca ctactgcacc cccgccggct acgccatcct gaagtgcaac | 600 |
| aaccagacct tcaacggcac cggccccctg aacaacgtga gcagcgtgca gtgcgcccac | 660 |
| ggcatcaagc ccgtggtgag cacccagctg ctgctgaacg gcagcctggc caagggcgag | 720 |
| atcatcatcc gcagcgagaa cctggccaac aacgccaaga tcatcatcgt gcagctgaac | 780 |
| aagcccgtga gatcgtgtg cgtgcgcccc aacaacaaca cccgcaagag cgtgcgcatc | 840 |
| ggcccccggcc agaccttcta cgccaccggc gagatcatcg gcgacatccg ccaggcctac | 900 |

| | |
|---|---|
| tgcatcatca acaagaccga gtggaacagc accctgcagg gcgtgagcaa gaagctggag | 960 |
| gagcacttca gcaagaaggc catcaagttc gagcccagca gcggcggcga cctggagatc | 1020 |
| accacccaca gcttcaactg ccgcggcgag ttcttctact gcgacaccag ccagctgttc | 1080 |
| aacagcacct acagccccag cttcaacggc accgagaaca agctgaacgg caccatcacc | 1140 |
| atcacctgcc gcatcaagca gatcatcaac atgtggcaga aggtgggccg cgccatgtac | 1200 |
| gccccccca tcgccggcaa cctgacctgc gagagcaaca tcaccggcct gctgctgacc | 1260 |
| cgcgacggcg gcaagaccgg ccccaacgac accgagatct ccgcccccgg cggcggcgac | 1320 |
| atgcgcgaca actggcgcaa cgagctgtac aagtacaagg tggtggagat caagcccctg | 1380 |
| ggcgtggccc ccaccgaggc caagcgccgc gtggtggagc gcgagaagcg cgccgtgggc | 1440 |
| atcggcgccg tgttcctggg cttcctgggc gccgccggca gcaccatggg cgccgccagc | 1500 |
| atcaccctga ccgtgcaggc ccgcctgctg ctgagcggca tcgtgcagca gcagaacaac | 1560 |
| ctgctgcgcg ccatcgaggc ccagcagcac ctgctgcagc tgaccgtgtg gggcatcaag | 1620 |
| cagctgcaga cccgcatcct ggccgtggag cgctacctga aggaccagca gctgctgggc | 1680 |
| atctggggct gcagcggcaa gctgatctgc accaccgccg tgccctggaa cagcagctgg | 1740 |
| agcaaccgca gccacgacga gatctgggac aacatgacct ggatgcagtg ggaccgcgag | 1800 |
| atcaacaact acaccgacac catctaccgc ctgctggagg agagccagaa ccagcaggag | 1860 |
| aagaacgaga aggacctgct ggccctggac agctggcaga acctgtggaa ctggttcagc | 1920 |
| atcaccaact ggctgtggta catcaagatc ttcatcatga tcgtgggcgg cctgatcggc | 1980 |
| ctgcgcatca tcttcgccgt gctgagcatc gtgaaccgcg tgcgccaggg ctacagcccc | 2040 |
| ctgcccttcc agaccctgac ccccaacccc gcgagcccg accgcctggg ccgcatcgag | 2100 |
| gaggagggcg gcgagcagga ccgcggccgc agcatccgcc tggtgagcgg cttcctggcc | 2160 |
| ctggcctggg acgacctgcg cagcctgtgc ctgttcagct accaccgcct gcgcgacttc | 2220 |
| atcctgatcg ccgcccgcgt gctggagctg ctgggccagc gcggctggga ggccctgaag | 2280 |
| tacctgggca gcctggtgca gtactgggc ctggagctga agaagagcgc catcagcctg | 2340 |
| ctggacacca tcgccatcgc cgtggccgag ggcaccgacc gcatcatcga gttcatccag | 2400 |
| cgcatctgcc gcgccatccg caacatcccc cgccgcatcc gccagggctt cgaggccgcc | 2460 |
| ctgcag | 2466 |

<210> SEQ ID NO 9
<211> LENGTH: 2547
<212> TYPE: DNA
<213> ORGANISM: Artificial Sequence
<220> FEATURE:
<223> OTHER INFORMATION: Description of Artificial Sequence: synthetic
    signal sequence and gp160 coding region of HIV
    strain AF110968

<400> SEQUENCE: 9

| | |
|---|---|
| atgcgcgtga tgggcatcct gaagaactac cagcagtggt ggatgtgggg catcctgggc | 60 |
| ttctggatgc tgatcatcag cagcgtggtg ggcaacctgt gggtgaccgt gtactacggc | 120 |
| gtgcccgtgt ggaaggaggc caagaccacc ctgttctgca ccagcgacgc caaggcctac | 180 |
| gagaccgagt gcacaacgt gtgggccacc cacgcctgcg tgcccaccga ccccaacccc | 240 |
| caggagatcg tgctggagaa cgtgaccgag aacttcaaca tgtggaagaa cgacatggtg | 300 |
| gaccagatga cgaggacat catcagcctg tgggaccaga gcctgaagcc ctgcgtgaag | 360 |
| ctgaccccc tgtgcgtgac cctgaagtgc cgcaacgtga acgccaccaa caacatcaac | 420 |

```
agcatgatcg acaacagcaa caagggcgag atgaagaact gcagcttcaa cgtgaccacc      480
gagctgcgcg accgcaagca ggaggtgcac gccctgttct accgcctgga cgtggtgccc      540
ctgcagggca acaacagcaa cgagtaccgc ctgatcaact gcaacaccag cgccatcacc      600
caggcctgcc ccaaggtgag cttcgacccc atccccatcc actactgcac cccgccggc       660 tacgccatcc tgaagtgcaa caaccagacc ttcaacggca ccggcccctg caacaacgtg      720
agcagcgtgc agtgcgccca cggcatcaag cccgtggtga gcacccagct gctgctgaac      780
ggcagcctgg ccaagggcga gatcatcatc cgcagcgaga acctggccaa caacgccaag      840
atcatcatcg tgcagctgaa caagcccgtg aagatcgtgt gcgtgcgccc caacaacaac      900
acccgcaaga gcgtgcgcat cggccccggc cagaccttct acgccaccgg cgagatcatc      960
ggcgacatcc gccaggccta ctgcatcatc aacaagaccg agtggaacag cacccctgcag     1020 ggcgtgagca gaagctgga ggagcacttc agcaagaagg ccatcaagtt cgagcccagc       1080
agcggcggcg acctggagat caccacccac agcttcaact gccgcggcga gttcttctac      1140
tgcgacacca gccagctgtt caacagcacc tacagcccca gcttcaacgg caccgagaac      1200
aagctgaacg gcaccatcac catcacctgc cgcatcaagc agatcatcaa catgtggcag      1260
aaggtgggcc gcgccatgta cgcccccccc atcgccggca acctgacctg cgagagcaac      1320
atcaccggcc tgctgctgac ccgcgacggc ggcaagaccg gccccaacga caccgagatc      1380
ttccgccccg gcggcggcga catgcgcgac aactggcgca acgagctgta caagtacaag      1440
gtggtggaga tcaagcccct gggcgtggcc cccaccgagg ccaagcgccg cgtggtggag      1500
cgcgagaagc gcgccgtggg catcggcgcc gtgttcctgg gcttcctggg cgccgccggc      1560
agcaccatgg gcgccgccag catcacactg accgtgcagg cccgcctgct gctgagcggc      1620
atcgtgcagc agcagaacaa cctgctgcgc gccatcgagg cccagcagca cctgctgcag      1680
ctgaccgtgt ggggcatcaa gcagctgcag acccgcatcc tggccgtgga gcgctacctg      1740
aaggaccagc agctgctggg catctggggc tgcagcggca gctgatctg caccaccgcc       1800 gtgccctgga acagcagctg gagcaaccgc agccacgacg agatctggga caacatgacc      1860
tggatgcagt gggaccgcga gatcaacaac tacaccgaca ccatctaccg cctgctggag      1920
gagagccaga accagcagga agaacgag aaggacctgc tggccctgga cagctggcag        1980
aacctgtgga actggttcag catcaccaac tggctgtggt acatcaagat cttcatcatg      2040
atcgtgggcg gcctgatcgg cctgcgcatc atcttcgccg tgctgagcat cgtgaaccgc      2100
gtgcgccagg gctacagccc cctgcccttc cagaccctga cccccaaccc ccgcgagccc      2160
gaccgcctgg gccgcatcga ggaggagggc ggcgagcagg accgcggccg cagcatccgc      2220
ctggtgagcg gcttcctggc cctggcctgg gacgacctgc gcagcctgtg cctgttcagc      2280
taccaccgcc tgcgcgactt catcctgatc gccgcccgcg tgctggagct gctgggccag      2340
cgcggctggg aggccctgaa gtacctgggc agcctggtgc agtactgggg cctggagctg      2400
aagaagagcg ccatcagcct gctggacacc atcgccatcg ccgtggccga gggcaccgac      2460
cgcatcatcg agttcatcca gcgcatctgc cgcgccatcc gcaacatccc ccgccgcatc      2520
cgccagggct tcgaggccgc cctgcag                                          2547
```

<210> SEQ ID NO 10
<211> LENGTH: 1035
<212> TYPE: DNA
<213> ORGANISM: Artificial Sequence
<220> FEATURE:
<223> OTHER INFORMATION: Description of Artificial Sequence: synthetic -continued a gp41 coding region of HIV strain AF110968

<400> SEQUENCE: 10

```
gccgtgggca tcggcgccgt gttcctgggc ttcctgggcg ccgccggcag caccatgggc     60
gccgccagca tcaccctgac cgtgcaggcc cgcctgctgc tgagcggcat cgtgcagcag    120
cagaacaacc tgctgcgcgc catcgaggcc cagcagcacc tgctgcagct gaccgtgtgg    180
ggcatcaagc agctgcagac ccgcatcctg gccgtggagc gctacctgaa ggaccagcag    240
ctgctgggca tctggggctg cagcggcaag ctgatctgca ccaccgccgt gccctggaac    300
agcagctgga gcaaccgcag ccacgacgag atctgggaca acatgacctg gatgcagtgg    360
gaccgcgaga tcaacaacta caccgacacc atctaccgcc tgctggagga gagccagaac    420
cagcaggaga agaacgagaa ggacctgctg gccctggaca gctggcagaa cctgtggaac    480
tggttcagca tcaccaactg gctgtggtac atcaagatct tcatcatgat cgtgggcggc    540
ctgatcggcc tgcgcatcat cttcgccgtg ctgagcatcg tgaaccgcgt gcgccagggc    600
tacagccccc tgcccttcca gaccctgacc cccaaccccc gcgagcccga ccgcctgggc    660
cgcatcgagg aggagggcgg cgagcaggac cgcggccgca gcatccgcct ggtgagcggc    720
ttcctggccc tggcctggga cgacctgcgc agcctgtgcc tgttcagcta ccaccgcctg    780
cgcgacttca tcctgatcgc cgcccgcgtg ctggagctgc tgggccagcg cggctgggag    840
gccctgaagt acctgggcag cctggtgcag tactggggcc tggagctgaa gaagagcgcc    900
atcagcctgc tggacaccat cgccatcgcc gtggccgagg gcaccgaccg catcatcgag    960
ttcatccagc gcatctgccg cgccatccgc aacatccccc gccgcatccg ccagggcttc   1020
gaggccgccc tgcag                                                    1035
```

<210> SEQ ID NO 11
<211> LENGTH: 144
<212> TYPE: DNA
<213> ORGANISM: Artificial Sequence
<220> FEATURE:
<223> OTHER INFORMATION: Description of Artificial Sequence: synthetic
Env common region of HIV strain AF110975

<400> SEQUENCE: 11

```
agcatcatca ccctgccctg ccgcatcaag cagatcatcg acatgtggca gaaggtgggc     60
cgcgccatct acgccccccc catcgagggc aacatcacct gcagcagcag catcaccggc    120
ctgctgctgg cccgcgacgg cggc                                           144
```

<210> SEQ ID NO 12
<211> LENGTH: 1437
<212> TYPE: DNA
<213> ORGANISM: Artificial Sequence
<220> FEATURE:
<223> OTHER INFORMATION: Description of Artificial Sequence: synthetic
gp120 coding region of HIV strain AF110975

<400> SEQUENCE: 12

```
agcggcctgg gcaacctgtg ggtgaccgtg tacgacggcg tgcccgtgtg gcgcgaggcc     60
agcaccaccc tgttctgcgc cagcgacgcc aaggcctacg agaaggaggt gcacaacgtg    120
tgggccaccc acgcctgcgt gcccaccgac cccaaccccc aggagatcga gctggacaac    180
gtgaccgaga acttcaacat gtggaagaac gacatggtgg accagatgca cgaggacatc    240
atcagcctgt gggaccagag cctgaagccc cgcgtgaagc tgacccccct gtgcgtgacc    300
ctgaagtgca ccaactacag caccaactac agcaacacca tgaacgccac cagctacaac    360
```

```
aacaacacca ccgaggagat caagaactgc accttcaaca tgaccaccga gctgcgcgac    420
aagaagcagc aggtgtacgc cctgttctac aagctggaca tcgtgcccct gaacagcaac    480
agcagcgagt accgcctgat caactgcaac accagcgcca tcacccaggc ctgccccaag    540
gtgagcttcg accccatccc catccactac tgcgcccccg ccggctacgc catcctgaag    600
tgcaagaaca acaccagcaa cggcaccggc ccctgccaga cgtgagcac cgtgcagtgc    660 acccacggca tcaagcccgt ggtgagcacc cccctgctgc tgaacggcag cctggccgag    720
ggcggcgaga tcatcatccg cagcaagaac ctgagcaaca cgcctacac catcatcgtg    780 cacctgaacg acagcgtgga gatcgtgtgc ccgcccca acaacaacac ccgcaagggc    840
atccgcatcg gccccggcca gaccttctac gccaccgaga acatcatcgg cgacatccgc    900
caggcccact gcaacatcag cgccggcgag tggaacaagg ccgtgcagcg cgtgagcgcc    960
aagctgcgcg agcacttccc caacaagacc atcgagttcc agcccagcag cggcggcgac   1020
ctggagatca ccacccacag cttcaactgc cgcggcgagt tcttctactg caacaccagc   1080
aagctgttca acagcagcta acggcacc agctaccgcg caccgagag caacagcagc   1140 atcatcaccc tgccctgccg catcaagcag atcatcgaca tgtggcagaa ggtgggccgc   1200
gccatctacg cccccccat cgagggcaac atcacctgca gcagcagcat caccggcctg   1260
ctgctggccc cgacggcgg cctggacaac atcaccaccg agatcttccg cccccaggg    1320 ggcgacatga aggacaactg cgcaacgag ctgtacaagt acaaggtggt ggagatcaag   1380 ccctgggcg tggccccac cgaggccaag cgccgcgtgg tggagcgcga aagcgc       1437
```

<210> SEQ ID NO 13
<211> LENGTH: 1950
<212> TYPE: DNA
<213> ORGANISM: Artificial Sequence
<220> FEATURE:
<223> OTHER INFORMATION: Description of Artificial Sequence: synthetic
gp140 coding region of HIV strain AF110975

<400> SEQUENCE: 13

```
agcggcctgg gcaacctgtg ggtgaccgtg tacgacggcg tgcccgtgtg gcgcgaggcc     60
agcaccaccc tgttctgcgc cagcgacgcc aaggcctacg agaaggaggt gcacaacgtg    120
tgggccaccc acgcctgcgt gcccaccgac cccaaccccc aggagatcga gctggacaac    180
gtgaccgaga acttcaacat gtggaagaac gacatggtgg accagatgca cgaggacatc    240
atcagcctgt gggaccagag cctgaagccc gcgtgaagc tgaccccct gtgcgtgacc    300 ctgaagtgca ccaactacag caccaactac agcaacacca tgaacgccac cagctacaac    360
aacaacacca ccgaggagat caagaactgc accttcaaca tgaccaccga gctgcgcgac    420
aagaagcagc aggtgtacgc cctgttctac aagctggaca tcgtgcccct gaacagcaac    480
agcagcgagt accgcctgat caactgcaac accagcgcca tcacccaggc ctgccccaag    540
gtgagcttcg accccatccc catccactac tgcgcccccg ccggctacgc catcctgaag    600
tgcaagaaca acaccagcaa cggcaccggc ccctgccaga cgtgagcac cgtgcagtgc    660 acccacggca tcaagcccgt ggtgagcacc cccctgctgc tgaacggcag cctggccgag    720
ggcggcgaga tcatcatccg cagcaagaac ctgagcaaca cgcctacac catcatcgtg    780 cacctgaacg acagcgtgga gatcgtgtgc ccgcccca acaacaacac ccgcaagggc    840
atccgcatcg gccccggcca gaccttctac gccaccgaga acatcatcgg cgacatccgc    900
caggcccact gcaacatcag cgccggcgag tggaacaagg ccgtgcagcg cgtgagcgcc    960
aagctgcgcg agcacttccc caacaagacc atcgagttcc agcccagcag cggcggcgac   1020
```

```
ctggagatca ccacccacag cttcaactgc cgcggcgagt tcttctactg caacaccagc    1080
aagctgttca acagcagcta acggcacc agctaccgcg gcaccgagag caacagcagc      1140
atcatcaccc tgccctgccg catcaagcag atcatcgaca tgtggcagaa ggtgggccgc    1200
gccatctacg cccccccat cgagggcaac atcacctgca gcagcat caccggcctg        1260 ctgctggccc gcgacggcgg cctggacaac atcaccaccg agatcttccg ccccagggc    1320 ggcgacatga aggacaactg cgcaacgag ctgtacaagt acaaggtggt ggagatcaag     1380
cccctgggcg tggcccccac cgaggccaag cgccgcgtgg tggagcgcga aagcgcgcc    1440 gtgggcatcg gcgccgtgat cttcggcttc ctgggcgccg ccggcagcaa catgggcgcc   1500
gccagcatca ccctgaccgc ccaggcccgc cagctgctga gcggcatcgt gcagcagcag   1560
agcaacctgc tgcgcgccat cgaggcccag cagcacatgc tgcagctgac cgtgtggggc   1620
atcaagcagc tgcaggcccg cgtgctggcc atcgagcgct acctgaagga ccagcagctg   1680
ctgggcatct ggggctgcag cggcaagctg atctgcacca ccaccgtgcc ctggaacagc   1740
agctggagca acaagaccca gggcgagatc tgggagaaca tgacctggat gcagtgggac   1800
aaggagatca gcaactacac cggcatcatc taccgcctgc tggaggagag ccagaaccag   1860
caggagcaga acgagaagga cctgctggcc ctggacagcc gcaacaacct gtggagctgg   1920
ttcaacatca gcaactggct gtggtacatc                                    1950

<210> SEQ ID NO 14
<211> LENGTH: 2493
<212> TYPE: DNA
<213> ORGANISM: Artificial Sequence
<220> FEATURE:
<223> OTHER INFORMATION: Description of Artificial Sequence: synthetic
      gp160 coding region of HIV strain AF110975

<400> SEQUENCE: 14
agcggcctgg gcaacctgtg ggtgaccgtg tacgacggcg tgcccgtgtg cgcgcgaggcc      60 agcaccaccc tgttctgcgc cagcgacgcc aaggcctacg agaaggaggt gcacaacgtg    120
tgggccaccc acgcctgcgt gcccaccgac cccaaccccc aggagatcga gctgacaac    180 gtgaccgaga acttcaacat gtggaagaac gacatggtgg accagatgca cgaggacatc    240
atcagcctgt gggaccagag cctgaagccc cgcgtgaagc tgaccccccct gtgcgtgacc    300 ctgaagtgca ccaactacag caccaactac agcaacacca tgaacgccac cagctacaac    360
aacaacacca ccgaggagat caagaactgc accttcaaca tgaccaccga gctgcgcgac    420
aagaagcagc aggtgtacgc cctgttctac aagctggaca tcgtgccccct gaacagcaac    480 agcagcgagt accgcctgat caactgcaac accagcgcca tcacccaggc tgccccaag    540 gtgagcttcg accccatccc catccactac tgcgcccccg ccggctacgc catcctgaag   600
tgcaagaaca caccagcaa cggcaccggc ccctgccaga cgtgagcac cgtgcagtgc    660 acccacggca tcaagcccgt ggtgagcacc cccctgctgc tgaacggcag cctggccgag    720
ggcggcgaga tcatcatccg cagcaagaac ctgagcaaca cgcctacac catcatcgtg    780 cacctgaacg acagcgtgga gatcgtgtgc acccgcccca caacaacac ccgcaagggc    840 atccgcatcg gccccggcca gaccttctac gccaccgaga acatcatcgg cgacatccgc    900
caggcccact gcaacatcag cgccggcgag tggaacaagg ccgtgcagcg cgtgagcgcc    960
aagctgcgcg agcactttcc caacaagacc atcgagttcc agcccagcag cggcggcgac    1020
ctggagatca ccacccacag cttcaactgc cgcggcgagt tcttctactg caacaccagc    1080
```

-continued

| | |
|---|---|
| aagctgttca acagcagcta caacggcacc agctaccgcg gcaccgagag caacagcagc | 1140 |
| atcatcaccc tgccctgccg catcaagcag atcatcgaca tgtggcagaa ggtgggccgc | 1200 |
| gccatctacg cccccccat cgagggcaac atcacctgca gcagcagcat caccggcctg | 1260 |
| ctgctggccc gcgacggcgg cctggacaac atcaccaccg agatcttccg cccccagggc | 1320 |
| ggcgacatga aggacaactg gcgcaacgag ctgtacaagt acaaggtggt ggagatcaag | 1380 |
| cccctggggc tggcccccac cgaggccaag cgccgcgtgg tggagcgcga aagcgcgcc | 1440 |
| gtgggcatcg cgccgtgat cttcggcttc ctgggcgccg ccggcagcaa catgggcgcc | 1500 |
| gccagcatca ccctgaccgc ccaggcccgc cagctgctga gcggcatcgt gcagcagcag | 1560 |
| agcaacctgc tgcgcgccat cgaggcccag cagcacatgc tgcagctgac cgtgtgggc | 1620 |
| atcaagcagc tgcaggcccg cgtgctggcc atcgagcgct acctgaagga ccagcagctg | 1680 |
| ctgggcatct ggggctgcag cggcaagctg atctgcacca ccaccgtgcc ctggaacagc | 1740 |
| agctggagca acaagaccca gggcgagatc tgggagaaca tgacctggat gcagtgggac | 1800 |
| aaggagatca gcaactacac cggcatcatc taccgcctgc tggaggagag ccagaaccag | 1860 |
| caggagcaga acgagaagga cctgctggcc ctggacagcc gcaacaacct gtggagctgg | 1920 |
| ttcaacatca gcaactggct gtggtacatc aagatcttca tcatgatcgt gggcggcctg | 1980 |
| atcggcctgc gcatcatctt cgccgtgctg agcatcgtga accgcgtgcg ccagggctac | 2040 |
| agccccctga gcttccagac cctgacccc aaccccgcg gcctggaccg cctgggccgc | 2100 |
| atcgaggagg agggcggcga gcaggaccgc gaccgcagca tccgcctggt gcagggcttc | 2160 |
| ctggccctgg cctgggacga cctgcgcagc ctgtgcctgt tcagctacca ccgcctgcgc | 2220 |
| gacctgatcc tggtgaccgc ccgcgtggtg gagctgctgg gccgcagcag ccccgcggc | 2280 |
| ctgcagcgcg gctgggaggc cctgaagtac ctgggcagcc tggtgcagta ctggggcctg | 2340 |
| gagctgaaga gagcgccac cagcctgctg acagcatcg ccatcgccgt ggccgagggc | 2400 |
| accgaccgca tcatcgaggt gatccagcgc atctaccgcg ccttctgcaa catcccccgc | 2460 |
| cgcgtgcgcc agggcttcga ggccgccctg cag | 2493 |

<210> SEQ ID NO 15
<211> LENGTH: 2565
<212> TYPE: DNA
<213> ORGANISM: Artificial Sequence
<220> FEATURE:
<223> OTHER INFORMATION: Description of Artificial Sequence: synthetic signal sequence and gp160 coding region of HIV strain AF110975

<400> SEQUENCE: 15

| | |
|---|---|
| atgcgcgtgc gcggcatcct gcgcagctgg cagcagtggt ggatctgggg catcctgggc | 60 |
| ttctggatct gcagcggcct gggcaacctg tgggtgaccg tgtacgacgg cgtgcccgtg | 120 |
| tggcgcgagg ccagcaccac cctgttctgc gccagcgacg ccaaggccta cgagaaggag | 180 |
| gtgcacaacg tgtgggccac ccacgcctgc gtgcccaccg accccaaccc caggagatc | 240 |
| gagctggaca acgtgaccga aacttcaac atgtggaaga cgacatggt ggaccagatg | 300 |
| cacgaggaca tcatcagcct gtgggaccag agcctgaagc ccgcgtgaa gctgaccccc | 360 |
| ctgtgcgtga ccctgaagtg caccaactac agcaccaact acagcaacac catgaacgcc | 420 |
| accagctaca caacaacac caccgaggag atcaagaact gcaccttcaa catgaccacc | 480 |
| gagctgcgcg acaagaagca gcaggtgtac gccctgttct acaagctgga catcgtgccc | 540 |
| ctgaacagca acagcagcga gtaccgcctg atcaactgca acaccagcgc catcacccag | 600 |

```
gcctgcccca aggtgagctt cgaccccatc cccatccact actgcgcccc cgccggctac    660
gccatcctga agtgcaagaa caacaccagc aacggcaccg ccccctgcca gaacgtgagc    720
accgtgcagt gcacccacgg catcaagccc gtggtgagca ccccctgct gctgaacggc     780 agcctggccg agggcggcga gatcatcatc cgcagcaaga acctgagcaa caacgcctac    840
accatcatcg tgcacctgaa cgacagcgtg gagatcgtgt gcacccgccc caacaacaac    900 accccgcaagg gcatccgcat cggccccggc cagaccttct acgccaccga gaacatcatc    960
ggcgacatcc gccaggccca ctgcaacatc agcgccggcg agtggaacaa ggccgtgcag   1020
cgcgtgagcg ccaagctgcg cgagcacttc cccaacaaga ccatcgagtt ccagcccagc   1080
agcggcggcg acctggagat caccacccac agcttcaact gccgcggcga gttcttctac   1140
tgcaacacca gcaagctgtt caacagcagc tacaacggca ccagctaccg cggcaccgag   1200
agcaacagca gcatcatcac cctgccctgc cgcatcaagc agatcatcga catgtggcag   1260 aaggtggggcc gcgccatcta cgccccccccc atcgagggca acatcacctg cagcagcagc   1320
atcaccggcc tgctgctggc ccgcgacggc ggcctggaca catcaccac cgagatcttc   1380 cgcccccagg gcggcgacat gaaggacaac tggcgcaacg agctgtacaa gtacaaggtg   1440
gtggagatca agcccctggg cgtggccccc accgaggcca agccgcgt ggtggagcgc   1500 gagaagcgcg ccgtgggcat cggcgccgtg atcttcggct tcctgggcgc cgccggcagc   1560
aacatgggcg ccgccagcat caccctgacc gcccaggccc gccagctgct gagcggcatc   1620
gtgcagcagc agagcaacct gctgcgcgcc atcgaggccc agcagcacat gctgcagctg   1680
accgtgtggg gcatcaagca gctgcaggcc cgcgtgctgg ccatcgagcg ctacctgaag   1740
gaccagcagc tgctgggcat ctggggctgc agcggcaagc tgatctgcac caccaccgtg   1800
ccctggaaca gcagctggag caacaagacc cagggcgaga tctgggagaa catgacctgg   1860
atgcagtggg acaaggagat cagcaactac accggcatca tctaccgcct gctggaggag   1920
agccagaacc agcaggagca gaacgagaag gacctgctgg ccctggacag ccgcaacaac   1980
ctgtggagct ggttcaacat cagcaactgg ctgtggtaca tcaagatctt catcatgatc   2040
gtgggcggcc tgatcggcct gcgcatcatc ttcgccgtgc tgagcatcgt gaaccgcgtg   2100
cgccagggct acagccccct gagcttccag accctgaccc ccaaccccg cggcctggac   2160 cgcctgggcc gcatcgagga ggagggcggc gagcaggacc gcgaccgcag catccgcctg   2220
gtgcagggct tcctggcccct ggcctgggac gacctgcgca gcctgtgcct gttcagctac   2280
caccgcctgc gcgacctgat cctggtgacc gcccgcgtgg tggagctgct gggccgcagc   2340 agccccgcg gcctgcagcg cggctgggag gccctgaagt acctgggcag cctggtgcag   2400
tactggggcc tggagctgaa gaagagcgcc accagcctgc tggacagcat cgccatcgcc   2460
gtggccgagg gcaccgaccg catcatcgag gtgatccagc gcatctaccg cgccttctgc   2520
aacatccccc gccgcgtgcg ccagggcttc gaggccgccc tgcag                   2565
```

<210> SEQ ID NO 16
<211> LENGTH: 1056
<212> TYPE: DNA
<213> ORGANISM: Artificial Sequence
<220> FEATURE:
<223> OTHER INFORMATION: Description of Artificial Sequence: synthetic a gp41 coding region of HIV strain AF110975

<400> SEQUENCE: 16

```
gccgtgggca tcggcgccgt gatcttcggc ttcctgggcg ccgccggcag caacatgggc     60
gccgccagca tcaccctgac cgcccaggcc cgccagctgc tgagcggcat cgtgcagcag    120
```

```
cagagcaacc tgctgcgcgc catcgaggcc cagcagcaca tgctgcagct gaccgtgtgg      180
ggcatcaagc agctgcaggc ccgcgtgctg gccatcgagc gctacctgaa ggaccagcag      240
ctgctgggca tctggggctg cagcggcaag ctgatctgca ccaccaccgt gccctggaac      300
agcagctgga gcaacaagac ccagggcgag atctgggaga acatgacctg gatgcagtgg      360
gacaaggaga tcagcaacta caccggcatc atctaccgcc tgctggagga gagccagaac      420
cagcaggagc agaacgagaa ggacctgctg gccctggaca gccgcaacaa cctgtggagc      480
tggttcaaca tcagcaactg gctgtggtac atcaagatct tcatcatgat cgtgggcggc      540
ctgatcggcc tgcgcatcat cttcgccgtg ctgagcatcg tgaaccgcgt gcgccagggc      600
tacagccccc tgagcttcca gaccctgacc cccaaccccc gcggcctgga ccgcctgggc      660
cgcatcgagg aggagggcgg cgagcaggac cgcgaccgca gcatccgcct ggtgcagggc      720
ttcctggccc tggcctggga cgacctgcgc agcctgtgcc tgttcagcta ccaccgcctg      780
cgcgacctga tcctggtgac cgcccgcgtg gtggagctgc tgggccgcag cagcccccgc      840
ggcctgcagc gcggctggga ggccctgaag tacctgggca gcctggtgca gtactggggc      900
ctggagctga agaagagcgc caccagcctg ctggacagca tcgccatcgc cgtggccgag      960
ggcaccgacc gcatcatcga ggtgatccag cgcatctacc gcgccttctg caacatcccc     1020
cgccgcgtgc gccagggctt cgaggccgcc ctgcag                                1056

<210> SEQ ID NO 17
<211> LENGTH: 492
<212> TYPE: PRT
<213> ORGANISM: Human immunodeficiency virus

<400> SEQUENCE: 17

Met Gly Ala Arg Ala Ser Ile Leu Arg Gly Gly Lys Leu Asp Ala Trp
  1               5                  10                  15

Glu Arg Ile Arg Leu Arg Pro Gly Gly Lys Lys Cys Tyr Met Met Lys
             20                  25                  30

His Leu Val Trp Ala Ser Arg Glu Leu Glu Lys Phe Ala Leu Asn Pro
         35                  40                  45

Gly Leu Leu Glu Thr Ser Glu Gly Cys Lys Gln Ile Ile Arg Gln Leu
     50                  55                  60

His Pro Ala Leu Gln Thr Gly Ser Glu Glu Leu Lys Ser Leu Phe Asn
 65                  70                  75                  80

Thr Val Ala Thr Leu Tyr Cys Val His Glu Lys Ile Glu Val Arg Asp
                 85                  90                  95

Thr Lys Glu Ala Leu Asp Lys Ile Glu Glu Glu Gln Asn Lys Cys Gln
            100                 105                 110

Gln Lys Ile Gln Gln Ala Glu Ala Ala Asp Lys Gly Lys Val Ser Gln
        115                 120                 125

Asn Tyr Pro Ile Val Gln Asn Leu Gln Gly Gln Met Val His Gln Ala
    130                 135                 140

Ile Ser Pro Arg Thr Leu Asn Ala Trp Val Lys Val Ile Glu Glu Lys
145                 150                 155                 160

Ala Phe Ser Pro Glu Val Ile Pro Met Phe Thr Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Asp Thr Ile Asn Glu Glu Ala Ala
        195                 200                 205
```

```
Glu Trp Asp Arg Val His Pro Val His Ala Gly Pro Ile Ala Pro Gly
    210                 215                 220
Gln Met Arg Glu Pro Arg Gly Ser Asp Ile Ala Gly Thr Thr Ser Thr
225                 230                 235                 240
Leu Gln Glu Gln Ile Ala Trp Met Thr Ser Asn Pro Pro Ile Pro Val
                245                 250                 255
Gly Asp Ile Tyr Lys Arg Trp Ile Ile Leu Gly Leu Asn Lys Ile Val
                260                 265                 270
Arg Met Tyr Ser Pro Val Ser Ile Leu Asp Ile Lys Gln Gly Pro Lys
            275                 280                 285
Glu Pro Phe Arg Asp Tyr Val Asp Arg Phe Phe Lys Thr Leu Arg Ala
    290                 295                 300
Glu Gln Ser Thr Gln Glu Val Lys Asn Trp Met Thr Asp Thr Leu Leu
305                 310                 315                 320
Val Gln Asn Ala Asn Pro Asp Cys Lys Thr Ile Leu Arg Ala Leu Gly
                325                 330                 335
Pro Gly Ala Ser Leu Glu Glu Met Met Thr Ala Cys Gln Gly Val Gly
                340                 345                 350
Gly Pro Ser His Lys Ala Arg Val Leu Ala Glu Ala Met Ser Gln Ala
            355                 360                 365
Asn Thr Ser Val Met Met Gln Lys Ser Asn Phe Lys Gly Pro Arg Arg
    370                 375                 380
Ile Val Lys Cys Phe Asn Cys Gly Lys Glu Gly His Ile Ala Arg Asn
385                 390                 395                 400
Cys Arg Ala Pro Arg Lys Lys Gly Cys Trp Lys Cys Gly Lys Glu Gly
                405                 410                 415
His Gln Met Lys Asp Cys Thr Glu Arg Gln Ala Asn Phe Leu Gly Lys
                420                 425                 430
Ile Trp Pro Ser His Lys Gly Arg Pro Gly Asn Phe Leu Gln Ser Arg
            435                 440                 445
Pro Glu Pro Thr Ala Pro Pro Ala Glu Ser Phe Arg Phe Glu Glu Thr
    450                 455                 460
Thr Pro Gly Gln Lys Gln Glu Ser Lys Asp Arg Glu Thr Leu Thr Ser
465                 470                 475                 480
Leu Lys Ser Leu Phe Gly Asn Asp Pro Leu Ser Gln
                485                 490

<210> SEQ ID NO 18
<211> LENGTH: 81
<212> TYPE: DNA
<213> ORGANISM: Artificial Sequence
<220> FEATURE:
<223> OTHER INFORMATION: Description of Artificial Sequence: synthetic
      signal sequence of HIV strain AF110968

<400> SEQUENCE: 18
atgcgcgtga tgggcatcct gaagaactac cagcagtggt ggatgtgggg catcctgggc    60
ttctggatgc tgatcatcag c                                              81

<210> SEQ ID NO 19
<211> LENGTH: 72
<212> TYPE: DNA
<213> ORGANISM: Artificial Sequence
<220> FEATURE:
<223> OTHER INFORMATION: Description of Artificial Sequence: synthetic
      signal sequence of HIV strain AF110975

<400> SEQUENCE: 19
```

```
atgcgcgtgc gcggcatcct gcgcagctgg cagcagtggt ggatctgggg catcctgggc    60
ttctggatct gc                                                        72
```

<210> SEQ ID NO 20
<211> LENGTH: 1479
<212> TYPE: DNA
<213> ORGANISM: Artificial Sequence
<220> FEATURE:
<223> OTHER INFORMATION: Description of Artificial Sequence: synthetic
       Gag coding sequence of HIV strain AF110965

<400> SEQUENCE: 20

```
atgggcgccc gcgccagcat cctgcgcggc ggcaagctgg acgcctggga gcgcatccgc    60
ctgcgccccg gcggcaagaa gtgctacatg atgaagcacc tggtgtgggc cagccgcgag   120
ctggagaagt tcgccctgaa ccccggcctg ctggagacca gcgagggctg caagcagatc   180
atccgccagc tgcaccccgc cctgcagacc ggcagcgagg agctgaagag cctgttcaac   240
accgtggcca ccctgtactg cgtgcacgag aagatcgagg tgcgcgacac caaggaggcc   300
ctggacaaga tcgaggagga gcagaacaag tgccagcaga gatccagca ggccgaggcc   360 gccgacaagg gcaaggtgag ccagaactac cccatcgtgc agaacctgca gggccagatg   420
gtgcaccagg ccatcagccc ccgcaccctg aacgcctggg tgaaggtgat cgaggagaag   480
gccttcagcc ccgaggtgat ccccatgttc accgccctga gcgagggcgc caccccccag   540
gacctgaaca ccatgctgaa caccgtgggc ggccaccagg ccgccatgca gatgctgaag   600
gacaccatca cgaggaggc cgccgagtgg gaccgcgtgc accccgtgca cgccggcccc   660
atcgcccccg ccagatgcg cgagccccgc ggcagcgaca tcgccggcac caccagcacc   720
ctgcaggagc agatcgcctg gatgaccagc aaccccccca tccccgtggg cgacatctac   780
aagcgctgga tcatcctggg cctgaacaag atcgtgcgca tgtacagccc cgtgagcatc   840
ctggacatca gcagggccc caaggagccc ttccgcgact acgtggaccg cttcttcaag   900
accctgcgcg ccgagcagag caccaggag gtgaagaact ggatgaccga caccctgctg   960
gtgcagaacg ccaaccccga ctgcaagacc atcctgcgcg ccctgggccc cggcgccagc  1020
ctggaggaga tgatgaccgc ctgccagggc gtgggcggcc cagccacaa ggcccgcgtg  1080 ctggccgagg ccatgagcca ggccaacacc agcgtgatga tgcagaagag caacttcaag  1140 ggccccccgcc gcatcgtgaa gtgcttcaac tgcggcaagg agggccacat cgcccgcaac  1200
tgccgcgccc ccgcaagaa gggctgctgg aagtgcggca aggagggcca ccagatgaag  1260
gactgcaccg agcgccaggc caacttcctg ggcaagatct ggcccagcca aagggccgc  1320 cccggcaact tcctgcagag ccgccccgag cccaccgccc ccccgccga gcttccgc  1380 ttcgaggaga ccaccccggg ccagaagcag gagagcaagg accgcgagac cctgaccagc  1440
ctgaagagcc tgttcggcaa cgacccctg agccagtaa                          1479
```

<210> SEQ ID NO 21
<211> LENGTH: 1509
<212> TYPE: DNA
<213> ORGANISM: Artificial Sequence
<220> FEATURE:
<223> OTHER INFORMATION: Description of Artificial Sequence: synthetic
       Gag coding sequence of HIV strain AF110967

<400> SEQUENCE: 21

```
atgggcgccc gcgccagcat cctgcgcggc gagaagctgg acaagtggga gaagatccgc    60
ctgcgccccg gcggcaagaa gcactacatg ctgaagcacc tggtgtgggc cagccgcgag   120
```

```
ctggagggct cgccctgaa ccccggcctg ctggagaccg ccgagggctg caagcagatc      180
atgaagcagc tgcagcccgc cctgcagacc ggcaccgagg agctgcgcag cctgtacaac      240
accgtggcca ccctgtactg cgtgcacgcc ggcatcgagg tgcgcgacac caaggaggcc      300
ctggacaaga tcgaggagga gcagaacaag agccagcaga gacccagca ggccaaggag       360 gccgacggca aggtgagcca gaactacccc atcgtgcaga acctgcaggg ccagatggtg      420
caccaggcca tcagccccg caccctgaac gcctgggtga aggtgatcga ggagaaggcc       480
ttcagccccg aggtgatccc catgttcacc gccctgagcg agggcgccac ccccaggac       540 ctgaacacca tgctgaacac cgtgggcggc caccaggccg ccatgcagat gctgaaggac      600
accatcaacg aggaggccgc cgagtgggac cgcctgcacc ccgtgcaggc cggccccgtg      660
gcccccggcc agatgcgcga cccccgcggc agcgacatcg ccggcgccac cagcaccctg      720
caggagcaga tcgcctggat gaccagcaac ccccccgtgc ccgtgggcga catctacaag      780
cgctggatca tcctgggcct gaacaagatc gtgcgcatgt acagccccgt gagcatcctg      840
gacatccgcc agggccccaa ggagcccttc cgcgactacg tggaccgctt cttcaagacc      900
ctgcgcgccg agcaggccac ccaggacgtg aagaactgga tgaccgagac cctgctggtg      960
cagaacgcca accccgactg caagaccatc ctgcgcgccc tgggccccgg cgccacccctg    1020 gaggagatga tgaccgcctg ccagggcgtg ggcggccccg ccacaaggc ccgcgtgctg       1080 gccgaggcca tgagccaggc caacagcgtg aacatcatga tgcagaagag caacttcaag      1140 ggccccgcc gcaacgtgaa gtgcttcaac tgcggcaagg agggccacat cgccaagaac      1200
tgccgcgccc cccgcaagaa gggctgctgg aagtgcggca aggagggcca ccagatgaag      1260
gactgcaccg agcgccaggc caacttcctg ggcaagatct ggcccagcca aagggccgc       1320 cccggcaact tcctgcagaa ccgcagcgag cccgccgccc ccaccgtgcc caccgccccc      1380
cccgccgaga gcttccgctt cgaggagacc acccccgccc ccaagcagga gcccaaggac      1440
cgcgagccct accgcgagcc cctgaccgcc ctgcgcagcc tgttcggcag cggccccctg      1500
agccagtaa                                                             1509
```

<210> SEQ ID NO 22
<211> LENGTH: 502
<212> TYPE: PRT
<213> ORGANISM: Human immunodeficiency virus

<400> SEQUENCE: 22

```
Met Gly Ala Arg Ala Ser Ile Leu Arg Gly Glu Lys Leu Asp Lys Trp
 1               5                  10                  15

Glu Lys Ile Arg Leu Arg Pro Gly Gly Lys Lys His Tyr Met Leu Lys
            20                  25                  30

His Leu Val Trp Ala Ser Arg Glu Leu Glu Gly Phe Ala Leu Asn Pro
        35                  40                  45

Gly Leu Leu Glu Thr Ala Glu Gly Cys Lys Gln Ile Met Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125
```

```
Tyr Pro Ile Val Gln Asn Leu Gln Gly Gln Met Val His Gln Ala Ile
            130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
            195                 200                 205

Trp Asp Arg Leu His Pro Val Gln Ala Gly Pro Val Ala Pro Gly Gln
210                 215                 220

Met Arg Asp Pro Arg Gly Ser Asp Ile Ala Gly Ala Thr Ser Thr Leu
225                 230                 235                 240

Gln Glu Gln Ile Ala Trp Met Thr Ser Asn Pro Pro Val Pro Val Gly
                245                 250                 255

Asp Ile Tyr Lys Arg Trp Ile Ile Leu Gly Leu Asn Lys Ile Val Arg
                260                 265                 270

Met Tyr Ser Pro Val Ser Ile Leu Asp Ile Arg Gln Gly Pro Lys Glu
            275                 280                 285

Pro Phe Arg Asp Tyr Val Asp Arg Phe Phe Lys Thr Leu Arg Ala Glu
            290                 295                 300

Gln Ala Thr Gln Asp Val Lys Asn Trp Met Thr Glu Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
            355                 360                 365

Ser Val Asn Ile Met Met Gln Lys Ser Asn Phe Lys Gly Pro Arg Arg
370                 375                 380

Asn Val Lys Cys Phe Asn Cys Gly Lys Glu Gly His Ile Ala Lys Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
            435                 440                 445

Ser Glu Pro Ala Ala Pro Thr Val Pro Thr Ala Pro Pro Ala Glu Ser
450                 455                 460

Phe Arg Phe Glu Glu Thr Thr Pro Ala Pro Lys Gln Glu Pro Lys Asp
465                 470                 475                 480

Arg Glu Pro Tyr Arg Glu Pro Leu Thr Ala Leu Arg Ser Leu Phe Gly
                485                 490                 495

Ser Gly Pro Leu Ser Gln
            500

<210> SEQ ID NO 23
<211> LENGTH: 849
<212> TYPE: PRT
<213> ORGANISM: Human immunodeficiency virus

<400> SEQUENCE: 23
```

-continued

```
Met Arg Val Met Gly Ile Leu Lys Asn Tyr Gln Gln Trp Trp Met Trp
 1               5                  10                  15

Gly Ile Leu Gly Phe Trp Met Leu Ile Ser Ser Val Val Gly Asn
             20                  25                  30

Leu Trp Val Thr Val Tyr Tyr Gly Val Pro Val Trp Lys Glu Ala Lys
             35                  40                  45

Thr Thr Leu Phe Cys Thr Ser Asp Ala Lys Ala Tyr Glu Thr Glu Val
 50                  55                  60

His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                 85                  90                  95

Asn Asp Met Val Asp Gln Met His Glu Asp Ile Ile Ser Leu Trp Asp
             100                 105                 110

Gln Ser Leu Lys Pro Cys Val Lys Leu Thr Pro Leu Cys Val Thr Leu
     115                 120                 125

Lys Cys Arg Asn Val Asn Ala Thr Asn Asn Ile Asn Ser Met Ile Asp
     130                 135                 140

Asn Ser Asn Lys Gly Glu Met Lys Asn Cys Ser Phe Asn Val Thr Thr
145                 150                 155                 160

Glu Leu Arg Asp Arg Lys Gln Glu Val His Ala Leu Phe Tyr Arg Leu
                 165                 170                 175

Asp Val Val Pro Leu Gln Gly Asn Asn Ser Asn Glu Tyr Arg Leu Ile
             180                 185                 190

Asn Cys Asn Thr Ser Ala Ile Thr Gln Ala Cys Pro Lys Val Ser Phe
     195                 200                 205

Asp Pro Ile Pro Ile His Tyr Cys Thr Pro Ala Gly Tyr Ala Ile Leu
 210                 215                 220

Lys Cys Asn Asn Gln Thr Phe Asn Gly Thr Gly Pro Cys Asn Asn Val
225                 230                 235                 240

Ser Ser Val Gln Cys Ala His Gly Ile Lys Pro Val Val Ser Thr Gln
                 245                 250                 255

Leu Leu Leu Asn Gly Ser Leu Ala Lys Gly Glu Ile Ile Ile Arg Ser
             260                 265                 270

Glu Asn Leu Ala Asn Asn Ala Lys Ile Ile Val Gln Leu Asn Lys
     275                 280                 285

Pro Val Lys Ile Val Cys Val Arg Pro Asn Asn Asn Thr Arg Lys Ser
 290                 295                 300

Val Arg Ile Gly Pro Gly Gln Thr Phe Tyr Ala Thr Gly Glu Ile Ile
305                 310                 315                 320

Gly Asp Ile Arg Gln Ala Tyr Cys Ile Ile Asn Lys Thr Glu Trp Asn
                 325                 330                 335

Ser Thr Leu Gln Gly Val Ser Lys Lys Leu Glu Glu His Phe Ser Lys
             340                 345                 350

Lys Ala Ile Lys Phe Glu Pro Ser Ser Gly Gly Asp Leu Glu Ile Thr
     355                 360                 365

Thr His Ser Phe Asn Cys Arg Gly Glu Phe Phe Tyr Cys Asp Thr Ser
 370                 375                 380

Gln Leu Phe Asn Ser Thr Tyr Ser Pro Ser Phe Asn Gly Thr Glu Asn
385                 390                 395                 400

Lys Leu Asn Gly Thr Ile Thr Ile Thr Cys Arg Ile Lys Gln Ile Ile
                 405                 410                 415

Asn Met Trp Gln Lys Val Gly Arg Ala Met Tyr Ala Pro Pro Ile Ala
             420                 425                 430
```

```
Gly Asn Leu Thr Cys Glu Ser Asn Ile Thr Gly Leu Leu Thr Arg
            435                 440                 445

Asp Gly Gly Lys Thr Gly Pro Asn Asp Thr Glu Ile Phe Arg Pro Gly
            450                 455                 460

Gly Gly Asp Met Arg Asp Asn Trp Arg Asn Glu Leu Tyr Lys Tyr Lys
465                 470                 475                 480

Val Val Glu Ile Lys Pro Leu Gly Val Ala Pro Thr Glu Ala Lys Arg
                485                 490                 495

Arg Val Val Glu Arg Glu Lys Arg Ala Val Gly Ile Gly Ala Val Phe
                500                 505                 510

Leu Gly Phe Leu Gly Ala Ala Gly Ser Thr Met Gly Ala Ala Ser Ile
            515                 520                 525

Thr Leu Thr Val Gln Ala Arg Leu Leu Leu Ser Gly Ile Val Gln Gln
            530                 535                 540

Gln Asn Asn Leu Leu Arg Ala Ile Glu Ala Gln Gln His Leu Leu Gln
545                 550                 555                 560

Leu Thr Val Trp Gly Ile Lys Gln Leu Gln Thr Arg Ile Leu Ala Val
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Ala Val Pro Trp Asn Ser Ser Trp Ser
            595                 600                 605

Asn Arg Ser His Asp Glu Ile Trp Asp Asn Met Thr Trp Met Gln Trp
            610                 615                 620

Asp Arg Glu Ile Asn Asn Tyr Thr Asp Thr Ile Tyr Arg Leu Leu Glu
625                 630                 635                 640

Glu Ser Gln Asn Gln Gln Glu Lys Asn Glu Lys Asp Leu Leu Ala Leu
                645                 650                 655

Asp Ser Trp Gln Asn Leu Trp Asn Trp Phe Ser Ile Thr Asn Trp Leu
            660                 665                 670

Trp Tyr Ile Lys Ile Phe Ile Met Ile Val Gly Gly Leu Ile Gly Leu
            675                 680                 685

Arg Ile Ile Phe Ala Val Leu Ser Ile Val Asn Arg Val Arg Gln Gly
            690                 695                 700

Tyr Ser Pro Leu Pro Phe Gln Thr Leu Thr Pro Asn Pro Arg Glu Pro
705                 710                 715                 720

Asp Arg Leu Gly Arg Ile Glu Glu Gly Gly Glu Gln Asp Arg Gly
                725                 730                 735

Arg Ser Ile Arg Leu Val Ser Gly Phe Leu Ala Leu Ala Trp Asp Asp
            740                 745                 750

Leu Arg Ser Leu Cys Leu Phe Ser Tyr His Arg Leu Arg Asp Phe Ile
            755                 760                 765

Leu Ile Ala Ala Arg Val Leu Glu Leu Leu Gly Gln Arg Gly Trp Glu
            770                 775                 780

Ala Leu Lys Tyr Leu Gly Ser Leu Val Gln Tyr Trp Gly Leu Glu Leu
785                 790                 795                 800

Lys Lys Ser Ala Ile Ser Leu Leu Asp Thr Ile Ala Ile Ala Val Ala
                805                 810                 815

Glu Gly Thr Asp Arg Ile Ile Glu Phe Ile Gln Arg Ile Cys Arg Ala
            820                 825                 830

Ile Arg Asn Ile Pro Arg Arg Ile Arg Gln Gly Phe Glu Ala Ala Leu
            835                 840                 845

Gln
```

<210> SEQ ID NO 24
<211> LENGTH: 855
<212> TYPE: PRT
<213> ORGANISM: Human immunodeficiency virus

<400> SEQUENCE: 24

```
Met Arg Val Arg Gly Ile Leu Arg Ser Trp Gln Gln Trp Trp Ile Trp
  1               5                  10                  15

Gly Ile Leu Gly Phe Trp Ile Cys Ser Gly Leu Gly Asn Leu Trp Val
             20                  25                  30

Thr Val Tyr Asp Gly Val Pro Val Trp Arg Glu Ala Ser Thr Thr Leu
         35                  40                  45

Phe Cys Ala Ser Asp Ala Lys Ala Tyr Glu Lys Glu Val His Asn Val
 50                  55                  60

Trp Ala Thr His Ala Cys Val Pro Thr Asp Pro Asn Pro Gln Glu Ile
 65                  70                  75                  80

Glu Leu Asp Asn Val Thr Glu Asn Phe Asn Met Trp Lys Asn Asp Met
                 85                  90                  95

Val Asp Gln Met His Glu Asp Ile Ile Ser Leu Trp Asp Gln Ser Leu
            100                 105                 110

Lys Pro Arg Val Lys Leu Thr Pro Leu Cys Val Thr Leu Lys Cys Thr
        115                 120                 125

Asn Tyr Ser Thr Asn Tyr Ser Asn Thr Met Asn Ala Thr Ser Tyr Asn
130                 135                 140

Asn Asn Thr Thr Glu Glu Ile Lys Asn Cys Thr Phe Asn Met Thr Thr
145                 150                 155                 160

Glu Leu Arg Asp Lys Lys Gln Gln Val Tyr Ala Leu Phe Tyr Lys Leu
                165                 170                 175

Asp Ile Val Pro Leu Asn Ser Asn Ser Ser Glu Tyr Arg Leu Ile Asn
            180                 185                 190

Cys Asn Thr Ser Ala Ile Thr Gln Ala Cys Pro Lys Val Ser Phe Asp
        195                 200                 205

Pro Ile Pro Ile His Tyr Cys Ala Pro Ala Gly Tyr Ala Ile Leu Lys
    210                 215                 220

Cys Lys Asn Asn Thr Ser Asn Gly Thr Gly Pro Cys Gln Asn Val Ser
225                 230                 235                 240

Thr Val Gln Cys Thr His Gly Ile Lys Pro Val Val Ser Thr Pro Leu
                245                 250                 255

Leu Leu Asn Gly Ser Leu Ala Glu Gly Gly Ile Ile Ile Arg Ser
            260                 265                 270

Lys Asn Leu Ser Asn Asn Ala Tyr Thr Ile Ile Val His Leu Asn Asp
        275                 280                 285

Ser Val Glu Ile Val Cys Thr Arg Pro Asn Asn Asn Thr Arg Lys Gly
    290                 295                 300

Ile Arg Ile Gly Pro Gly Gln Thr Phe Tyr Ala Thr Glu Asn Ile Ile
305                 310                 315                 320

Gly Asp Ile Arg Gln Ala His Cys Asn Ile Ser Ala Gly Glu Trp Asn
                325                 330                 335

Lys Ala Val Gln Arg Val Ser Ala Lys Leu Arg Glu His Phe Pro Asn
            340                 345                 350

Lys Thr Ile Glu Phe Gln Pro Ser Ser Gly Gly Asp Leu Glu Ile Thr
        355                 360                 365

Thr His Ser Phe Asn Cys Arg Gly Glu Phe Phe Tyr Cys Asn Thr Ser
    370                 375                 380
```

```
Lys Leu Phe Asn Ser Ser Tyr Asn Gly Thr Ser Tyr Arg Gly Thr Glu
385                 390                 395                 400

Ser Asn Ser Ser Ile Ile Thr Leu Pro Cys Arg Ile Lys Gln Ile Ile
                405                 410                 415

Asp Met Trp Gln Lys Val Gly Arg Ala Ile Tyr Ala Pro Pro Ile Glu
            420                 425                 430

Gly Asn Ile Thr Cys Ser Ser Ser Ile Thr Gly Leu Leu Leu Ala Arg
        435                 440                 445

Asp Gly Gly Leu Asp Asn Ile Thr Thr Glu Ile Phe Arg Pro Gln Gly
    450                 455                 460

Gly Asp Met Lys Asp Asn Trp Arg Asn Glu Leu Tyr Lys Tyr Lys Val
465                 470                 475                 480

Val Glu Ile Lys Pro Leu Gly Val Ala Pro Thr Glu Ala Lys Arg Arg
                485                 490                 495

Val Val Glu Arg Glu Lys Arg Ala Val Gly Ile Gly Ala Val Ile Phe
            500                 505                 510

Gly Phe Leu Gly Ala Ala Gly Ser Asn Met Gly Ala Ala Ser Ile Thr
        515                 520                 525

Leu Thr Ala Gln Ala Arg Gln Leu Leu Ser Gly Ile Val Gln Gln Gln
    530                 535                 540

Ser Asn Leu Leu Arg Ala Ile Glu Ala Gln Gln His Met Leu Gln Leu
545                 550                 555                 560

Thr Val Trp Gly Ile Lys Gln Leu Gln Ala Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
        595                 600                 605

Lys Thr Gln Gly Glu Ile Trp Glu Asn Met Thr Trp Met Gln Trp Asp
    610                 615                 620

Lys Glu Ile Ser Asn Tyr Thr Gly Ile Ile Tyr Arg Leu Leu Glu Glu
625                 630                 635                 640

Ser Gln Asn Gln Gln Glu Gln Asn Glu Lys Asp Leu Leu Ala Leu Asp
                645                 650                 655

Ser Arg Asn Asn Leu Trp Ser Trp Phe Asn Ile Ser Asn Trp Leu Trp
            660                 665                 670

Tyr Ile Lys Ile Phe Ile Met Ile Val Gly Gly Leu Ile Gly Leu Arg
        675                 680                 685

Ile Ile Phe Ala Val Leu Ser Ile Val Asn Arg Val Arg Gln Gly Tyr
    690                 695                 700

Ser Pro Leu Ser Phe Gln Thr Leu Thr Pro Asn Pro Arg Gly Leu Asp
705                 710                 715                 720

Arg Leu Gly Arg Ile Glu Glu Glu Gly Gly Glu Gln Asp Arg Asp Arg
                725                 730                 735

Ser Ile Arg Leu Val Gln Gly Phe Leu Ala Leu Ala Trp Asp Asp Leu
            740                 745                 750

Arg Ser Leu Cys Leu Phe Ser Tyr His Arg Leu Arg Asp Leu Ile Leu
        755                 760                 765

Val Thr Ala Arg Val Val Glu Leu Leu Gly Arg Ser Ser Pro Arg Gly
    770                 775                 780

Leu Gln Arg Gly Trp Glu Ala Leu Lys Tyr Leu Gly Ser Leu Val Gln
785                 790                 795                 800

Tyr Trp Gly Leu Glu Leu Lys Lys Ser Ala Thr Ser Leu Leu Asp Ser
```

```
                    805                 810                 815
Ile Ala Ile Ala Val Ala Glu Gly Thr Asp Arg Ile Ile Glu Val Ile
                820                 825                 830

Gln Arg Ile Tyr Arg Ala Phe Cys Asn Ile Pro Arg Arg Val Arg Gln
            835                 840                 845

Gly Phe Glu Ala Ala Leu Gln
        850                 855

<210> SEQ ID NO 25
<211> LENGTH: 20
<212> TYPE: PRT
<213> ORGANISM: Human immunodeficiency virus

<400> SEQUENCE: 25

Asp Ile Lys Gln Gly Pro Lys Glu Pro Phe Arg Asp Tyr Val Asp Arg
1               5                   10                  15

Phe Phe Lys Thr
            20

<210> SEQ ID NO 26
<211> LENGTH: 60
<212> TYPE: DNA
<213> ORGANISM: Human immunodeficiency virus

<400> SEQUENCE: 26
gacataaaac aaggaccaaa agagcccttt agagactatg tagaccggtt ctttaaaacc    60

<210> SEQ ID NO 27
<211> LENGTH: 20
<212> TYPE: PRT
<213> ORGANISM: Human immunodeficiency virus

<400> SEQUENCE: 27

Asp Ile Arg Gln Gly Pro Lys Glu Pro Phe Arg Asp Tyr Val Asp Arg
1               5                   10                  15

Phe Phe Lys Thr
            20

<210> SEQ ID NO 28
<211> LENGTH: 47
<212> TYPE: PRT
<213> ORGANISM: Human immunodeficiency virus

<400> SEQUENCE: 28

Thr Ile Thr Ile Thr Cys Arg Ile Lys Gln Ile Ile Asn Met Trp Gln
1               5                   10                  15

Lys Val Gly Arg Ala Met Tyr Ala Pro Pro Ile Ala Gly Asn Leu Thr
            20                  25                  30

Cys Glu Ser Asn Ile Thr Gly Leu Leu Leu Thr Arg Asp Gly Gly
        35                  40                  45

<210> SEQ ID NO 29
<211> LENGTH: 48
<212> TYPE: PRT
<213> ORGANISM: Human immunodeficiency virus

<400> SEQUENCE: 29

Ser Ile Ile Thr Leu Pro Cys Arg Ile Lys Gln Ile Ile Asp Met Trp
1               5                   10                  15

Gln Lys Val Gly Arg Ala Ile Tyr Ala Pro Pro Ile Glu Gly Asn Ile
            20                  25                  30
```

```
Thr Cys Ser Ser Ser Ile Thr Gly Leu Leu Leu Ala Arg Asp Gly Gly
    35                  40                  45
```

<210> SEQ ID NO 30
<211> LENGTH: 2469
<212> TYPE: DNA
<213> ORGANISM: Artificial Sequence
<220> FEATURE:
<223> OTHER INFORMATION: Description of Artificial Sequence: PR975(+)

<400> SEQUENCE: 30

| | |
|---|---:|
| gtcgacgcca ccatggccga ggccatgagc caggccacca cgccaacat cctgatgcag | 60 |
| cgcagcaact tcaagggccc caagcgcatc atcaagtgct tcaactgcgg caaggagggc | 120 |
| cacatcgccc gcaactgccg cgcccccgc aagaagggct gctggaagtg cggcaaggag | 180 |
| ggccaccaga tgaaggactg caccgagcgc caggccaact tcttccgcga ggacctggcc | 240 |
| ttccccagg gcaaggcccg cgagttcccc agcgagcaga accgcgccaa cagccccacc | 300 |
| agccgcgagc tgcaggtgcg cggcgacaac ccccgcagcg aggccggcgc cgagcgccag | 360 |
| ggcaccctga acttccccca gatcaccctg tggcagcgcc ccctggtgag catcaaggtg | 420 |
| ggcggccaga tcaaggaggc cctgctggac ccggcgccg acgaccgt gctggaggag | 480 |
| atgagcctgc ccggcaagtg gaagcccaag atgatcggcg catcggcgg cttcatcaag | 540 |
| gtgcgccagt acgaccagat cctgatcgag atctgcggca agaaggccat cggcaccgtg | 600 |
| ctgatcggcc ccaccccgt gaacatcatc ggccgcaaca tgctgaccca gctgggctgc | 660 |
| accctgaact tccccatcag ccccatcgag accgtgcccg tgaagctgaa gcccggcatg | 720 |
| gacggcccca aggtgaagca gtggcccctg accgaggaga gatcaaggc cctgaccgcc | 780 |
| atctgcgagg agatggagaa ggagggcaag atcaccaaga tcggcccga gaaccctac | 840 |
| aacacccccg tgttcgccat caagaagaag gacagcacca gtggcgcaa gctggtggac | 900 |
| ttccgcgagc tgaacaagcg cacccaggac ttctgggagg tgcagctggg catcccccac | 960 |
| cccgccggcc tgaagaagaa gaagagcgtg accgtgctgg acgtgggcga cgcctacttc | 1020 |
| agcgtgcccc tggacgagga cttccgcaag tacaccgcct tcaccatccc cagcatcaac | 1080 |
| aacgagaccc ccggcatccg ctaccagtac aacgtgctgc ccagggctg aagggcagc | 1140 |
| cccagcatct tccagagcag catgaccaag atcctggagc ccttccgcgc ccgcaacccc | 1200 |
| gagatcgtga tctaccagta catggacgac ctgtacgtgg gcagcgacct ggagatcggc | 1260 |
| cagcaccgcg ccaagatcga ggagctgcgc aagcacctgc tgcgctgggg cttcaccacc | 1320 |
| cccgacaaga gcaccagaa ggagcccccc ttcctgtgga tgggctacga gctgcacccc | 1380 |
| gacaagtgga ccgtgcagcc catcgagctg cccgagaagg agagctggac cgtgaacgac | 1440 |
| atccagaagc tggtgggcaa gctgaactgg gccagccaga tctaccccgg catcaaggtg | 1500 |
| cgccagctgt gcaagctgct gcgcggcgcc aaggccctga ccgacatcgt gcccctgacc | 1560 |
| gaggaggccg agctggagct ggccgagaac cgcgagatcc tgcgcgagcc cgtgcacggc | 1620 |
| gtgtactacg accccagcaa ggacctggtg gccgagatcc agaagcaggg ccacgaccag | 1680 |
| tggacctacc agatctacca ggagcccttc aagaacctga gaccggcaa gtacgccaag | 1740 |
| atgcgcaccg cccacaccaa cgacgtgaag cagctgaccg aggccgtgca gaagatcgcc | 1800 |
| atggagagca tcgtgatctg gggcaagacc cccaagttcc gcctgccat ccagaaggag | 1860 |
| acctgggaga cctggtggac cgactactgg caggccacct ggatcccga gtgggagttc | 1920 |
| gtgaacaccc cccccctggt gaagctgtgg taccagctgg agaaggagcc catcatcggc | 1980 |
| gccgagacct tctacgtgga cggcgccgcc aaccgcgaga ccaagatcgg caaggccggc | 2040 |

```
tacgtgaccg accggggccg gcagaagatc gtgagcctga ccgagaccac caaccagaag    2100
accgagctgc aggccatcca gctggccctg caggacagcg gcagcgaggt gaacatcgtg    2160
accgacagcc agtacgccct gggcatcatc caggcccagc ccgacaagag cgagagcgag    2220
ctggtgaacc agatcatcga gcagctgatc aagaaggaga aggtgtacct gagctgggtg    2280
cccgcccaca agggcatcgg cggcaacgag cagatcgaca agctggtgag caagggcatc    2340
cgcaaggtgc tgttcctgga cggcatcgat ggcggcatcg tgatctacca gtacatggac    2400
gacctgtacg tgggcagcgg cggccctagg atcgattaaa agcttcccgg ggctagcacc    2460
ggtgaattc                                                            2469

<210> SEQ ID NO 31
<211> LENGTH: 2463
<212> TYPE: DNA
<213> ORGANISM: Artificial Sequence
<220> FEATURE:
<223> OTHER INFORMATION: Description of Artificial Sequence: PR975YM

<400> SEQUENCE: 31
gtcgacgcca ccatggccga ggccatgagc caggccacca gcgccaacat cctgatgcag      60
cgcagcaact tcaagggccc caagcgcatc atcaagtgct tcaactgcgg caaggagggc     120
cacatcgccc gcaactgccg cgccccccgc aagaagggcg gctggaagtg cggcaaggag     180
ggccaccaga tgaaggactg caccgagcgc caggccaact tcttccgcga ggacctggcc     240
ttcccccagg gcaaggcccg cgagttcccc agcgagcaga accgcgccaa cagccccacc     300
agccgcgagc tgcaggtgcg cggcgacaac ccccgcagcg aggccggcgc cgagcgccag     360 ggcacccctga acttcccca gatcaccctg tggcagcgcc ccctggtgag catcaaggtg     420
ggcggccaga tcaaggaggc cctgctggac accggcgccg acgacaccgt gctggaggag     480
atgagcctgc ccggcaagtg gaagcccaag atgatcggcg gcatcggcgg cttcatcaag     540
gtgcgccagt acgaccagat cctgatcgag atctgcggca gaaggccat cggcaccgtg     600 ctgatcggcc ccacccccgt gaacatcatc ggcgcaaca tgctgaccca gctgggctgc     660
accctgaact tccccatcag ccccatcgag accgtgcccg tgaagctgaa gcccggcatg     720
gacggcccca aggtgaagca gtggcccctg accgaggaga gatcaaggc cctgaccgcc     780 atctgcgagg agatggagaa ggagggcaag atcaccaaga tcggccccga gaaccccctac    840 aacaccccg tgttcgccat caagaagaag acagcacca gtggcgcaa gctggtggac       900 ttccgcgagc tgaacaagcg cacccaggac ttctgggagg tgcagctggg catccccccac    960 cccgccggcc tgaagaagaa gaagagcgtg accgtgctgg acgtgggcga cgcctacttc    1020
agcgtgcccc tggacgagga cttccgcaag tacaccgcct tcaccatccc cagcatcaac   1080
aacgagaccc ccggcatccg ctaccagtac aacgtgctgc ccagggctg aagggcagc    1140 cccagcatct tccagagcag catgaccaag atcctggagc ccttccgcgc ccgcaacccc    1200
gagatcgtga tctaccaggc ccccctgtac gtgggcagcg acctggagat cggccagcac    1260
cgcgccaaga tcgaggagct cgcaagcac ctgctgcgct ggggcttcac cacccccgac    1320
aagaagcacc agaaggagcc ccccttcctg tggatgggct acgagctgca ccccgacaag    1380
tggaccgtgc agcccatcga gctgcccgag aaggagagct ggaccgtgaa cgacatccag    1440
aagctggtgg gcaagctgaa ctgggccagc cagatctacc ccggcatcaa ggtgcgccag    1500
ctgtgcaagc tgctgcgcgg cgccaaggcc ctgaccgaca tcgtgcccct gaccgaggag    1560
gccgagctgg agctggccga gaaccgcgag atcctgcgcg agcccgtgca cggcgtgtac    1620
```

```
tacgacccca gcaaggacct ggtggccgag atccagaagc agggccacga ccagtggacc    1680
taccagatct accaggagcc cttcaagaac ctgaagaccg gcaagtacgc caagatgcgc    1740
accgcccaca ccaacgacgt gaagcagctg accgaggccg tgcagaagat cgccatggag    1800
agcatcgtga tctggggcaa gaccccaag ttccgcctgc ccatccagaa ggagacctgg    1860
gagacctggt ggaccgacta ctggcaggcc acctggatcc ccgagtggga gttcgtgaac    1920
accccccccc tggtgaagct gtggtaccag ctggagaagg agcccatcat cggcgccgag    1980
accttctacg tggacggcgc cgccaaccgc gagaccaaga tcggcaaggc cggctacgtg    2040
accgaccggg gccggcagaa gatcgtgagc ctgaccgaga ccaccaacca gaagaccgag    2100
ctgcaggcca tccagctggc cctgcaggac agcggcagcg aggtgaacat cgtgaccgac    2160
agccagtacg ccctgggcat catccaggcc cagcccgaca gagcgagag cgagctggtg    2220 aaccagatca tcgagcagct gatcaagaag gagaaggtgt acctgagctg ggtgcccgcc    2280
cacaagggca tcggcggcaa cgagcagatc gacaagctgg tgagcaaggg catccgcaag    2340
gtgctgttcc tggacggcat cgatggcggc atcgtgatct accagtacat ggacgacctg    2400
tacgtgggca gcggcggccc taggatcgat taaaagcttc cggggctag caccggtgaa    2460 ttc                                                                 2463
```

<210> SEQ ID NO 32
<211> LENGTH: 2457
<212> TYPE: DNA
<213> ORGANISM: Artificial Sequence
<220> FEATURE:
<223> OTHER INFORMATION: Description of Artificial Sequence: PR975YMWM

<400> SEQUENCE: 32

```
gtcgacgcca ccatggccga ggccatgagc caggccacca gcgccaacat cctgatgcag     60
cgcagcaact tcaagggccc caagcgcatc atcaagtgct tcaactgcgg caaggagggc    120
cacatcgccc gcaactgccg cgccccccgc aagaagggct gctggaagtg cggcaaggag    180
ggccaccaga tgaaggactg caccgagcgc caggccaact tcttccgcga ggacctggcc    240
ttcccccagg gcaaggcccg cgagttcccc agcgagcaga accgcgccaa cagccccacc    300
agccgcgagc tgcaggtgcg cggcgacaac ccccgcagcg aggccggcgc cgagcgccag    360
ggcaccctga acttccccca gatcaccctg tggcagcgcc cctggtgag catcaaggtg    420 ggcggccaga tcaaggaggc cctgctgac accggcgccg acgacaccgt gctggaggag    480
atgagcctgc ccggcaagtg gaagcccaag atgatcggcg gcatcggcgg cttcatcaag    540
gtgcgccagt acgaccagat cctgatcgag atctgcggca agaaggccat cggcaccgtg    600
ctgatcggcc ccaccccgt gaacatcatc ggccgcaaca tgctgaccca gctgggctgc    660
accctgaact tccccatcag ccccatcgag accgtgcccg tgaagctgaa gcccggcatg    720
gacggcccca aggtgaagca gtggcccctg accgaggaga gatcaaggc cctgaccgcc    780 atctgcgagg agatggagaa ggagggcaag atcaccaaga tcggccccga gaacccctac    840
aacacccccg tgttcgccat caagaagaag acagcacca agtggcgcaa gctggtggac    900
ttccgcgagc tgaacaagcg cacccaggac ttctgggagg tgcagctggg catccccac    960 cccgccggcc tgaagaagaa gagagcgtg accgtgctgg acgtgggcga cgcctacttc    1020
agcgtgcccc tggacgagga cttccgcaag tacaccgcct tcaccatccc cagcatcaac   1080
aacgagaccc ccggcatccg ctaccagtac aacgtgctgc ccagggctg aagggcagc    1140 cccagcatct tccagagcag catgaccaag atcctggagc ccttccgcgc ccgcaacccc    1200
```

-continued

```
gagatcgtga tctaccaggc cccctgtac gtgggcagcg acctggagat cggccagcac    1260
cgcgccaaga tcgaggagct gcgcaagcac ctgctgcgct ggggcttcac caccccgac    1320 aagaagcacc agaaggagcc ccccttcctg cccatcgagc tgcacccga caagtggacc    1380 gtgcagccca tcgagctgcc cgagaaggag agctggaccg tgaacgacat ccagaagctg    1440
gtgggcaagc tgaactgggc cagccagatc taccccggca tcaaggtgcg ccagctgtgc    1500
aagctgctgc gcggcgccaa ggccctgacc gacatcgtgc ccctgaccga ggaggccgag    1560
ctggagctgg ccgagaaccg cgagatcctg cgcgagcccg tgcacggcgt gtactacgac    1620
cccagcaagg acctggtggc cgagatccag aagcagggcc acgaccagtg gacctaccag    1680
atctaccagg agcccttcaa gaacctgaag accggcaagt acgccaagat gcgcaccgcc    1740
cacaccaacg acgtgaagca gctgaccgag gccgtgcaga agatcgccat ggagagcatc    1800
gtgatctggg gcaagacccc caagttccgc ctgcccatcc agaaggagac ctgggagacc    1860
tggtggaccg actactggca ggccacctgg atccccgagt gggagttcgt gaacaccccc    1920
cccctggtga gctgtggta ccagctggag aaggagccca tcatcggcgc cgagaccttc    1980
tacgtggacg gcgccgccaa ccgcgagacc aagatcggca aggccggcta cgtgaccgac    2040
cggggccggc agaagatcgt gagcctgacc gagaccacca accagaagac cgagctgcag    2100
gccatccagc tggccctgca ggacagcggc agcgaggtga acatcgtgac cgacagccag    2160
tacgccctgg gcatcatcca ggcccagccc gacaagagcg agagcgagct ggtgaaccag    2220
atcatcgagc agctgatcaa gaaggagaag gtgtacctga gctgggtgcc cgcccacaag    2280
ggcatcggcg gcaacgagca gatcgacaag ctggtgagca agggcatccg caaggtgctg    2340
ttcctggacg gcatcgatgg cggcatcgtg atctaccagt acatggacga cctgtacgtg    2400
ggcagcggcg gccctaggat cgattaaaag cttcccgggg ctagcaccgg tgaattc    2457
```

<210> SEQ ID NO 33
<211> LENGTH: 9781
<212> TYPE: DNA
<213> ORGANISM: Human immunodeficiency virus

<400> SEQUENCE: 33

```
tggaagggtt aatttactcc aagaaaaggc aagaaatcct tgatttgtgg gtctatcaca      60
cacaaggctt cttccctgat tggcaaaact acacaccggg gccagggtc agatatccac     120 tgacctttgg atggtgctac aagctagtgc cagttgaccc aggggagtg gaagaggcca     180 acggaggaga agacaactgt ttgctacacc ctatgagcca catggagca gaggatgaag     240 atagagaagt attaaagtgg aagtttgaca gcctcctagc acgcagacac atggcccgcg     300
agctacatcc ggagtattac aaagactgct gacacagaag gactttccg cctgggactt     360 tccactgggg cgttccggga ggtgtggtct gggcgggact tggagtggt caaccctcag     420 atgctgcata taagcagctg cttttcgcct gtactgggtc tctctcggta gaccagatct     480
gagcctggga gccctctggc tatctaggga acccactgct taagcctcaa taaagcttgc     540
cttgagtgct ttaagtagtg tgtgcccatc tgttgtgtga ctctggtaac tagagatccc     600
tcagaccctt tgtggtagtg tggaaaatct ctagcagtgg cgcccgaaca gggaccagaa     660
agtgaaagtg agaccagagg agatctctcg acgcaggact cggcttgctg aagtgcacac     720
ggcaagaggc gagaggggcg gctggtgagt acgccaattt tacttgacta gcggaggcta     780
gaaggagaga gatgggtgcg agagcgtcaa tattaagcgg cggaaaatta gataaatggg     840
aaagaattag gttaaggcca gggggaaaga acattatat gttaaaacat ctagtatggg     900
```

```
caagcaggga gctggaaaga tttgcactta accctggcct gttagaaaca tcagaaggct    960
gtaaacaaat aataaaacag ctacaaccag ctcttcagac aggaacagag gaacttagat   1020
cattattcaa cacagtagca actctctatt gtgtacataa agggatagag gtacgagaca   1080
ccaaggaagc cttagacaag atagaggaag aacaaaacaa atgtcagcaa aaagcacaac   1140
aggcaaaagc agctgacgaa aaggtcagtc aaaattatcc tatagtacag aatgcccaag   1200
ggcaaatggt acaccaagct atatcaccta gaacattgaa tgcatggata aaagtaatag   1260
aggaaaaggc tttcaatcca gaggaaatac ccatgtttac agcattatca gaaggagcca   1320
ccccacaaga tttaaacaca atgttaaata cagtggggggg acatcaagca gccatgcaaa   1380
tgttaaaaga taccatcaat gaggaggctg cagaatggga taggacacat ccagtacatg   1440
cagggcctgt tgcaccaggc cagatgagag aaccaagggg aagtgacata gcaggaacta   1500
ctagtaccct tcaggaacaa atagcatgga tgacaagtaa tccacctatt ccagtagaag   1560
acatctataa aagatggata attctggggt taaataaaat agtaagaatg tatagccctg   1620
ttagcatttt ggacataaaa caagggccaa agaacccctt tagagactat gtagaccggt   1680
tctttaaaac cttaagagct gaacaagcta cacaagatgt aaagaattgg atgacagaca   1740
ccttgttggt ccaaaatgcg aacccagatt gtaagaccat tttaagagca ttaggaccag   1800
gggcctcatt agaagaaatg atgacagcat gtcagggagt gggaggaccc agccataaag   1860
caagagtgtt ggctgaggca atgagccaag caaacagtaa catactagtg cagagaagca   1920
attttaaagg ctctaacaga attattaaat gtttcaactg tggcaaagta gggcacatag   1980
ccagaaattg cagggcccct aggaaaaagg gctgttggaa atgtggacag gaaggacacc   2040
aaatgaaaga ctgtactgag aggcaggcta atttttagg gaaaatttgg ccttcccaca   2100
aggggaggcc agggaatttc ctccagaaca gaccagagcc aacagcccca ccagcagaac   2160
caacagcccc accagcagag agcttcaggt tcgaggagac aacccccgtg ccgaggaagg   2220
agaaagagag ggaacctttaa acttccctca aatcactctt tggcagcgac cccttgtctc   2280
aataaaagta gagggccaga taaaggaggc tctcttagac acaggagcag atgatacagt   2340
attagaagaa atagatttgc cagggaaatg gaaaccaaaa atgatagggg gaattggagg   2400
ttttatcaaa gtaagacagt atgatcaaat acttatagaa atttgtggaa aaaaggctat   2460
aggtacagta ttagtagggc ctacaccagt caacataatt ggaagaaatc tgttaactca   2520
gcttggatgc acactaaatt ttccaattag tcctattgaa actgtaccag taaaattaaa   2580
accaggaatg gatggcccaa aggtcaaaca atggccattg acagaagaaa aaataaaagc   2640
attaacagca atttgtgagg aaatggagaa ggaaggaaaa attacaaaaa ttgggcctga   2700
taatccatat aacactccag tatttgccat aaaaaagaag gacagtacta agtggagaaa   2760
attagtagat ttcagggaac tcaataaaag aactcaagac ttttgggaag ttcaattagg   2820
aataccacac ccagcaggat taaaaaagaa aaaatcagtg acagtgctag atgtggggga   2880
tgcatatttt tcagttcctt tagatgaaag cttcaggaaa tatactgcat tcaccatacc   2940
tagtataaac aatgaaacac cagggattag atatcaatat aatgtgctgc cacagggatg   3000
gaaaggatca ccagcaatat tccagagtag catgacaaaa atcttagagc ccttcagagc   3060
aaaaaatcca gacatagtta tctatcaata tatggatgac ttgtatgtag gatctgactt   3120
agaaataggg caacatagag caaaaataga gagttaagg gaacatttat tgaaatgggg   3180
atttacaaca ccagacaaga aacatcaaaa agaaccccca tttctttgga tggggtatga   3240
actccatcct gacaaatgga cagtacaacc tatactgctg ccagaaaagg atagttggac   3300
```

```
tgtcaatgat atacagaagt tagtgggaaa attaaactgg gcaagtcaga tttacccagg   3360
gattaaagta aggcaactct gtaaactcct caggggggcc aaagcactaa cagacatagt   3420
accactaact gaagaagcag aattagaatt ggcagagaac agggaaattt taagagaacc   3480
agtacatgga gtatattatg atccatcaaa agacttgata gctgaaatac agaaacaggg   3540
gcatgaacaa tggacatatc aaatttatca agaaccattt aaaaatctga aaacagggaa   3600
gtatgcaaaa atgaggacta cccacactaa tgatgtaaaa cagttaacag aggcagtgca   3660
aaaaatagcc atggaaagca tagtaatatg gggaaagact cctaaattta gactacccat   3720
ccaaaaagaa acatgggaga catggtggac agactattgg caagccacct ggatccctga   3780
gtgggagttt gttaataccc ctcccctagt aaaattatgg taccaactag aaaaagatcc   3840
catagcagga gtagaaactt tctatgtaga tggagcaact aatagggaag ctaaaatagg   3900
aaaagcaggg tatgttactg acagaggaag gcagaaaatt gttactctaa ctaacacaac   3960
aaatcagaag actgagttac aagcaattca gctagctctg caggattcag gatcagaagt   4020
aaacatagta acagactcac agtatgcatt aggaatcatt caagcacaac cagataagag   4080
tgactcagag atatttaacc aaataataga acagttaata aacaaggaaa gaatctacct   4140
gtcatgggta ccagcacata aaggaattgg gggaaatgaa caagtagata aattagtaag   4200
taagggaatt aggaaagtgt tgtttctaga tggaatagat aaagctcaag aagagcatga   4260
aaggtaccac agcaattgga gagcaatggc taatgagttt aatctgccac ccatagtagc   4320
aaaagaaata gtagctagct gtgataaatg tcagctaaaa ggggaagcca tacatggaca   4380
agtcgactgt agtccaggga tatggcaatt agattgtacc catttagagg gaaaaatcat   4440
cctggtagca gtccatgtag ctagtggcta catggaagca gaggttatcc cagcagaaac   4500
aggacaagaa acagcatatt ttatattaaa attagcagga agatggccag tcaaagtaat   4560
acatacagac aatggcagta attttaccag tactgcagtt aaggcagcct gttggtgggc   4620
aggtatccaa caggaatttg gaattcccta caatccccaa agtcagggag tggtagaatc   4680
catgaataaa gaattaaaga aaataatagg acaagtaaga gatcaagctg agcaccttaa   4740
gacagcagta caaatggcag tattcattca caattttaaa agaaaagggg gaattggggg   4800
gtacagtgca ggggaaagaa taatagacat aatagcaaca gacatacaaa ctaaagaatt   4860
acaaaaacaa attataagaa ttcaaaattt tcgggtttat tacagagaca gcagagaccc   4920
tatttggaaa ggaccagccg aactactctg gaaaggtgaa ggggtagtag taatagaaga   4980
taaaggtgac ataaaggtag taccaaggag gaaagcaaaa atcattagag attatggaaa   5040
acagatggca ggtgctgatt gtgtggcagg tggacaggat gaagattaga gcatggaata   5100
gtttagtaaa gcaccatatg tatatatcaa ggagagctag tggatgggtc tacagacatc   5160
attttgaaag cagacatcca aaagtaagtt cagaagtaca tatcccatta ggggatgcta   5220
gattagtaat aaaaacatat gggggtttgc agacaggaga aagagattgg catttgggtc   5280
atggagtctc catagaatgg agactgagag aatacagcac acaagtagac cctgacctgg   5340
cagaccagct aattcacatg cattattttg attgttttac agaatctgcc ataagacaag   5400
ccatattagg acacatagtt tttcctaggt gtgactatca agcaggacat aagaaggtag   5460
gatctctgca atacttggca ctgacagcat tgataaaacc aaaaaagaga aagccacctc   5520
tgcctagtgt tagaaaatta gtagaggata gatggaacga cccccagaag accaggggcc   5580
gcagagggaa ccatacaatg aatggacact agagattcta gaagaactca agcaggaagc   5640
tgtcagacac tttcctagac catggctcca tagcttagga caatatatct atgaaaccta   5700
```

```
tggggatact tggacgggag ttgaagctat aataagagta ctgcaacaac tactgttcat    5760
tcatttcaga attggatgcc aacatagcag aataggcatc ttgcgacaga gaagagcaag    5820
aaatggagcc agtagatcct aaactaaagc cctggaacca tccaggaagc caacctaaaa    5880
cagcttgtaa taattgcttt tgcaaacact gtagctatca ttgtctagtt tgctttcaga    5940
caaaaggttt aggcatttcc tatggcagga agaagcggag acagcgacga agcgctcctc    6000
caagtggtga agatcatcaa aatcctctat caaagcagta agtacacata gtagatgtaa    6060
tggtaagttt aagtttattt aaaggagtag attatagatt aggagtagga gcattgatag    6120
tagcactaat catagcaata atagtgtgga ccatagcata tatagaatat aggaaattgg    6180
taagacaaaa gaaaatagac tggttaatta aagaattag ggaaagagca gaagacagtg    6240
gcaatgagag tgatggggac acagaagaat tgtcaacaat ggtggatatg gggcatctta    6300
ggcttctgga tgctaatgat ttgtaacacg gaggacttgt gggtcacagt ctactatggg    6360
gtacctgtgt ggagagaagc aaaaactact ctattctgtg catcagatgc taaagcatat    6420
gagacagaag tgcataatgt ctgggctaca catgcttgtg tacccacaga ccccaaccca    6480
caagaaatag ttttgggaaa tgtaacagaa aatttttaata tgtggaaaaa taacatggca    6540
gatcagatgc atgaggatat aatcagttta tgggatcaaa gcctaaagcc atgtgtaaag    6600
ttgaccccac tctgtgtcac tttaaactgt acagatacaa atgttacagg taatagaact    6660
gttacaggta atacaaatga taccaatatt gcaaatgcta catataagta tgaagaaatg    6720
aaaaattgct ctttcaatgc aaccacagaa ttaagagata gaaacataa agagtatgca    6780
ctctttata aacttgatat agtaccactt aatgaaaata gtaacaactt tacatataga    6840
ttaataaatt gcaatacctc aaccataaca caagcctgtc caaaggtctc ttttgacccg    6900
attcctatac attactgtgc tccagctgat tatgcgattc taaagtgtaa taataagaca    6960
ttcaatggga caggaccatg ttataatgtc agcacagtac aatgtacaca tggaattaag    7020
ccagtggtat caactcaact actgttaaat ggtagtctag cagaagaagg gataataatt    7080
agatctgaaa atttgacaga gaataccaaa acaataatag tacatcttaa tgaatctgta    7140
gagattaatt gtacaaggcc caacaataat acaaggaaaa gtgtaaggat aggaccagga    7200
caagcattct atgcaacaaa tgacgtaata ggaaacataa gacaagcaca ttgtaacatt    7260
agtacagata gatggaataa aactttacaa caggtaatga aaaaattagg agagcatttc    7320
cctaataaaa caataaaatt tgaaccacat gcaggagggg atctagaaat tacaatgcat    7380
agctttaatt gtagaggaga attttttctat tgcaatacat caaacctgtt taatagtaca    7440
tactacccta agaatggtac atacaaatac aatggtaatt caagcttacc catcacactc    7500
caatgcaaaa taaaacaaat tgtacgcatg tggcaagggg taggacaagc aatgtatgcc    7560
cctcccattg caggaaacat aacatgtaga tcaaacatca caggaatact attgacacgt    7620
gatgggggat ttaacaacac aaacaacgac acagaggaga cattcagacc tggaggagga    7680
gatatgaggg ataactggag aagtgaatta tataaatata agtggtaga aattaagcca    7740
ttgggaatag cacccactaa ggcaaaaaga agagtggtgc agagaaaaaa aagagcagtg    7800
ggaataggag ctgtgttcct tgggttcttg ggagcagcag gaagcactat gggcgcagcg    7860
tcaataacgc tgacggtaca ggccagacaa ctgttgtctg gtatagtgca acagcaaagc    7920
aatttgctga aggctataga ggcgcaacag catatgttgc aactcacagt ctggggcatt    7980
aagcagctcc aggcgagagt cctggctata gaaagatacc taaaggatca acagctccta    8040
gggatttggg gctgctctgg aagactcatc tgcaccactg ctgtgccttg gaactccagt    8100
```

```
tggagtaata aatctgaagc agatatttgg gataacatga cttggatgca gtgggataga      8160
gaaattaata attacacaga acaatattc aggttgcttg aagactcgca aaaccagcag       8220
gaaaagaatg aaaaagattt attagaattg gacaagtgga ataatctgtg gaattggttt     8280
gacatatcaa actggctgtg gtatataaaa atattcataa tgatagtagg aggcttgata     8340
ggtttaagaa taattttgc tgtgctctct atagtgaata gagttaggca gggatactca      8400
cctttgtcat ttcagacccct taccccaagc ccgagggac tcgacaggct cggaggaatc     8460
gaagaagaag gtggagagca agacagagac agatccatac gattggtgag cggattcttg    8520
tcgcttgcct gggacgatct gcggagcctg tgcctcttca gctaccaccg cttgagagac    8580
ttcatattaa ttgcagtgag gcagtggaa cttctgggac acagcagtct caggggacta     8640 cagaggggt gggagatcct taagtatctg gaagtcttg tgcagtattg gggtctagag      8700
ctaaaaaaga gtgctattag tccgcttgat accatagcaa tagcagtagc tgaaggaaca    8760
gataggatta tagaattggt acaaagaatt tgtagagcta tcctcaacat acctaggaga    8820
ataagacagg gctttgaagc agctttgcta taaaatggga ggcaagtggt caaaacgcag    8880
catagttgga tggcctgcag taagagaaag aatgagaaga actgagccag cagcagaggg   8940
agtaggagca gcgtctcaag acttagatag acatgggca cttacaagca gcaacacacc    9000
tgctactaat gaagcttgtg cctggctgca agcacaagag gaggacggag atgtaggctt    9060
tccagtcaga cctcaggtac ctttaagacc aatgacttat aagagtgcag tagatctcag    9120 cttctttta aaagaaaagg ggggactgga agggttaatt tactctagga aaaggcaaga    9180
aatccttgat ttgtgggtct ataacacaca aggcttcttc cctgattggc aaaactacac    9240
atcggggcca gggtccgat tcccactgac ctttggatgg tgcttcaagc tagtaccagt     9300
tgacccaagg gaggtgaaag aggccaatga aggagaagac aactgtttgc tacaccctat    9360
gagccaacat ggagcagagg atgaagatag agaagtatta agtgaagt ttgacagcct      9420 tctagcacac agacacatgg cccgcgagct acatccggag tattacaaag actgctgaca    9480
cagaagggac tttccgcctg ggactttcca ctggggcgtt ccggaggtg tggtctgggc    9540 gggacttggg agtggtcacc ctcagatgct gcatataagc agctgctttt cgcttgtact     9600
gggtctctct cggtagacca gatctgagcc tgggagctct ctggctatct agggaaccca    9660
ctgcttaggc ctcaataaag cttgccttga gtgctctaag tagtgtgtgc ccatctgttg    9720
tgtgactctg gtaactagag atccctcaga ccctttgtgg tagtgtggaa aatctctagc    9780
a                                                                       9781

<210> SEQ ID NO 34
<211> LENGTH: 203
<212> TYPE: DNA
<213> ORGANISM: Human immunodeficiency virus

<400> SEQUENCE: 34
gctgaggcaa tgagccaagc aaccagcgca acatactga tgcagagaag caatttcaaa      60
ggccctaaaa gaattattaa atgtttcaac tgtggcaagg aagggcacat agctagaaat    120
tgtagggccc ctaggaaaaa aggctgttgg aaatgtggaa aggaaggaca ccaaatgaaa     180
gactgtactg agaggcaggc taa                                             203

<210> SEQ ID NO 35
<211> LENGTH: 2151
<212> TYPE: DNA
<213> ORGANISM: Human immunodeficiency virus
```

<400> SEQUENCE: 35

```
tttttttaggg aagatttggc cttcccacaa gggaaggcca gggaatttcc ttcagaacag      60
aacagagcca acagccccac cagcagagag cttcaagttc gaggagacaa ccccgctcc      120
gaagcaggag ccgaaagaca gggaaccctt aatttccctc aaatcactct ttggcagcga     180
ccccttgtct caataaaagt aggggtcaa ataaaggagg ctctcttaga cacaggagct      240
gatgatacag tattagaaga aatgagtttg ccaggaaaat ggaaaccaaa aatgatagga     300
ggaattggag gttttatcaa agtaagacag tatgatcaaa tacttataga aatttgtgga    360
aaaaaggcta taggtacagt attaatagga cctacacctg tcaacataat tggaaggaat    420
atgttgactc agcttggatg cacactaaat tttccaatta gtcccattga aactgtgcca    480
gtaaaattaa agccaggaat ggatggccca aaggttaaac aatggccatt gacagaagag    540
aaaataaaag cattaacagc aatttgtgaa gaaatggaga aggaaggaaa aattacaaaa   600
attgggcctg aaaatccata taacactcca gtatttgcca taaaaaagaa ggacagtact   660
aagtggagaa agttagtaga tttcaggaa cttaataaaa gaactcaaga cttttgggaa    720
gttcaattag gaataccaca cccagcaggg ttaaaaaaga aaaaatcagt gacagtactg    780
gatgtggggg atgcatattt ttcagttcct ttagatgagg acttcaggaa atatactgca    840
ttcaccatac ctagtataaa caatgaaaca ccagggatta gatatcaata taatgtgctt    900
ccacagggat ggaaaggatc accatcaata ttccagagta gcatgacaaa aatcttagag    960
ccctttagag caagaaatcc agaaatagtc atctatcaat atatggatga cttgtatgta  1020
ggatctgact tagaaatagg gcaacataga gcaaaaatag aggagttaag aaaacatctg   1080
ttaaggtggg gatttaccac accggacaag aaacatcaga agaaccccc atttctttgg    1140
atggggtatg aactccatcc tgacaaatgg acagtacagc ctatagagtt gccagaaaag    1200
gaaagctgga ctgtcaatga tatacagaag ttagtgggaa aattaaattg ggccagtcag    1260
atttacccag gaattaaagt aaggcaactt tgtaaactcc ttaggggggc caaagcacta    1320
acagatatag taccactaac tgaagaagca gaattagaat tggcagagaa cagggaaatt    1380
ctaagagaac cagtacatgg agtatattat gacccatcaa aagacttggt agctgaaata    1440
cagaaacagg ggcatgacca atggacatat caaatttacc aagaaccatt caaaaacctg    1500
aaaacaggga agtatgcaaa aatgaggact gcccacacta atgatgtaaa acagttaaca    1560
gaggcagtgc aaaaaatagc tatggaaagc atagtaatat ggggaaagac tcctaaattt    1620
agactaccca tccaaaaaga aacatgggag acatggtgga cagactattg gcaagccacc    1680
tggattcctg agtgggagtt tgttaatacc cctcccttag taaaattatg gtaccagcta   1740
gagaaagaac ccataatagg agcagaaact ttctatgtag atggagcagc taatagggaa   1800
actaaaatag gaaaagcagg gtatgttact gacagaggaa ggcagaaaat tgtttctcta   1860
acagaaacaa caaatcagaa gactgaatta caagcaattc agctagcttt gcaagattca    1920
ggatcagaag taaacatagt aacagactca cagtatgcat taggaatcat tcaagcacaa    1980
ccagataaga gtgaatcaga gttagtcaac caaataatag aacaattaat aaaaaaggaa   2040
aaggtctacc tgtcatgggt accagcacat aaaggaattg gaggaaatga acaaatagat   2100
aaattagtaa gtaagggaat caggaaagtg ctgtttctag atggaataga t             2151
```

<210> SEQ ID NO 36
<211> LENGTH: 54
<212> TYPE: DNA
<213> ORGANISM: Human immunodeficiency virus

```
<400> SEQUENCE: 36
ggcggcatcg tgatctacca gtacatggac gacctgtacg tgggcagcgg cggc        54

<210> SEQ ID NO 37
<211> LENGTH: 18
<212> TYPE: PRT
<213> ORGANISM: Human immunodeficiency virus

<400> SEQUENCE: 37

Gly Gly Ile Val Ile Tyr Gln Tyr Met Asp Asp Leu Tyr Val Gly Ser
 1               5                  10                  15

Gly Gly

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: primer
      S1FCSacTA

<400> SEQUENCE: 38
gtttcttgag ctctggaagg gttaatttac tccaagaa                          38

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: primer
      S1FTSacTA

<400> SEQUENCE: 39
gtttcttgag ctctggaagg gttaatttac tctaagaa                          38

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: primer
      S145RTSalTA

<400> SEQUENCE: 40
gtttcttgtc gacttgtcca tgtatggctt cccct                             35

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: primer
      S145RCSalTA

<400> SEQUENCE: 41
gtttcttgtc gacttgtcca tgcatggctt ccct                              34

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: primer
      S245FASalTA

<400> SEQUENCE: 42
```

```
gtttcttgtc gactgtagtc caggaatatg gcaattag                               38

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: primer
      S245FGSalTA

<400> SEQUENCE: 43
gtttcttgtc gactgtagtc cagggatatg gcaattag                               38

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: primer
      S2FullNotTA

<400> SEQUENCE: 44
gtttcttgcg gccgctgcta gagattttcc acactacca                              39

<210> SEQ ID NO 45
<211> LENGTH: 9738
<212> TYPE: DNA
<213> ORGANISM: Human immunodeficiency virus

<400> SEQUENCE: 45
tggaagggtt aatttactcc aggaaaaggc aagagatcct tgatttatgg gtctatcaca       60
cacaaggcta cttccctgat ggcaaaact acacaccggg accagggtc agatatccac        120 tgacctttgg atggtgcttc aagctagtgc cagttgaccc aagggaagta aagaggcca       180 acggaggaga agacaactgt tgctacacc ctatgagcca gtatgaatg atgatgaac         240 acaaagaagt gttacagtgg aagtttgaca gcagcctagc acgcagacac ctggcccgcg      300
agctacatcc ggattattac aaagactgct gacacagaag gactttccg cctgggactt      360 tccactgggg cgttccaggg ggagtggtct gggcgggact gggagtggcc agccctcaga     420
tgctgcatat aagcagcggc ttttcgcctg tactgggtct ctctaggtag accagatccg     480
agcctgggag ctctctgtct atctggggaa cccactgctt aggcctcaat aaagcttgcc     540
ttgagtgctc taagtagtgt gtgcccatct gttgtgtgac tctggtaact ctggtaacta    600
gagatccctc agaccctttg tggtagtgtg aaaatctct agcagtggcg cccgaacagg     660
gacttgaaag cgaaagtgag accagagaag atctctcgac gcaggactcg gcttgctgaa     720
gtgcactcgg caagaggcga ggggggcgac tggtgagtac gccaaaattt tttttgacta     780
gcggaggcta aaggagaga gatgggtgcg agagcgtcaa tattaagagg gggaaaatta     840
gacaaatggg aaaaaattag gttacggcca ggggggagaa aacactatat gctaaaacac     900
ctagtatggg caagcagaga gctggaaaga tttgcagtta accctggcct tttagagaca      960
tcagacggat gtagacaaat aataaaacag ctacaaccag ctcttcagac aggaacagag     1020
gaaattagat cattatttaa cacagtagca actctctatt gtgtacataa agggatagat     1080
gtacgagaca ccaaggaagc cttagacaag atagaggagg aacaaacaa atgtcagcaa     1140 aaaacacagc aggcggaagc ggctgacaaa aaggtcagtc aaaattatcc tatagtgcag     1200
aacctccaag ggcaaatggt acaccaggcc atatcaccta gaaccttgaa tgcatgggta     1260
aaagtaatag aggagaaggc ttttagccca gaggtaatac ccatgtttac agcattatca     1320
```

```
gaaggagcca ccccacaaga tttaaacacc atgttaaata cagtgggggg acatcaagca    1380
gccatgcaaa tgttaaaaga taccatcaat gaggaggctg cagaatggga taggttacat    1440
ccagtacatg cagggcctgt tgcaccaggc cagatgagag aaccaagggg aagtgacata    1500
gcaggaacta ctagtaccct tcaagaacaa atagcatgga tgacaagtaa cccacctatc    1560
ccagtagggg acatctataa aaggtggata attctggggt taaataaaat agtaagaatg    1620
tacagccctg tcagcatttt agacataaaa caaggaccaa aggaaccctt tagagactat    1680
gtagaccggt tcttcaaaac tttaagagct gaacaatcta cacaagaggt aaaaaattgg    1740
atgacagaca ccttgttagt ccaaaatgcg aacccagatt gtaagaccat tttaagagca    1800
ttaggaccag gggcttcatt agaagaaatg atgacagcat gtcagggagt ggggaggacct   1860 agccacaaag caagagtttt ggctgaggca atgagccaag caaacaatac aagtgtaatg    1920
atacagaaaa gcaattttaa aggccctaga agagctgtta aatgtttcaa ctgtggcagg    1980
gaagggcaca tagccaggaa ttgcagggcc cctaggaaaa ggggctgttg aaatgtgga    2040 aaggaaggac accaaatgaa agactgtact gagaggcagg ctaatttttt agggaaaatt    2100
tggccttccc acaaggggag gccagggaat ttccttcaga gcagaccaga gccaacagcc    2160
ccaccactag aaccaacagc cccaccagca gagagcttca gttcaagga gactccgaag    2220 caggagccga aagacaggga acctttaact tccctcaaat cactctttgg cagcgacccc    2280
ttgtctcaat aaaagtagcg ggccaaacaa aggaggctct tttagataca ggagcagatg    2340
atacagtact agaagaaata aacttgccag gaaaatggaa accaaaaatg ataggaggaa    2400
ttggaggttt tatcaaagta agacagtatg atcaaatact tatagaaatt tgtggaaaaa    2460
gggctatagg tacagtatta gtaggaccta cacctgtcaa cataattgga agaaatctgt    2520
tgactcagct tggatgcaca ctaaattttc caattagccc cattgaaact gtaccagtaa    2580
aattaaagcc aggaatggat ggcccaaagg ttaaacaatg gccattgaca gaagaaaaa    2640 taaaagcatt aacagaaatt tgtgaggaaa tggagaagga aggaaaaatt acaaaaattg    2700
ggcctgaaaa tccatataac actccagtat ttgccataaa gaagaaggac agtacaaagt    2760
ggagaaaatt agtagatttc agggaactca ataaaagaac tcaagacttt tgggaagtcc    2820
aattaggaat accacaccca gcagggttaa aaagaaaaaa atcagtgaca gtactggatg    2880
tgggagatgc atattttca gtcccttag atgagagctt cagaaaatat actgcattca    2940
ccatacctag tataaacaat gaaacaccag ggattagata tcaatataat gttcttccac    3000
agggatggaa aggatcacca gcaatattcc agagtagcat gacaagaatc ttagagccct    3060
ttagaacaca aaacccagaa gtagttatct atcaatatat ggatgactta tatgtaggat    3120
ctgacttaga aatagggcaa catagagcaa aaatagagga gttaagagga cacctattga    3180 aatgggatt taccacacca gacaagaaac atcagaaaga accccatttt ctttggatgg    3240
ggtatgaact ccatcctgac aaatggacag tacagcctat acagctgcca gaaaaggaga    3300
gctggactgt caatgatata cagaagttag tgggaaagtt aaactgggca agtcagattt    3360
acccagggat taaagtaagg caactgtgta aactccttag gggagccaaa gcactaacag    3420
acatagtgcc actgactgaa gaagcagaat tagaattggc tgagaacagg gaaattctaa    3480
aagaaccagt acatggagta tattatgacc catcaaaaga tttaatagct gaaatacaga    3540
aacaggggaa tgaccaatgg acatatcaaa tttaccaaga accatttaaa atctgagaa    3600 caggaaagta tgcaaaaatg aggactgccc acactaatga tgtgaaacag ttagcagagg    3660
cagtgcaaaa gataacccag gaaagcatag taatatgggg aaaaactcct aaatttagac    3720
```

```
tacccatccc aaaagaaaca tgggagacat ggtggtcaga ctattggcaa gccacctgga   3780
ttcctgagtg ggagtttgtc aatacccctc ccctagtaaa attgtggtac cagctggaaa   3840
aagaacccat agtaggggca gaaactttct atgtagatgg agcagccaat agggaaacta   3900
aaataggaaa agcagggtat gtcactgaca aaggaaggca gaaagttgtt tccttcactg   3960
aaacaacaaa tcagaagact gaattacaag caattcagct agctttgcag gattcagggc   4020
cagaagtaaa catagtaaca gactcacagt atgcattagg aatcattcaa gcacaaccag   4080
ataagagtga atcagaatta gtcagtcaaa taatagaaca gttgataaaa aggaaaaag   4140 tctacctatc atgggtacca gcacataaag gaattggagg aaatgaacaa gtagacaaat   4200
tagtaagtag tggaatcaga aaagtactgt ttctagatgg aatagataaa gctcaagaag   4260
agcatgaaaa atatcacagc aattggagag caatggctag tgagtttaat ctgccaccca   4320
tagtagcaaa ggaaatagta gccagctgtg ataaatgtca gctaaagggg aagccatgc    4380 atggacaagt cgactgtagt ccaggaatat ggcaattaga ctgtacacat ttagaaggaa   4440
aaatcatcct agtagcagtc catgtagcca gtggctacat ggaagcagag gttatcccag   4500
cagaaacagg acaagaaaca gcatacttta tactaaaatt agcaggaaga tggccagtca   4560
aagtaataca tacagataat ggcagtaatt tcaccagtac cgcagttaag gcagcctgtt   4620
ggtgggcaga tatccaacgg gaatttggaa ttccctacaa tccccaaagt caaggagtag   4680
tagaatccat gaataaagaa ttaaagaaaa tcatagggca agtaagagat caagctgagc   4740
accttaagac agcagtacaa atggcagtat tcattcacaa ttttaaaaga aaagggggga   4800 ttgggggta cagtgcaggg gagagaataa tagacataat agcatcagac atacaaacta   4860
aagaattaca aaaacaaatt ataaaaattc aaaattttcg ggtttattac agagacagca   4920
gagaccctat ttggaaagga ccagccaaac tactctggaa aggtgaaggg gcagtagtaa   4980
tacaagataa tagtgatata aaggtagtac caagaaggaa agcaaaaatc attaaggact   5040
atggaaaaca gatggcaggt gctgattgtg tggcaggtag acaggatgaa gattagaaca   5100
tggcacagtt tagtaaagca ccatatgtat gtttcgagga gagctgatgg atggttctac   5160
agacatcatt atgaaagcag acacccaaaa gtaagttcag aagtacacat cccattagga   5220
gatgccaggt tagtaataaa aacatattgg ggtctgcaga caggagaaag agcttggcat   5280
ttgggtcacg gagtctccat agaatggaga ttgagaagat atagcacaca agtagaccct   5340
gacctgacag accaactaat tcatatgcat tattttgatt gttttgcaga atctgccata   5400
aggaaagcca tactaggaca gatagttagc cctaagtgtg actatcaagc aggacataac   5460
aaggtaggat ctctacaata cttggcactg acagcattga taaaaccaaa aaagataaag   5520
ccacctctgc ctagtgttag gaaattagta gaggatagat ggaacaagcc ccagaagacc   5580
aggggccgca gagggaacca tacaatgaat ggacactaga gcttttagaa gaactcaagc   5640
aggaagctgt cagacacttt cctagaccat ggctccataa cttaggacaa catatctatg   5700
aaacctatgg agatacttgg acaggagttg aagcaataat aagaatcctg caacaattac   5760
tgtttattca tttcaggatt gggtgccatc atagcagaat aggcattttg cgacagagaa   5820
gagcaagaaa tggagccaat agatcctaac ctagaaccct ggaaccatcc aggaagtcag   5880
cctaaaactg cttgtaatgg gtgttactgt aaacgttgca gctatcattg tctagtttgc   5940
tttcagaaaa aaggcttagg catttactat ggcaggaaga gcggagaca gcgacgaagc   6000 gctcctccaa gcaataaaga tcatcaagat cctctaccaa agcagtaagt accgaatagt   6060
atatgtaatg ttagatttaa ctgcaagaat agattctaga ttaggaatag gagcattgat   6120
```

```
agtagcacta atcatagcaa taatagtgtg gaccatagta tatatagaat ataggaaatt    6180
ggtaaggcaa aggaaaatag actggttagt taaaaggatt agggaaagag cagaagacag    6240
tggcaatgag agcgaggggg atactgaaga attatcgaca ctggtggata tgggcatct     6300 taggcttttg gatgctaatg atgtgtaatg tgaagggctt gtgggtcaca gtctactacg    6360
gggtacctgt ggggagagaa gcaaaaacta ctctattttg tgcatcagat gctaaagcat    6420
atgagaaaga agtgcataat gtctgggcta cacatgcctg tgtacccaca gaccccaacc    6480
cacaagaagt gattttgggc aatgtaacag aaaattttaa catgtggaaa aatgacatgg    6540
tggatcagat gcaggaagat ataatcagtt tatgggatca aagccttaag ccatgtgtaa    6600
aattgacccc actctgtgtc actttaaact gtacaaatgc aactgttaac tacaataata    6660
cctctaaaga catgaaaaat tgctctttct atgtaaccac agaattaaga gataagaaaa    6720
agaaagaaaa tgcactttt tatagacttg atatagtacc acttaataat aggaagaatg     6780
ggaatattaa caactataga ttaataaatt gtaataccctc agcctaaaca caagcctgtc    6840
caaaagtctc gtttgaccca attcctatac attattgtgc tccagctggt tatgcgcctc    6900
taaaatgtaa taataagaaa ttcaatggaa taggaccatg cgataatgtc agcacagtac    6960
aatgtacaca tggaattaag ccagtggtat caactcaatt actgttaaat ggtagcctag    7020
cagaagaaga gataataatt agatctgaaa atctgacaaa caatgtcaaa acaataatag    7080
tacatcttaa tgaatctata gagattaaat gtacaagacc tggcaataat acaagaaaga    7140
gtgtgagaat aggaccagga caagcattct atgcaacagg agacataata ggagatataa    7200
gacaagcaca ttgtaacatt agtaaaaatg aatggaatac aactttacaa agggtaagtc    7260
aaaaattaca agaactcttc cctaatagta cagggataaa atttgcacca cactcaggag    7320
gggacctaga aattactaca catagcttta attgtggagg agaatttttc tattgcaata    7380
caacagacct gtttaatagt acatacagta atggtacatg cactaatggt acatgcatgt    7440
ctaataatac agagcgcatc acactccaat gcagaataaa acaaattata aacatgtggc    7500
aggaggtagg acgagcaatg tatgcccctc ccattgcagg aaacataaca tgtagatcaa    7560
atattacagg actactatta acacgtgatg gaggagataa taatactgaa acagagacat    7620
tcagacctgg aggaggagac atgagggaca attggagaag tgaattatat aaatacaagg    7680
tggtagaaat taaaccatta ggagtagcac ccactgctgc aaaaaggaga gtggtggaga    7740
gagaaaaaag agcagtagga ataggagctg tgttccttgg gttcttggga gcagcaggaa    7800
gcactatggg cgcagcatca ataacgctga cggtacaggc cagacaatta ttgtctggta    7860
tagtgcaaca gcaaagtaat ttgctgaggg ctatagaggc gcaacagcat atgttgcaac    7920
tcacggtctg gggcattaag cagctccagg caagagtcct ggctatagag agatacctac    7980
aggatcaaca gctcctagga ctgtggggct gctctggaaa actcatctgc accactaatg    8040
tgctttggaa ctctagttgg agtaataaaa ctcaaagtga tatttgggat aacatgacct    8100
ggatgcagtg ggatagggaa attagtaatt acacaaacac aatatacagg ttgcttgaag    8160
actcgcaaag ccagcaggaa agaaatgaaa aagatttact agcattggac aggtggaaca    8220
atctgtggaa ttggtttagc ataacaaatt ggctgtggta tataaaaata ttcataatga    8280
tagtaggagg cttgataggt ttaagaataa ttttgctgt gctctctcta gtaaatagag      8340
ttaggcaggg atactcaccc ttgtcattgc agacccttat cccaaacccg aggggacccg    8400
acaggctcga aggaatcgaa gaagaaggtg gagagcaaga cagcagcaga tccattcgat    8460
tagtgagcgg attcttgaca cttgcctggg acgacctacg aagcctgtgc ctcttctgct    8520
```

```
accaccgatt gagagacttc atattaattg tagtgagagc agtggaactt ctgggacaca    8580
gtagtctcag gggactgcag aggggtggg gaacccttaa gtatttgggg agtcttgtgc    8640
aatattgggg tctagagtta aaaaagagtg ctattaatct gcttgatact atagcaatag    8700
cagtagctga aggaacagat aggattctag aattcataca aaacctttgt agaggtatcc    8760
gcaacgtacc tagaagaata agacagggct tcgaagcagc tttgcaataa aatgggggc    8820 aagtggtcaa aaagcagtat aattggatgg cctgaagtaa gagaaagaat cagacgaact    8880
aggtcagcag cagagggagt aggatcagcg tctcaagact tagagaaaca tggggcactt    8940
acaaccagca acacagccca caacaatgct gcttgcgcct ggctggaagc gcaagaggag    9000
gaaggagaag taggctttcc agtcagacct caggtacctt taagaccaat gacttataaa    9060
gcagcaatag atctcagctt cttttaaaa gaaaaggggg gactggaagg gttaatttac    9120
tccaagaaaa ggcaagagat ccttgatttg tgggtttata acacacaagg cttcttccct    9180
gattggcaaa actacacacc gggaccaggg gtcagatttc cactgacctt tggatggtac    9240
ttcaagctag agccagtcga tccaagggaa gtagaagagg ccaatgaagg agaaaacaac    9300
tgtttactac accctatgag ccagcatgga atggaggat aagacagaga agtattaaga    9360
tggaagtttg acagtacgct agcacgcaga cacatggccc gcgagctaca tccggagtat    9420
tacaaagact gctgacacag aagggactt ccgctgggac tttccactgg ggcgttccag    9480
gaggtgtggt ctgggcggga caggggagtg gtcagccctg agatgctgca tataagcagc    9540
tgcttttcgc ctgtactggg tctctctagg tagaccagat ctgagcccgg gagctctctg    9600
gctatctagg gaacccactg cttaagcctc aataaagctt gccttgagtg ccttgagtag    9660
tgtgtgcccg tctgttgtgt gactctggta actagagatc cctcagacca cttgtggtag    9720
tgtggaaaat ctctagca                                                  9738

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: spacer

<400> SEQUENCE: 46

Gly Gly Gly Ser
 1
```

The invention claimed is:

1. An expression cassette, comprising a polynucleotide sequence operably linked to a promoter, wherein the polynucleotide sequence has at least 90% sequence identity to SEQ ID NO:30; SEQ ID NO:31; or SEQ ID NO:32.

2. The expression cassette of claim 1, further comprising one or more nucleic acids encoding one or more viral polypeptides or antigens.

3. The expression cassette of claim 2, wherein the viral polypeptides or antigens are selected from the group consisting of Gag, Env, vif, vpr, tat, rev, vpu, nef and combinations thereof.

4. The expression cassette of claim 1, further comprising one or more nucleic acids encoding one or more cytokines.

5. A recombinant expression system for use in a selected host cell, comprising, the expression cassette of claim 1, and wherein said polynucleotide sequence is operably linked to control elements compatible with expression in the selected host cell.

6. The recombinant expression system of claim 5, wherein said control elements are selected from the group consisting of a transcription promoter, a transcription enhancer element, a transcription termination signal, polyadenylation sequences, sequences for optimization of initiation of translation, and translation termination sequences.

7. The recombinant expression system of claim 6, wherein said transcription promoter is selected from the group consisting of CMV, CMV+intron A, SV40, RSV, HIV-Ltr, MMLV-ltr, and metallothionein.

8. A cell comprising the expression cassette of claim 1, and wherein said polynucleotide sequence is operably linked to control elements compatible with expression in the selected cell.

9. The cell of claim 8, wherein the cell is a mammalian cell.

10. The cell of claim 9, wherein the cell is selected from the group consisting of BHK, VERO, HT1080, 293, RD, COS-7, and CHO cells.

11. The cell of claim 10, wherein said cell is a CHO cell.

12. The cell of claim 8, wherein the cell is an insect cell.

13. The cell of claim 12, wherein the cell is either *Trichoplusia ni* (Tn5) or Sf9 insect cells.

14. The cell of claim 8, wherein the cell is a bacterial cell.

15. The cell of claim 8, wherein the cell is a yeast cell.

16. The cell of claim 8, wherein the cell is a plant cell.

17. The cell of claim 8, wherein the cell is an antigen presenting cell.

18. The cell of claim 17, wherein the antigen presenting cell is a lymphoid cell selected from the group consisting of macrophage, monocytes, dendritic cells, B-cells, T-cells, stem cells, and progenitor cells thereof.

19. The cell of claim 8, wherein the cell is a primary cell.

20. The cell of claim 8, wherein the cell is an immortalized cell.

21. The cell of claim 8, wherein the cell is a tumor cell.

22. A composition for generating an immunological response, comprising the expression cassette of claim 1.

23. The composition of claim 22, further comprising one or more Pol polypeptides.

24. The composition of claim 23, further comprising an adjuvant.

25. A composition for generating an immunological response, comprising the expression cassette of claim 2.

26. The composition of claim 25, further comprising a Pol polypeptide.

27. The composition of claim 26, further comprising a polypeptide encoded by a polynucleotide sequence operably linked to a promoter, wherein the polynucleotide sequence encodes an HIV Pol polypeptide that elicits a Pol-specific immune response, and further wherein the polynucleotide sequence encoding said polypeptide comprises a nucleotide sequence having at least 90% sequence identity to SEQ ID NO:30; SEQ ID NO:31; or SEQ ID NO:32.

28. The composition of claim 27, further comprising an adjuvant.

29. A method of generating an immune response in a subject, comprising, introducing the composition of claim 22 into said subject under conditions that are compatible with expression of said expression cassette in said subject.

30. The method of claim 29, wherein said expression cassette is introduced using a gene delivery vector.

31. The method of claim 30, wherein the gene delivery vector is a non-viral vector.

32. The method of claim 30, wherein said gene delivery vector is a viral vector.

33. The method of claim 32, wherein said gene delivery vector is a Sindbis virus derived vector.

34. The method of claim 32, wherein said gene delivery vector is a retroviral vector.

35. The method of claim 32, wherein said gene delivery vector is a lentiviral vector.

36. The method of claim 30, wherein said composition is delivered by using a particulate carrier.

37. The method of claim 30, wherein said composition is coated on a gold or tungsten particle and said coated particle is delivered to said subject using a gene gun.

38. The method of claim 30, wherein said composition is encapsulated in a liposome preparation.

39. The method of any one of claims 30-38, wherein said subject is a mammal.

40. The method of claim 39, wherein said mammal is a human.

41. The method of claim 29, where the method further comprises administration of a polypeptide derived from an HIV.

42. The method of claim 41, wherein administration of the polypeptide to the subject is carried out before introducing said expression cassette.

43. The method of claim 41, wherein administration of the polypeptide to the subject is carried out concurrently with introducing said expression cassette.

44. The method of claim 41, wherein administration of the polypeptide to the subject is carried out after introducing said expression cassette.

45. The expression cassette of claim 2, wherein the viral polypeptides or antigens are selected from the group consisting of polypeptides derived from hepatitis B, hepatitis C and combinations thereof.

46. An expression cassette comprising the polynucleotide sequence of SEQ ID NO: 30, SEQ ID NO: 31 or SEQ ID NO: 32.

47. The expression cassette of claim 46 further comprising a nucleotide sequence encoding a viral polypeptide selected from the group consisting of Gag, Env, vif, vpr, tat, rev, vpu, nef, and combinations thereof.

48. A composition for generating an immunological response in a mammal comprising the expression cassette of claim 46.

49. A method of generating an immune response in a mammal, the method comprising the step of intramuscularly administering the expression cassette of claim 46 to said mammal.

50. The expression cassette of claim 1, comprising a nucleotide sequence encoding an HIV-1 Pol polypeptide, wherein the catalytic center region of the Reverse-Transcriptase is modified to become non-functional, and wherein said nucleotide sequence has at least 90% sequence identity to SEQ ID NO:31.

51. The expression cassette of claim 1, comprising a nucleotide sequence encoding an HIV-1 Pol polypeptide, wherein the catalytic center and the primer grip region of the Reverse-Transcriptase are modified to become non-functional, and wherein said nucleotide sequence has at least 90% sequence identity to SEQ ID NO:32.

* * * * *